US011369364B2

(12) United States Patent
Skinlo et al.

(10) Patent No.: US 11,369,364 B2
(45) Date of Patent: Jun. 28, 2022

(54) SUTURE PASSING SYSTEMS AND METHODS

(71) Applicant: MARKER MEDICAL, LLC, Logan, UT (US)

(72) Inventors: David Skinlo, North Logan, UT (US); Ephraim Akyuz, Logan, UT (US); Daniel Perkins, Hyde Park, UT (US)

(73) Assignee: Marker Medical, LLC, Logan, UT (US)

( * ) Notice: Subject to any disclaimer, the term of this patent is extended or adjusted under 35 U.S.C. 154(b) by 335 days.

(21) Appl. No.: 16/166,012

(22) Filed: Oct. 19, 2018

(65) Prior Publication Data

US 2019/0053793 A1    Feb. 21, 2019

Related U.S. Application Data

(63) Continuation of application No. 15/074,670, filed on Mar. 18, 2016, now abandoned, which is a continuation of application No. PCT/US2014/056408, filed on Sep. 18, 2014, and a continuation-in-part of application No. 13/779,652, filed on Feb. 27, 2013, now abandoned, and a
(Continued)

(51) Int. Cl.
*A61B 17/04*  (2006.01)
*A61B 17/062* (2006.01)
*A61B 17/06*  (2006.01)

(52) U.S. Cl.
CPC .... *A61B 17/0469* (2013.01); *A61B 17/06004* (2013.01); *A61B 17/0625* (2013.01); *A61B 2017/0608* (2013.01); *A61B 2017/06019* (2013.01); *A61B 2017/06042* (2013.01); *A61B 2017/06071* (2013.01); *A61B 2017/06095* (2013.01)

(58) Field of Classification Search
CPC ............ A61B 17/0469; A61B 17/0483; A61B 17/062; A61B 17/0625; A61B 2017/047; A61B 2017/0472; A61B 2017/0474; A61B 17/06004; A61B 17/06019; A61B 17/0608; A61B 17/06095; A61B 17/06042; A61B 17/06071
See application file for complete search history.

(56) References Cited

U.S. PATENT DOCUMENTS

| 6,770,084 B1* | 8/2004 | Bain | A61B 17/0469 606/144 |
| 2003/0065337 A1* | 4/2003 | Topper | A61B 17/0625 606/144 |

(Continued)

*Primary Examiner* — Katherine H Schwiker
(74) *Attorney, Agent, or Firm* — David Meibos; Maywood IP Law

(57) ABSTRACT

An implant manipulator may have a distal end that retains an implant, a proximal end, and an intermediate portion between the ends. The implant manipulator may be a needle for a suture passer, with a suture capture feature at the distal end. The suture capture feature may have first and second members that flex apart to permit entry of the suture into a suture capture hole wherein the suture is retained until released. A suture passer may include one or more needles. The suture passer may also include a pusher; a distal end with a sharp, blade-like extension; or a side-loading distal end.

20 Claims, 38 Drawing Sheets

Related U.S. Application Data continuation-in-part of application No. 13/779,595, filed on Feb. 27, 2013, now Pat. No. 9,572,566.

(60) Provisional application No. 61/879,388, filed on Sep. 18, 2013, provisional application No. 61/605,143, filed on Feb. 29, 2012.

(56) References Cited

U.S. PATENT DOCUMENTS

| | | | |
|---|---|---|---|
| 2003/0078599 A1* | 4/2003 | O'Quinn | A61B 17/0469 606/144 |
| 2003/0078600 A1* | 4/2003 | O'Quinn | A61B 17/0469 606/144 |
| 2005/0154402 A1* | 7/2005 | Sauer | A61B 17/0482 606/139 |
| 2010/0305583 A1* | 12/2010 | Baird | A61B 17/0469 606/144 |
| 2011/0028998 A1* | 2/2011 | Adams | A61B 17/0482 606/145 |
| 2011/0066165 A1* | 3/2011 | Skinlo | A61B 17/0469 606/145 |
| 2011/0118760 A1* | 5/2011 | Gregoire | A61B 17/0469 606/145 |
| 2011/0301620 A1* | 12/2011 | Di Betta | A61B 17/0469 606/144 |
| 2013/0023988 A1* | 1/2013 | Sinnott | A61B 17/0469 623/13.14 |
| 2014/0296880 A1* | 10/2014 | Heneveld | A61B 17/0469 606/144 |

\* cited by examiner

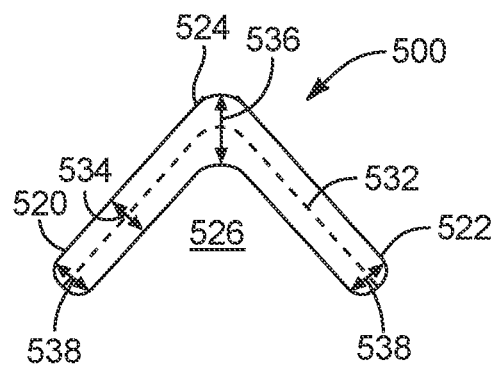
FIG. 5A
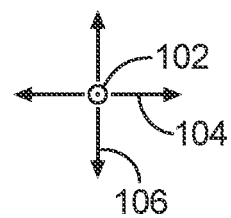
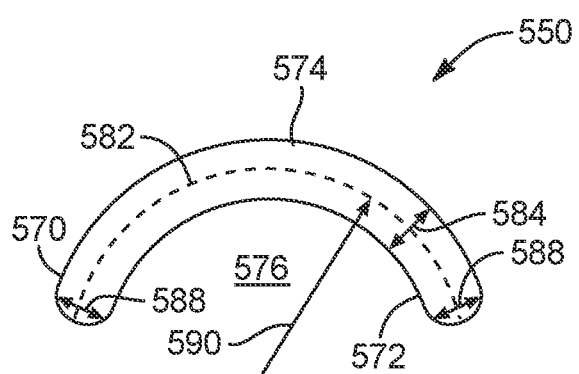
FIG. 5B

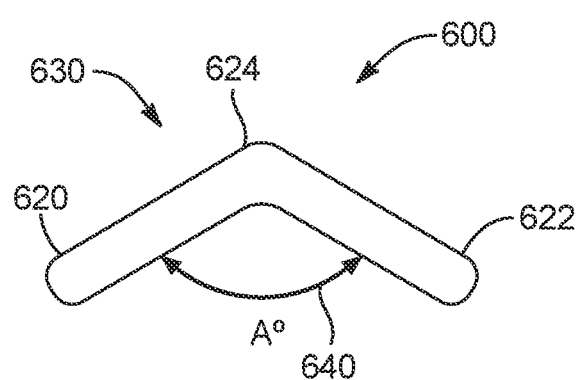
FIG. 6A
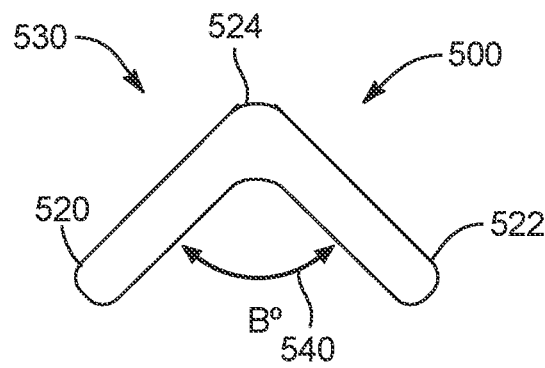
FIG. 6B
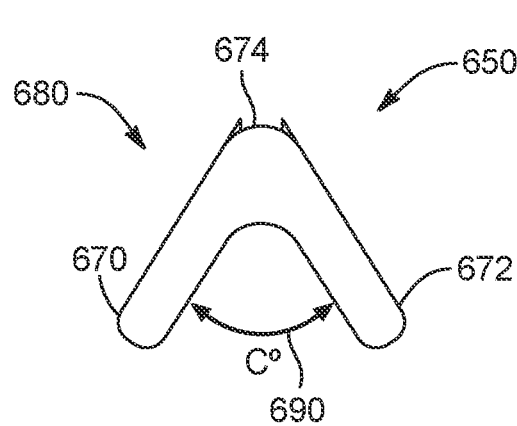
FIG. 6C
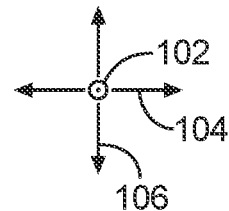

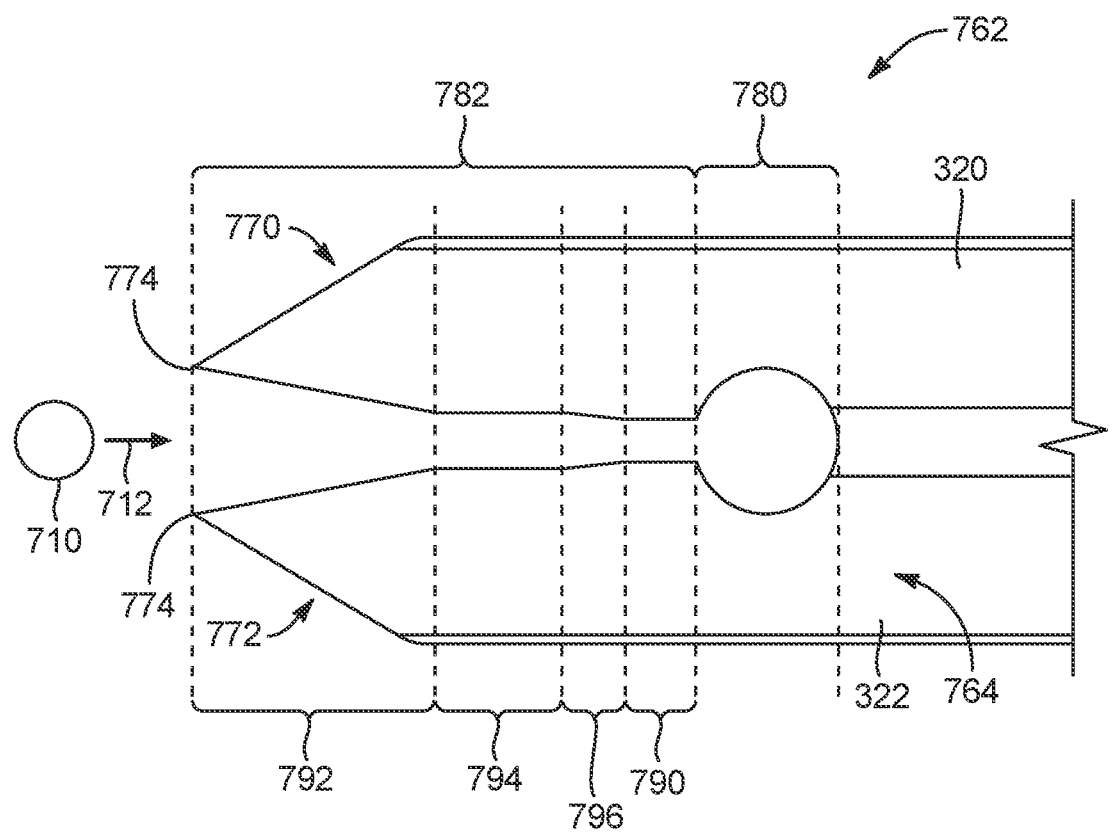
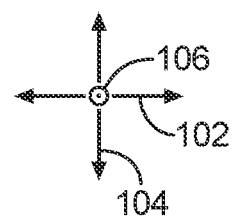
FIG. 7B

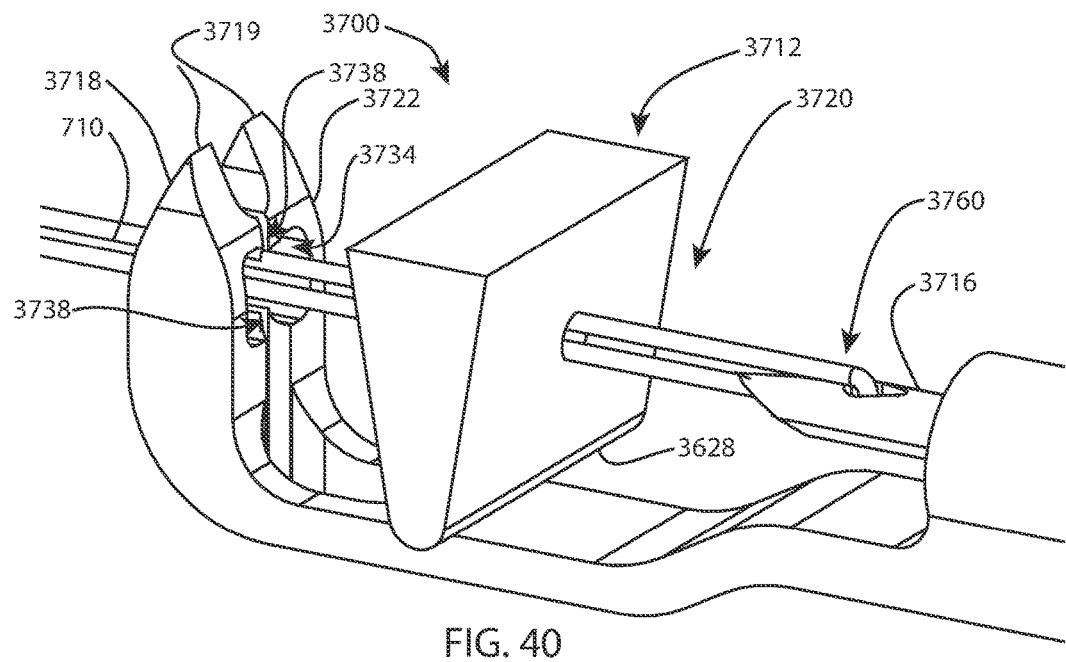
FIG. 40
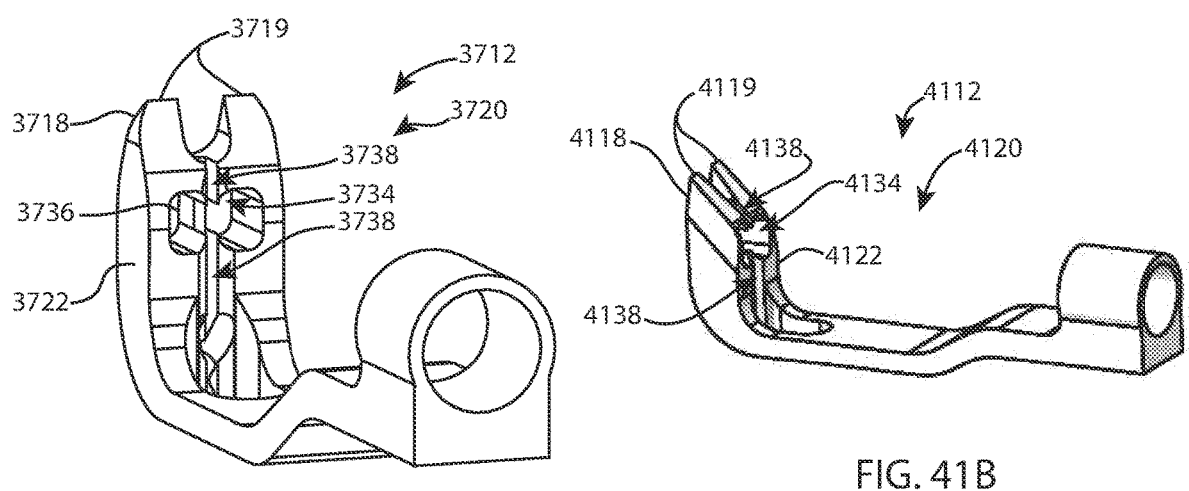
FIG. 41A
FIG. 41B

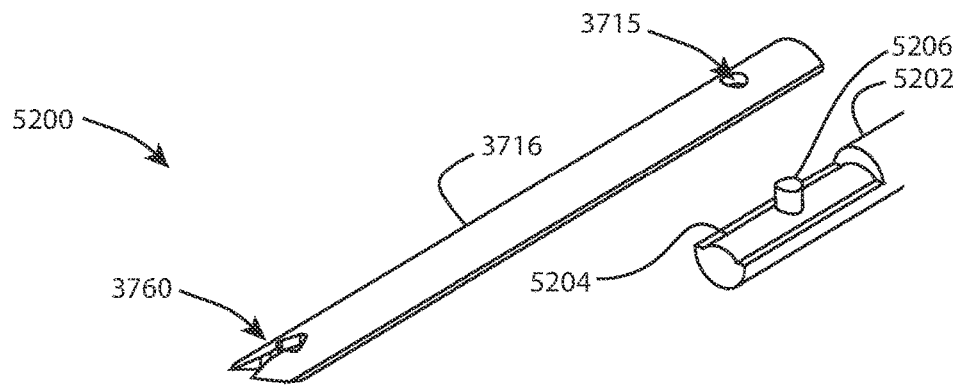
FIG. 52 - PRIOR ART
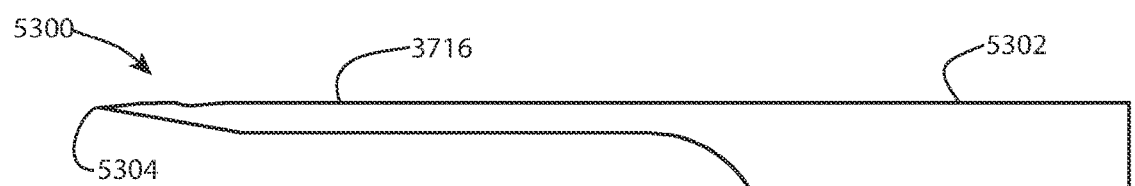
FIG. 53A
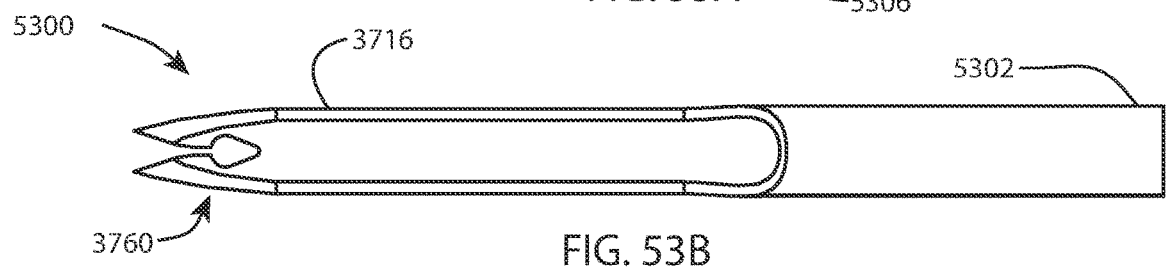
FIG. 53B
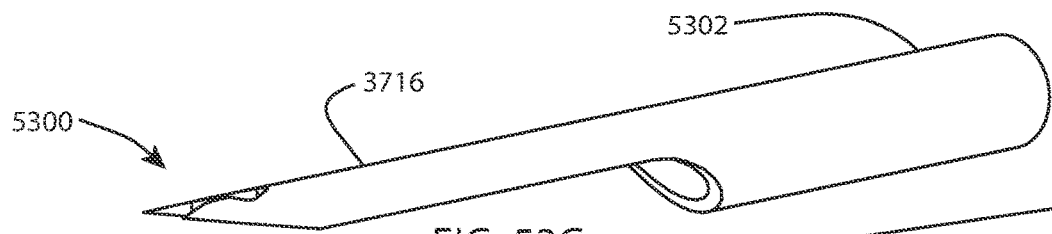
FIG. 53C
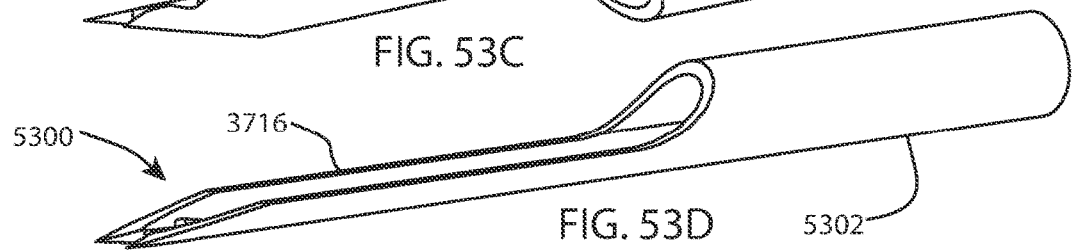
FIG. 53D

SUTURE PASSING SYSTEMS AND METHODS

CROSS-REFERENCE TO RELATED APPLICATIONS

The present application is a continuation of U.S. patent application Ser. No. 15/074,670, entitled SUTURE PASSING SYSTEMS AND METHODS, filed Mar. 18, 2016, which is a continuation of International Application No. PCT/US14/56408, entitled SUTURE PASSING SYSTEMS AND METHODS, filed Sep. 18, 2014, which claims the benefit of U.S. Provisional Application Ser. No. 61/879,388, entitled SUTURE PASSING SYSTEMS AND METHODS, filed on Sep. 18, 2013. U.S. patent application Ser. No. 15/074,670 is also a continuation-in-part of U.S. patent application Ser. No. 13/779,595, entitled SURGICAL APPARATUS AND METHOD, filed on Feb. 27, 2013 and U.S. patent application Ser. No. 13/779,652, entitled SURGICAL APPARATUS AND METHOD, filed on Feb. 27, 2013. U.S. patent application Ser. Nos. 13/779,595 and 13/779,652 claim the benefit of U.S. Provisional Application Ser. No. 61/605,143, entitled NOVEL SUTURE PASSER, which was filed on Feb. 29, 2012. The foregoing applications are incorporated herein by reference as though set forth in their entirety.

TECHNICAL FIELD

The present invention relates to surgical instruments, and more particularly to instruments that are used to insert, pass, or retrieve surgical implants within the body.

BACKGROUND

There are a multitude of endoscopic, arthroscopic or other surgical procedures that require the ability to pass suture through soft tissues as part of an effort to repair various damaged structures. Surgical instruments specifically designed to pass and/or retrieve suture through tissue have become increasingly popular among surgeons. Due to the size constraints of the surgical procedure, the pathway for the needle to pass through the instrument and tissue is typically non-linear. Because of this non-linear pathway, the needle used to pass or retrieve the suture must be flexible enough to bend, yet rigid enough to still pass through the tissue to be sutured. Some existing needles are unable to reliably meet these requirements.

The specific mechanism by which the suture can be passed or retrieved may be accomplished by the needle, the instrument, or a secondary suture capturing feature such as a wire loop snare. Suture mechanisms involving the instrument or secondary features will add complexity to the design of the instrument and may even add steps to the surgical procedure. Mechanisms that utilize the needle for suture retrieval typically do not actively grasp the suture without assistance from other features on the instrument.

In order to consistently pass and retrieve suture through tissue, a complex process is involved that combines the challenges, described above, of passing a needle over a non-linear pathway and reliably retrieving the suture, all while operating through a small cannula and working in the confines of a small anatomical space.

Aside from sutures, other types of implant devices may be required to be implanted with constraints similar to those described above. These implants may need to be implanted or removed over a non-linear pathway relative to the access ports. Accordingly, procedures involving such implants are similarly difficult with existing technology.

SUMMARY

The various systems and methods of the present technology have been developed in response to the present state of the art, and in particular, in response to the problems and needs in the art that have not yet been fully solved by currently available suture passers.

In an aspect of the technology, a suture passer system for a suture having a first free end, a second free end opposite the first free end, and a middle portion between the first free end and the second free end includes: a suture passer having a proximal end, a distal end opposite the proximal end, an intermediate portion coupled to and extending between the proximal end and the distal end, and a first needle residing at least partially within the intermediate portion; wherein the distal end of the suture passer includes a suture holding feature; wherein a distal end of the first needle has a distally-sharpened first member, a distally-sharpened second member, and a channel extending between the first member and the second member; wherein the first needle is movable between a retracted position and an extended position, wherein the first needle resides at least partially within the intermediate portion of the suture passer when the first needle is in the retracted position, wherein the first needle extends to the suture holding feature in the distal end of the suture passer when the first needle is in the extended position; wherein the suture is transferred between the distal end of the suture passer and the first needle when the first needle moves between the retracted position and the extended position.

Embodiments may include some or all of the following characteristics.

The suture holding feature includes a slot extending across the distal end of the suture passer, wherein the suture is transferred between the slot and the channel when the first needle moves between the retracted position and the extended position.

The first needle includes a capture hole, wherein the channel provides access to the capture hole; wherein the suture is transferred between the slot and the capture hole when the first needle moves between the retracted position and the extended position.

The suture passer system includes a pusher component including a shaft and a distal portion extending from the shaft, the distal portion including at least one pushing arm; wherein the pusher component is movable between a retracted position and an extended position, wherein the pusher component resides at least partially within the intermediate portion of the suture passer when the pusher component is in the retracted position, wherein the pusher component extends against the slot of the distal end of the suture passer when the pusher component in the extended position; wherein the suture is transferred from the capture hole to the slot when the first needle is in the extended position and the pusher component moves between the retracted position and the extended position.

The pusher component is biased to remain in, or to automatically move to, the retracted position except when the pusher component is actuated to move the pusher component distally toward the extended position.

The distal end of the suture passer includes a sharp, blade-like extension.

The suture holding feature includes a first tab coupled to the distal end of the suture passer, wherein the suture is transferred from the channel to the first tab when the first needle moves between the retracted position and the extended position.

The distal end of the suture passer includes a distal wall and a base opposite the distal wall, wherein the base is coupled to the intermediate portion of the suture passer, wherein the base includes at least one slot that receives the suture, wherein the at least one slot of the base is aligned with the channel of the first needle when the first needle is in the retracted position.

The distal wall includes at least one proximally-facing protrusion.

The first needle is biased to remain in, or to automatically move to, the retracted position except when the first needle is actuated to move the first needle distally toward the extended position.

The suture passer system includes a second needle residing at least partially within the intermediate portion of the suture passer; wherein a distal end of the second needle includes a distally-sharpened first member, a distally-sharpened second member, and a channel extending between the first member of the second needle and the second member of the second needle; wherein the second needle is movable between a retracted position and an extended position, wherein the second needle resides at least partially within the intermediate portion of the suture passer when the second needle is in the retracted position, wherein the second needle extends to the suture holding feature in the distal end of the suture passer when the second needle is in the extended position; wherein the suture is transferred between the distal end of the suture passer and the second needle when the second needle moves between the retracted position and the extended position.

The suture holding feature includes a second tab coupled to the distal end of the suture passer, wherein the suture is transferred from the channel of the second needle to the second tab when the second needle moves between the retracted position and the extended position.

The suture holding feature includes a slot extending across the distal end of the suture passer, wherein the suture is transferred between the slot and the channel of the second needle when the second needle moves between the retracted position and the extended position.

The second needle includes a capture hole, wherein the channel of the second needle provides access to the capture hole of the second needle; wherein the suture is transferred between the slot and the capture hole of the second needle when the second needle moves between the retracted position and the extended position.

In another aspect of the technology, a suture passer system for a suture having a first free end, a second free end opposite the first free end, and a middle portion between the first free end and the second free end includes: a suture passer having a proximal end, a distal end opposite the proximal end, an intermediate portion coupled to and extending between the proximal end and the distal end, and a first needle residing at least partially within the intermediate portion; wherein the distal end of the suture passer has a distal wall oriented transversely to the intermediate portion, wherein the distal wall has a suture holding feature, wherein the distal wall terminates in a sharp, blade-like extension; wherein the first needle is movable between a retracted position and an extended position, wherein the first needle resides at least partially within the intermediate portion of the suture passer when the first needle is in the retracted position, wherein the first needle extends to the suture holding feature when the first needle is in the extended position; wherein the suture is transferred between the distal end of the suture passer and the first needle when the first needle moves between the retracted position and the extended position.

Embodiments may include some or all of the following characteristics. The sharp, blade-like extension is divided into at least two portions by at least one slot. At least one side of the sharp, blade-like extension is beveled. At least two sides of the sharp, blade-like extension are beveled. The distal wall includes at least one proximally-facing protrusion.

In yet another aspect of the technology, a suture passer system for a suture having a first free end, a second free end opposite the first free end, and a middle portion between the first free end and the second free end includes: a suture passer having a proximal end, a distal end opposite the proximal end, an intermediate portion coupled to and extending between the proximal end and the distal end, a first needle residing at least partially within the intermediate portion, and a first pusher component residing at least partially within the intermediate portion; wherein the distal end of the suture passer has a suture holding feature; wherein the first pusher component includes at least one pushing arm extending beside the first needle; wherein the first needle includes a capture hole; wherein the first needle is movable between a retracted position and an extended position, wherein the first needle resides at least partially within the intermediate portion of the suture passer when the first needle is in the retracted position, wherein the first needle extends to the suture holding feature when the first needle is in the extended position; wherein the first pusher component is movable between a retracted position and an extended position, wherein the first pusher component resides at least partially within the intermediate portion of the suture passer when the first pusher component is in the retracted position, wherein the first pusher component extends to the suture holding feature when the first pusher component is in the extended position; wherein the suture is transferred from the capture hole of the first needle to the distal end of the suture passer when the first needle is in the extended position and the first pusher component moves between the retracted position and the extended position.

Embodiments may include some or all of the following characteristics. The first pusher component is independently movable relative to the first needle. The first pusher component includes a shaft and a distal portion extending from the shaft, wherein the distal portion includes the at least one pushing arm. The shaft of the first pusher component extends beside the needle in the intermediate component of the suture passer. The first pusher component includes at least two pushing arms extending beside the first needle. The at least two pushing arms are on opposite sides of the first needle.

In yet another aspect of the technology, a suture passer system for a suture having a first free end, a second free end opposite the first free end, and a middle portion between the first free end and the second free end includes: a suture passer having a proximal end, a distal end opposite the proximal end, an intermediate portion coupled to and extending between the proximal end and the distal end, and a first needle residing at least partially within the intermediate portion; wherein the distal end of the suture passer includes a distal wall oriented transversely to the intermediate portion, wherein the distal wall includes a suture holding feature including a slot extending across the distal wall, wherein the slot extends laterally through a side of the distal end of the suture passer to form a lateral alcove in the distal end of the suture passer; wherein the first needle is movable between a retracted position and an extended position, wherein the first needle resides at least partially within the intermediate portion of the suture passer when the first needle is in the retracted position, wherein the first needle extends to the suture holding feature when the first needle is in the extended position; wherein the suture is transferred between the distal end of the suture passer and the first needle when the first needle moves between the retracted position and the extended position.

Embodiments may include some or all of the following characteristics. A proximal portion of the slot extends laterally through a side of the distal end of the suture passer to form an enlarged lateral alcove in the distal end of the suture passer. The distal wall adjacent to the alcove extends proximally, terminating in a proximally-projecting free end. The distal wall includes at least one proximally-facing protrusion.

In yet another aspect of the technology, a suture passer system for a suture including a first free end, a second free end opposite the first free end, and a middle portion between the first free end and the second free end includes: a suture passer including a proximal end, a distal end opposite the proximal end, an intermediate portion coupled to and extending between the proximal end and the distal end, a first needle, and a second needle, wherein the first needle and the second needle reside at least partially within the intermediate portion; wherein the distal end of the suture passer includes a suture holding feature; wherein the first needle and the second needle each include a distal end including a distally-sharpened first member, a distally-sharpened second member, and a channel extending between the first member and the second member; wherein the first needle is movable between a retracted position and an extended position, wherein the first needle resides at least partially within the intermediate portion of the suture passer when the first needle is in the retracted position, wherein the first needle extends to the suture holding feature in the distal end of the suture passer when the first needle is in the extended position; wherein the second needle is movable between a retracted position and an extended position, wherein the second needle resides at least partially within the intermediate portion of the suture passer when the second needle is in the retracted position, wherein the second needle extends to the suture holding feature in the distal end of the suture passer when the second needle is in the extended position; wherein the first free end of the suture is transferred between the distal end of the suture passer and the first needle when the first needle moves between the retracted position and the extended position; wherein the second free end of the suture is transferred between the distal end of the suture passer and the second needle when the second needle moves between the retracted position and the extended position.

Embodiments may include some or all of the following characteristics. The distal end of the suture passer includes a base coupled to the intermediate portion of the suture passer, wherein the base includes at least one slot that receives the suture, wherein the at least one slot is aligned with a first channel when the first needle is in the retracted position, wherein the first channel is selected from the group consisting of the channel of the first needle and the channel of the second needle. The base includes a first slot and a second slot, wherein the first slot is aligned with the channel of the first needle when the first needle is in the retracted position and the second slot is aligned with the channel of the second needle when the second needle is in the retracted position. The suture holding feature includes a first tab coupled to the distal end of the suture passer, wherein the suture is transferred from the channel of the first needle to the first tab when the first needle moves between the retracted position and the extended position. The suture holding feature includes a second tab coupled to the distal end of the suture passer, wherein the suture is transferred from the channel of the second needle to the second tab when the second needle moves between the retracted position and the extended position. The suture holding feature includes a slot extending across the distal end of the suture passer, wherein the second needle includes a capture hole, wherein the channel of the second needle provides access to the capture hole, wherein the suture is transferred between the slot and the capture hole of the second needle when the second needle moves between the retracted position and the extended position.

In yet another aspect of the technology, a needle for a suture passer system includes: a proximal end including a tubular shank; a distal end opposite the proximal end; and an intermediate portion extending between the proximal end and the distal end; wherein, in an undeflected state, the needle includes a uniform cross sectional shape along an entire length of the needle, wherein the cross sectional shape extends along a nonlinear pathway.

Embodiments may include some or all of the following characteristics. A distal end of the needle includes a distally-sharpened first member, a distally-sharpened second member, and a channel extending distally between the first member and the second member.

The needle includes a capture hole, wherein the channel provides access to the capture hole. The intermediate portion includes a slot extending through the intermediate portion and extending between the proximal end and the distal end. The uniform cross sectional shape is selected from the group of cross-sectional shapes consisting of polygonal, triangular, square, rectangular, quadrilateral, parallelogram, rhombus, trapezoid, diamond-shaped, D-shaped, round, circular, oval, elliptical, and ovoid. These and other features and advantages of the present technology will become more fully apparent from the following description and appended claims, or may be learned by the practice of the technology as set forth hereinafter.

BRIEF DESCRIPTION OF THE DRAWINGS

Various embodiments of the technology will be described in conjunction with the accompanying drawings. These drawings are to be construed as non-limiting examples of the present technology; those of skill in the art will appreciate that a wide variety of modifications are possible within the scope and spirit of the technology.

FIGS. 5A-5H are end views of alternative implant manipulators show varying cross-sectional shapes including U-shaped and V-shaped cross-sections.

FIGS. 6A-6C are end views of alternative implant manipulators illustrating how the cross-sectional shape of the needle may be altered over a wide range of angles.

FIG. 7B is a top view of the distal end of a needle with a suture capture feature according to another alternative embodiment of the invention.

FIG. 40 is a perspective detail view of the distal tip portion of the suture passer, the suture, and the tissue portion of FIG. 38, with the needle of the suture passer in the partially retracted position, the suture passing through the tissue portion.

FIG. 41A is a perspective view of the distal tip portion of the suture passer of FIG. 37.

FIG. 41B is a perspective view of another distal tip portion for a suture passer.

FIG. 52 is an exploded perspective view of a prior art needle assembly for a suture passer, with a needle and a shaft.

FIG. 53A is a side view of yet another needle for a suture passer.

FIG. 53B is a bottom view of the needle of FIG. 53A.

FIG. 53C is a perspective view of the needle of FIG. 53A.

FIG. 53D is another perspective view of the needle of FIG. 53A from a different angle.

DETAILED DESCRIPTION

Figure 58:
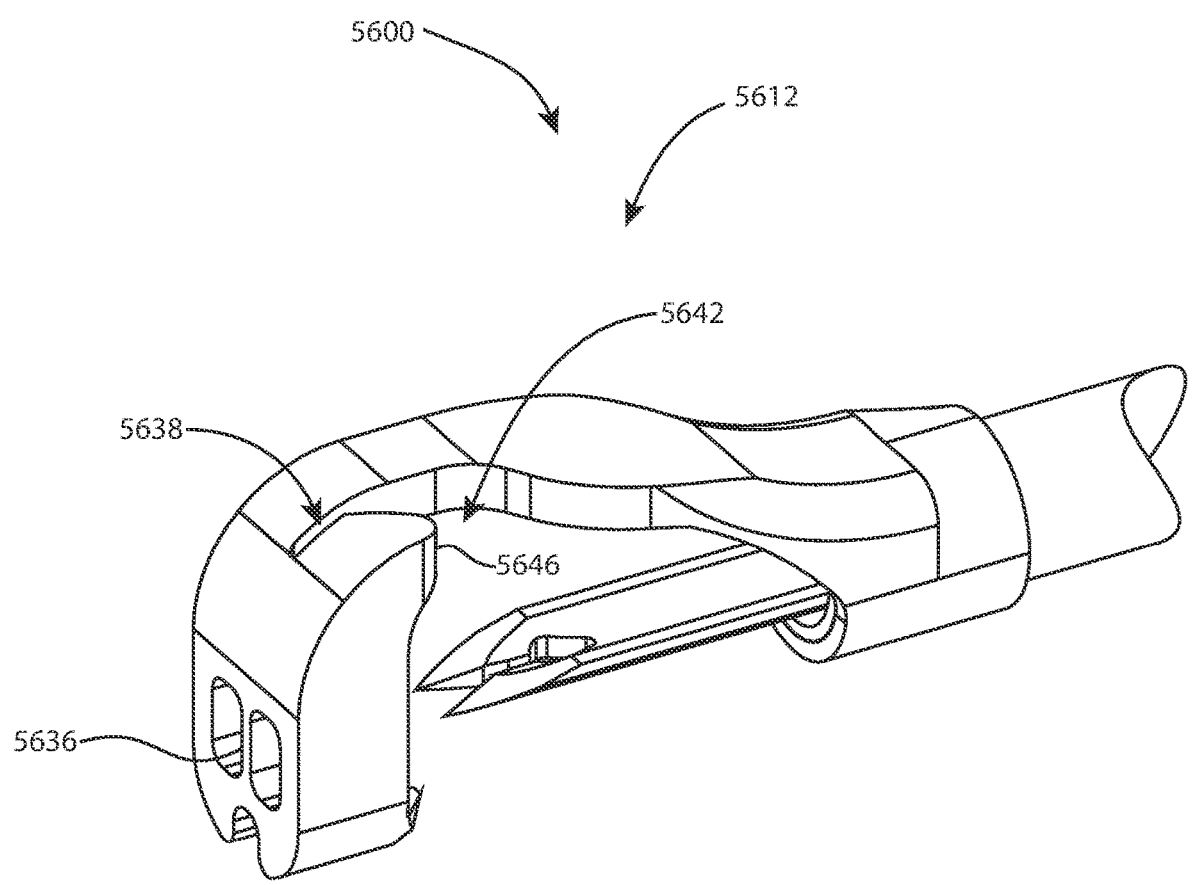
FIG. 58 is yet another perspective view of the distal tip portion of the suture passer of FIG. 56, from another different viewpoint.

The presently preferred embodiments of the present invention will be best understood by reference to the drawings, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the apparatus, system, and method of the present invention, as represented in FIGS. 1 through 58, is not intended to limit the scope of the invention, as claimed, but is merely representative of presently preferred embodiments of the invention.

Figure 1:
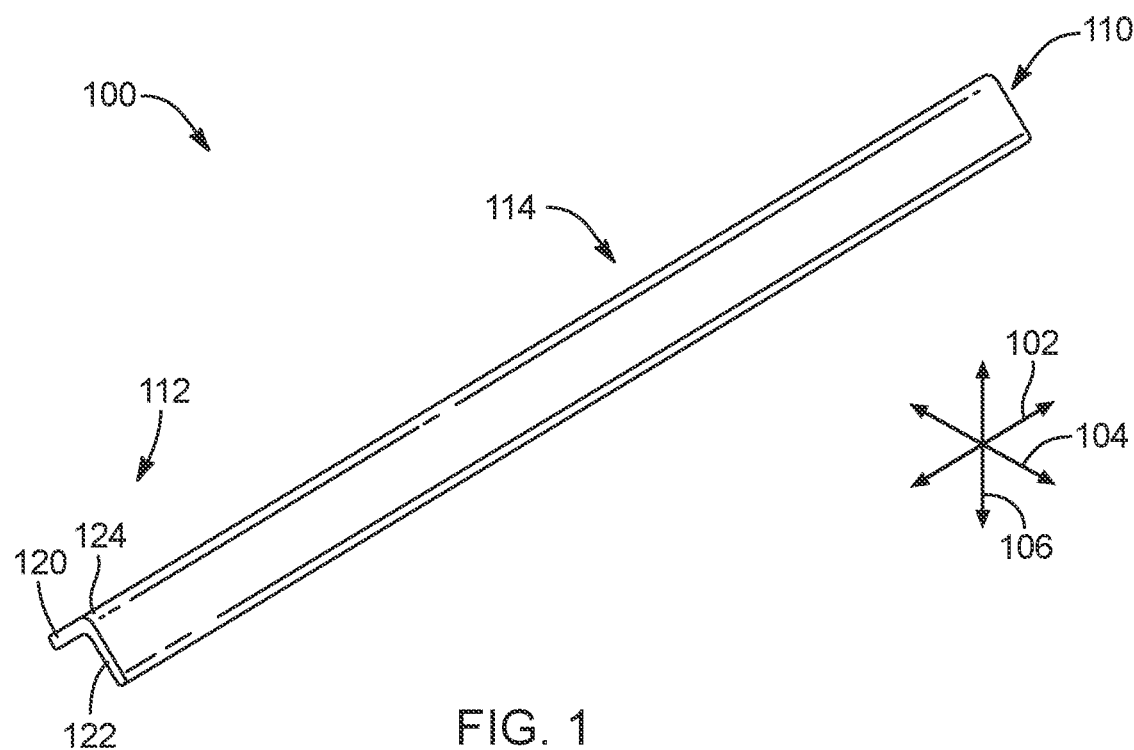
FIG. 1 is a perspective view of a rigid V-shaped pusher.

Referring to FIG. 1, a perspective view illustrates an implant manipulator 100 according to one embodiment of the invention. The implant manipulator 100 of FIG. 1 may take the form of a pusher 100 designed to push a surgical implant (not shown) into a desired location within the tissues of a body. Other implant manipulator types will be disclosed on connection with other figures. The pusher 100 may have a longitudinal direction 102, a lateral direction 104, and a transverse direction 106. The longitudinal direction 102 is parallel to the length, i.e., the long axis, of the pusher 100. The directions 104, 106 are orthogonal to it.

The pusher 100 may have a proximal end 110, distal end 112, and an intermediate portion 114 that extends between the proximal and distal ends 110, 112. Each end 110, 112 of the pusher 100 may take on a blunt or flat profile. Alternatively, the proximal end 110 may have a gripping interface (not shown) such as a handle or the like, and/or the distal end 112 may have an implant interface (not shown) designed to retain an implant until it has reached its desired location. The pusher 100 may be used to place an implant within a body, reposition an implant within a body, and/or remove an implant from the body.

The cross-sectional shape of the pusher 100 may be generally V-shaped. As best seen at the distal end 112 in FIG. 1, the cross-sectional shape may have a first arm 120, a second arm 122, and a spine 124. The first and second arms 120, 122 may be connected to the spine 124, and as illustrated in FIG. 1, they may be unitarily formed with the spine. The cross-sectional shape may be uniform along the entire length of the pusher 100. The first and second arms 120, 122 may extend from the spine 124 to define a perpendicular or near-perpendicular angle between the first and second arms 120, 122.

This cross-sectional shape, including the dimensions of its various parts, may result in a structure that has a high "flexural rigidity" relative to bending perpendicular to its long axis, as compared with other cross-sectional shapes such as rectangular or round profiles of similar material volume. Beneficially, the implant manipulator 100 has a relatively low profile. The "profile" of a medical instrument generally refers to the amount of tissue it must displace as it moves through the body. Tissue displacement leads to post-operative discomfort or pain and lengthens recovery time; hence, it is desirable for medical instruments to be "low profile." The profile of an instrument is generally proportional to the area of the cross-sectional shape that must penetrate the tissue; in the case of a hollow cross-sectional shape such as a tube, the profile is generally proportional to the area of the shape plus the area of the interior space within the shape.

An implant manipulator like the pusher 100 may optionally be actuated by an actuator (not shown) that helps to control its motion. Such an actuator may take a variety of forms, including a suture passer, a meniscal repair device, a bone anchor placement instrument, or the like. The pusher 100 may be any instrument that moves a surgical implant to or from a desired location in a body, and the actuator may thus be any instrument that moves the implant manipulator to facilitate such motion. The actuator may be held by a user, a robotic surgical assembly, or a stationary framework, and may move the implant manipulator through manual control with or without intervening mechanical components. Alternatively, such an actuator may use electric motors or other motion sources to move the implant manipulator.

Figure 2A:
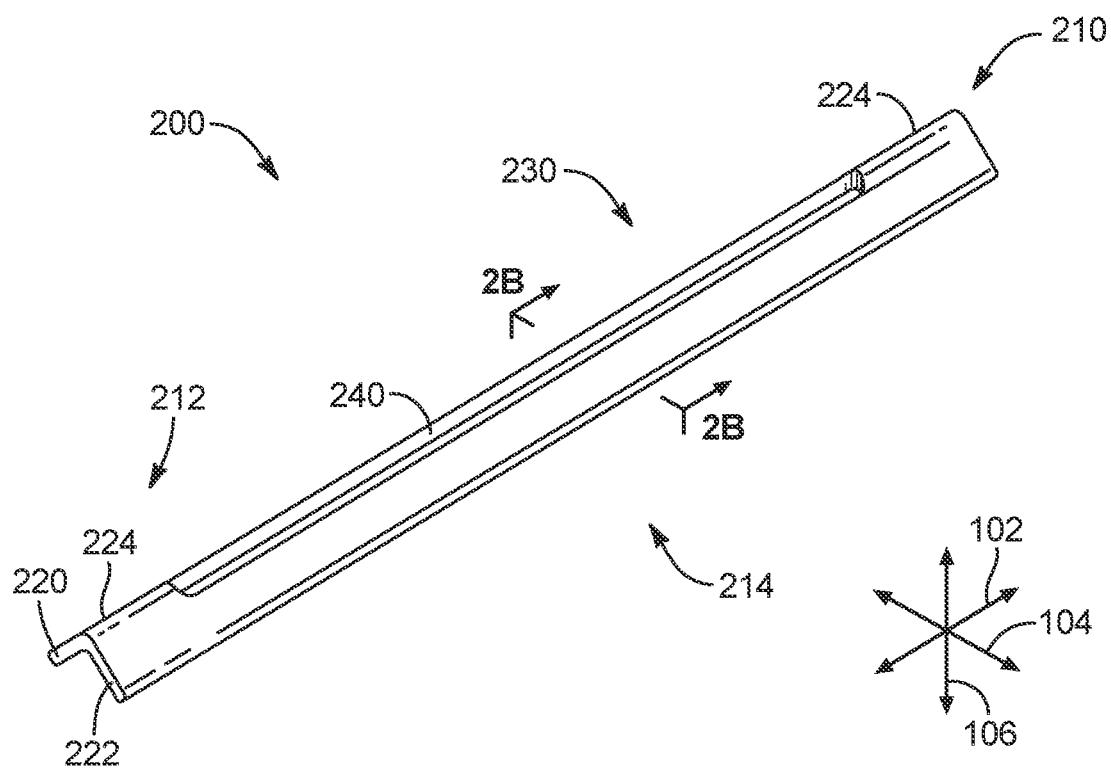
FIG. 2A is a perspective view of a pusher with a central slot to add flexibility.

Referring to FIG. 2A, a perspective view illustrates an implant manipulator 200 according to an alternative embodiment of the invention. The implant manipulator 200 may also be a pusher 200. The pusher 200 may be flexible; i.e., designed to bend in a direction perpendicular to its long axis. Such bending may allow the pusher 200 to deflect, for example, subcutaneously, to reach a target area along a non-linear subcutaneous pathway. If desired, the pusher 200 may be made of a superelastic material, i.e., a material designed to undergo relatively large elastic deformation, and then return to its original shape. Further, the pusher 200 may be formed of a shape memory alloy or the like. According to one example, the pusher 200 (and other implant manipulators embodied herein) may be made of Nitinol.

Like the pusher 100, the pusher 200 may have a proximal end 210, a distal end 212, and an intermediate portion 214. At the distal end 212, the pusher 100 has a cross-sectional shape with a first arm 220 and a second arm 222, both of which are connected to a spine 224. The pusher 200 may have the same cross-sectional shape at the proximal end 210. However, the pusher 200 may have an intermediate portion 214 that is different from the intermediate portion 114 because the intermediate portion 214 may have a selectively bendable portion 230 at which the intermediate portion 214 is designed to bend. The selectively bendable portion 230 may be configured such that, in a first configuration, the selectively bendable portion 230 is substantially rigid, while in a second configuration, the selectively bendable portion 230 is able to bend more freely. "Selective" bending refers to deliberate, controllable bending, as opposed to bending that simply occurs as an unintended consequence of the use of an instrument.

This configuration change may occur in many different ways. Some materials are known to change elasticity when raised or lowered beyond certain transition temperatures. Alternatively, stiffening members (not shown) may be inserted into engagement with a needle along the needle axis to provide stiffening where, and when, it is desired. All such configuration changes fall within the scope of the present invention. However, in the embodiment of FIG. 2A, selective bending is carried out by changing the cross-sectional shape of the selectively bendable portion 230. More precisely, an object with a given cross-sectional shape and material composition will have a given "flexural rigidity," or resistance to bending. Generally, positioning material further from the geometric center of a cross-sectional shape will increase its flexural rigidity, at least as applied to bending parallel to the direction in which it is displaced from the geometric center. Thus, a tube made of a given material will tend to resist bending more effectively in all directions perpendicular to the tube axis than a cylinder made from the same material, with the same length.

The pusher 200 uses this principle to obtain additional stiffness when desired, and also to exhibit additional flexure when desired. In surgical applications, this is useful in a wide variety of contexts because it is very common to access a desired location within a body (such as a human body) along a nonlinear pathway, for example, to get around intervening bones or sensitive tissues, or to provide a desired angle of approach to the desired location. The nonlinear pathway may require that instruments bend to reach the desired location. However, it may be desirable for the instruments to retain significant stiffness to enable them to perform their intended functions at the desired location.

One example of an instrument that may need to move along a non-linear pathway is a needle for a suture passer. Such needles commonly are used to puncture tissue and either push or pull suture through the puncture along a direction nonparallel to the axis of the instrument. Unfortunately, prior art suture passers tend to exhibit a variety of problems related to the stiffness of the needle. A needle with the flexibility required to navigate the nonlinear pathway may not have sufficient rigidity to puncture the tissue without skiving against the tissue or otherwise deflecting from its intended approach vector.

The pusher 200 remedies these shortcomings through variation of the cross-sectional shape of the selectively bendable portion 230. The selectively bendable portion 230 has a cross-sectional shape designed to permit selective flexure of the selectively bendable portion 230. More precisely, the pusher 200 may have a slot 240 that interrupts the spine 224 along a given length of the intermediate portion 214 such that the spine 224 exists proximate the proximal and distal ends 210, 212, but the slot 240 is instead present in the selectively bendable portion 230. The slot 240 may be cut or otherwise removed from a full-length spine like the spine 124 of FIG. 1, or the pusher 200 may be formed with the spine 224 and the slot 240 in place.

The slot 240 permits the selectively bendable portion 230 to be re-configured during use by changing its cross-sectional shape to control its flexural rigidity, particularly as applied to bending along the lateral direction 104 and the transverse direction 106. The selectively bendable portion 230 may have one flexural rigidity that applies to bending in the lateral direction 104, and a different flexural rigidity that applies to bending in the transverse direction 106.

The cross-sectional shape of the pusher 100 of FIG. 1 may be designed to restrict flexure of the pusher 100. The slot 240 may effectively remove the spine 224 from the cross-sectional shape of the selectively bendable portion 230, thereby allowing the arms 220, 222 to bend, rotate, or deform in a manner that resembles the flexure that would be obtained if they were individual thin, flat, rectangular sections of material. Thus, the selectively bendable portion 230 may provide the flexibility to allow the pusher 200 to bend as shown in the examples in FIGS. 8 and 9. This concept will be shown and described in connection with FIGS. 2B-2D.

Figure 2B:
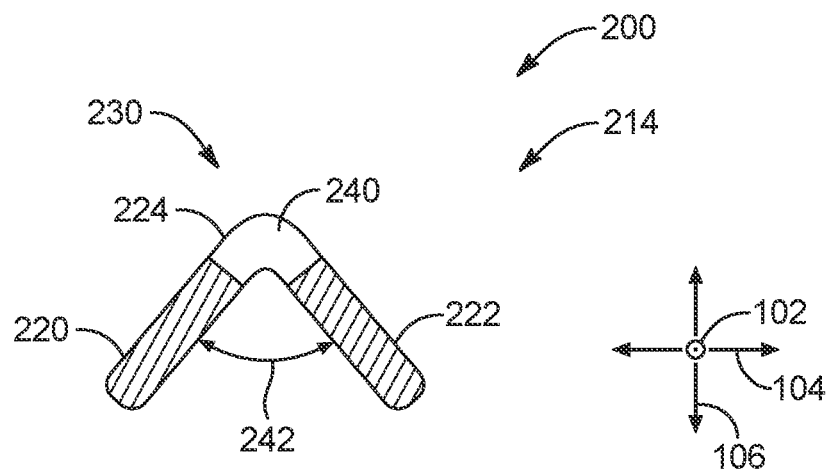
FIG. 2B is a section view from along the length of the pusher of FIG. 2A, with the selectively bendable portion having a first cross-sectional shape selected to restrict bending perpendicular to its longitudinal length.

Referring to FIG. 2B, a section view perpendicular to the longitudinal direction 102 illustrates the cross-sectional shape of the selectively bendable portion 230 as configured in FIG. 2A. The selectively bendable portion 230 is configured to resist bending in the lateral and transverse directions 104, 106. The arms 220, 222 are positioned at an angle 242 relative to each other; this angle 242 may be near 90°. In alternative embodiments, in the rest (i.e., substantially undeflected) configuration, the arms 220, 222 may be angled relative to each other at other angles, such as 60° or 120°, or angles in between, as will be shown and described subsequently.

As mentioned previously, the flexural rigidity of a shape is generally proportional to the distance of the material from the center of a shape. Thus, a long, flat cross-sectional shape would tend to allow easy bending perpendicular to the length of the cross-sectional shape, but resist bending parallel to the length of the cross-sectional shape. Each of the arms 220, 222 provides a relatively long, flat cross-sectional shape, but since they are orthogonal to each other, the cross-sectional shape of FIG. 2B is not generally parallel to any direction. Thus, the flexural rigidity is relatively high for any bending direction perpendicular to the longitudinal direction 102 (i.e., the lateral direction 104, the transverse direction 106, or any direction that is a vector with lateral and longitudinal components).

Figure 2C:
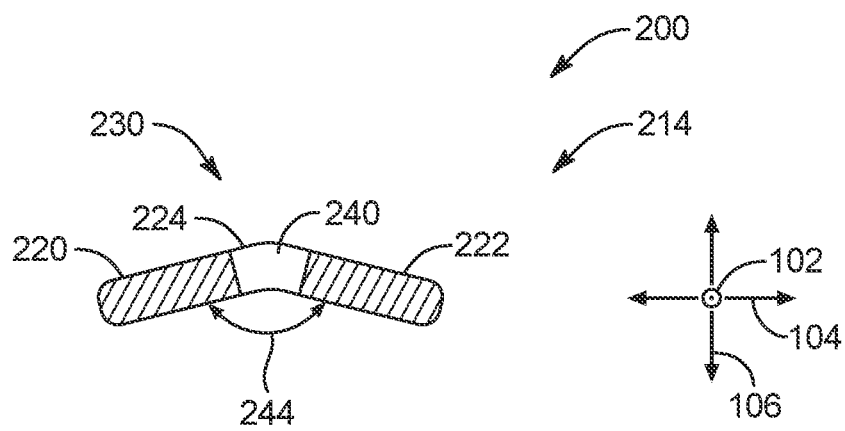
FIG. 2C is a section view from along the length of the pusher of FIG. 2A, with the selectively bendable portion having a second cross-sectional shape selected to facilitate bending in the transverse direction.

Referring to FIG. 2C, a section view perpendicular to the longitudinal direction 102 illustrates the cross-sectional shape of the selectively bendable portion 230 with the selectively bendable portion 230 configured to resist bending in the lateral direction 104, but permit bending relatively easily in the transverse direction 106. The arms 220, 222 are generally coplanar to each other. Accordingly, they are oriented at an angle 244 relative to each other of approximately 180°. As shown, the angle 244 need not be exactly 180° to facilitate bending in the transverse direction 106. The angle 244 may, for example, be 150°, 160°, 170°, 175°, or 180°. Depending on the nature of the force that moves the cross-sectional shape into the configuration shown in FIG. 2C, the angle 244 may even be larger than 180°.

Figure 2D:
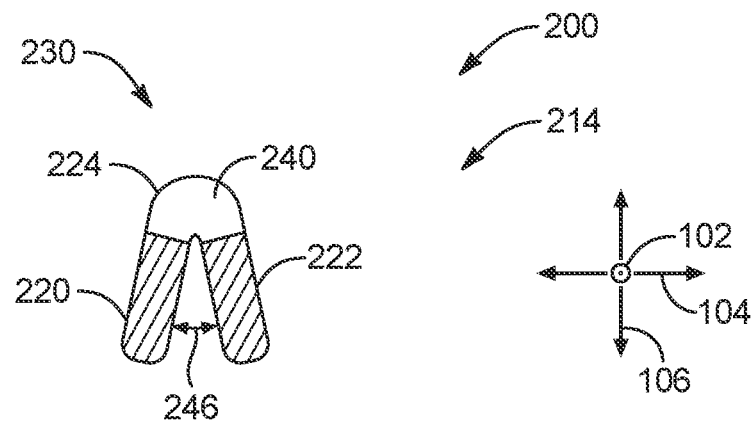
FIG. 2D is a section view from along the length of the pusher of FIG. 2A, with the selectively bendable portion having a third cross-sectional shape selected to facilitate bending in the lateral direction.

Referring to FIG. 2D, a section view perpendicular to the longitudinal direction 102 illustrates the cross-sectional shape of the selectively bendable portion 230 with the selectively bendable portion 230 configured to resist bending in the transverse direction 106, but permit bending relatively easily in the lateral direction 104. The arms 220, 222 are generally non-coplanar to each other, but they are generally parallel to each other. Accordingly, they are oriented at an angle 246 relative to each other of approximately 0°. As shown, the angle 246 need not be exactly 0° to facilitate bending in the lateral direction 104. The angle 246 may, for example, be 30°, 20°, 10°, 5°, or 0°.

As a variation of the pusher 200 shown in FIGS. 2A-2D, the slot 240 may fully extend through to the distal end 212 or the proximal end 210 of the pusher 200. At least one end 210 or 212 of the pusher 200 may advantageously maintain a length of the spine 224 so that the pusher 200 has rigidity at one end 210 or 212. Rigidity at the proximal end 210 may be beneficial if the pusher 200 is being pushed proximal to distal by an instrument, while rigidity at the distal end 212 may be beneficial if the pusher 200 is being pushed against an implant or other device that needs to be advanced.

As another alternative, a slot may be shaped differently from the slot 240 shown in FIG. 2A. In alternative embodiments (not shown), such a slot may follow a curved or jagged pathway. Multiple slots may be used, and may be parallel or co-linear and broken by intervening lengths of a spine. As yet another alternative, the feature that facilitates bending need not be a slot, but may simply be a notch extending along the length of the intermediate portion of the implant manipulator (not shown). Such a notch may act a as a "living hinge" or "flexural hinge" by providing enhanced flexure without extending fully through the material of the implant manipulator. As another alternative, an implant manipulator (not shown) may have an actual hinge, i.e., an interface between opposing sides that permits relative rotation between the two sides, thereby allowing the sides to collapse together and/or spread apart. As yet another alternative, an implant manipulator (not shown) may have a strip of a secondary material with lower flexural rigidity than the material of which the remainder of the implant manipulator is formed. All such alternatives are contemplated within the scope of the invention and may provide a cross-sectional change that restricts or facilitates bending of a selectively bendable portion, as desired.

Figure 3A:
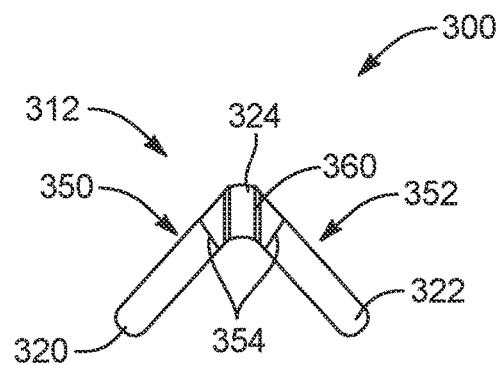
FIGS. 3A-3C are end, side and top views of a rigid needle with a suture capture feature at one end.
Figure 3B:
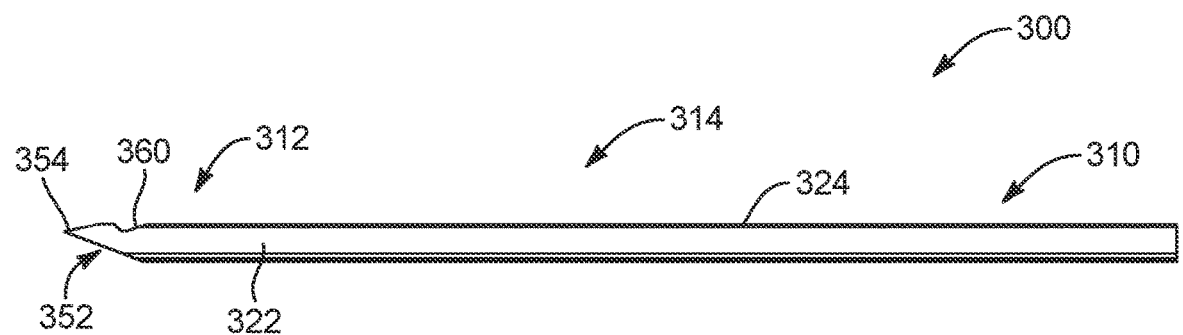
Figure 3C:
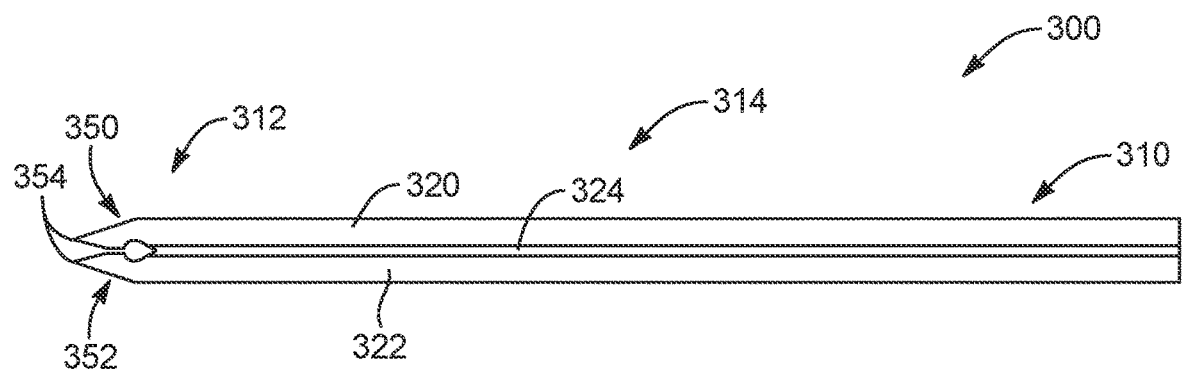

Referring to FIGS. 3A-3C, the pusher 100 in FIG. 1 may be modified as shown in FIGS. 3A-3C to take on the configuration of an implant manipulator 300 in the form of a needle 300. Like the pusher 100, the needle 300 may be generally rigid, and may have a proximal end 310, a distal end 312, and an intermediate portion 314. The needle 300 may have the same V-shaped cross-sectional shape as the pusher 100. Thus, the needle 300 may have a cross-sectional shape with a first arm 320, a second arm 322, and a spine 324. The distal end 312 may be designed to penetrate tissue.

More specifically, the distal end 312 may have a sharpened tip such that it can be easily passed through tissue with minimal resistance to reduce any trauma to the body. As shown in FIGS. 3A-3C, the distal end 312 may have a first member 350 and a second member 352, each of which has a sharpened tip 354. The distal end 312 may also have an implant interface 360 designed to move an implant within the body in a desired manner. An "implant interface" includes any feature that abuts an implant (i.e., contacts the implant) in order to guide the implant in some manner. Thus, an implant interface may retain an implant, or it may simply push or otherwise drive it to the desired location. The desired location may be an implantation location within the body, or in the case of an implant to be removed, a location outside the body.

In the embodiment of FIGS. 3A-3C, the implant interface 360 may take the form of a suture capture feature 360. A suture capture feature includes any feature that retains a length of suture to enable the length of suture to be moved. Thus, in this configuration, the needle 300 may be used to penetrate through a section of tissue, capture a section of suture material in the suture capture feature 360, and then retrieve the suture material back through the tissue via withdrawal of the needle 300. This can be beneficial when it is necessary to pass suture through tissue in a controlled manner without multiple instruments or features required for passing and retrieving the suture. The operation of the suture capture feature 360 will be shown and described in greater detail in connection with FIG. 7A.

Figure 4A:
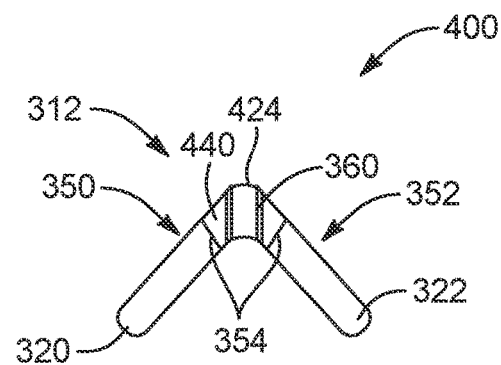
FIGS. 4A-4C are end, side and top views of a needle with a central slot through the middle and a suture capture feature at one end.
Figure 4B:
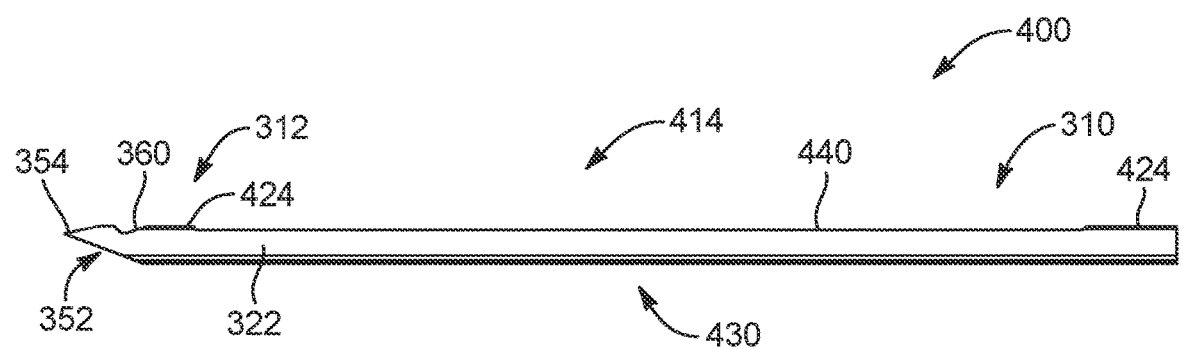
Figure 4C:
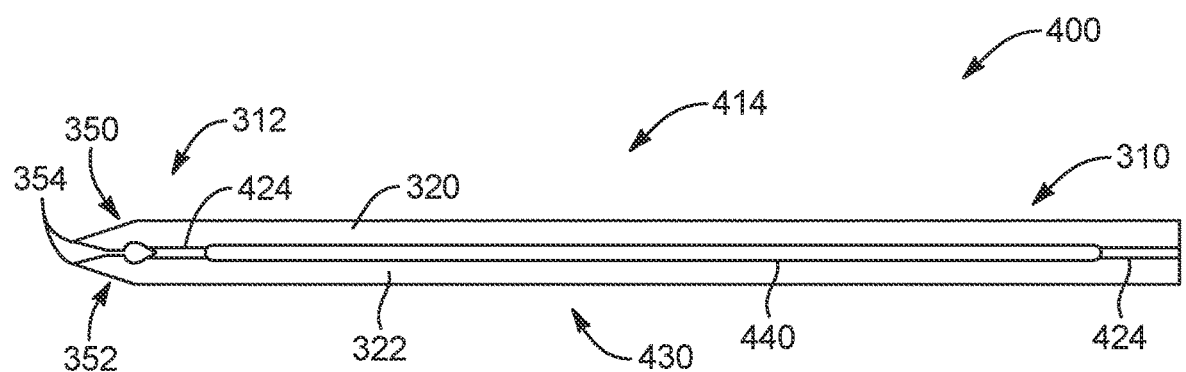

Referring to FIGS. 4A-4C, the needle 300 of FIGS. 3A-3C, may be further modified to provide an implant manipulator 400 according to another embodiment of the invention. The implant manipulator 400 may take the form of a needle 400 with features that are generally similar to those of the needle 300. However, the needle 400 may have an intermediate portion 414 that is different from the intermediate portion 314 because the intermediate portion 414 may have a selectively bendable portion 430 at which the intermediate portion 414 is designed to bend. The selectively bendable portion 430 may be configured such that, in a first configuration, the selectively bendable portion 430 is substantially rigid, while in a second configuration, the selectively bendable portion 430 is able to bend more freely. More precisely, the spine 424 of the needle 400 may be interrupted by a slot 440 that generally traverses the intermediate portion 414 in a manner similar to that of the slot 240 of FIGS. 2A-2D. The slot 440 may enable the cross-sectional shape of the selectively bendable portion 430 to vary as in FIGS. 2B-2D to selectively facilitate bending parallel to the lateral direction 104 and/or the transverse direction 106.

As with the pusher 200 of FIGS. 2A-2D, the needle 400 may be configured in a wide variety of ways. Such variations include variations of the slot 240 and other features used in place of the slot to provide cross-sectional change.

Advantageously, implant manipulators according to some embodiments of the invention may have a cross-sectional shape, perpendicular to the length of the implant manipulator that extends along a nonlinear pathway. A shape that extends along a pathway has a relatively consistent width perpendicular to a linear or nonlinear form embedded within the shape such that the form defines a pathway. The pathway extends through the center of the shape to bisect the width at each point along its length. A shape that extends along a pathway need not have a precisely constant width perpendicular to the pathway; rather, some variation is to be expected, particularly at the end points and any tight turns in the pathway.

In one example, a cross-sectional shape may have a width that never exceeds 200% of its average width perpendicular to the pathway. According to another example, a cross-sectional shape may have a width that never exceeds 150% of its average width perpendicular to the pathway. According to yet another example, a cross-sectional shape may have a width that never exceeds 125% of its average width perpendicular to the pathway.

"Nonlinear" refers to a shape, at least part of which is not a straight line. Thus, a nonlinear shape may have a straight portion and a portion with a curve, vertex, or other departure from the straight line. These concepts will be shown and described in connection with FIGS. 5A and 5B.

Referring to FIGS. 5A and 5B, end views illustrate some of the cross-sectional shapes that may be used for an implant manipulator. More precisely, FIG. 5A illustrates an implant manipulator 500 having a V-shaped cross-sectional shape similar to the implant manipulators of FIGS. 1-4C. The implant manipulator 500 may have a first arm 520 and a second arm 522. The first arm 520 and the second arm 522 may be connected together via a spine 524. The result may be a V-shape, which is upside-down in FIG. 5A.

A "V-shape" includes any shape with only two arms that join to define a vertex (or region with a small radius of curvature defining a near-vertex), leaving an open space, such as the space 526, between the arms with unrestricted access to the space from outside the cross-sectional shape. Thus, if the first arm 520 and second arm 522 were modified such that they curve or angle toward each other on the opposite side of the space 526 from the spine 524, the resulting cross-sectional shape (not shown) would not be a V-shape, but may instead be a C-shape (if the arms do not connect together) or an O-shape (if the arms do connect together). The arms of a V-shaped cross-sectional shape may be straight or curved. Additionally, the angle at the vertex need not be a right angle, as shown in FIG. 5A, but may be any of a wide variety of angles that will be shown and described in connection with FIGS. 6A-6C.

More particularly, the cross-sectional shape of the selectively bendable portion 530 (FIG. 6B) may extend along a nonlinear pathway 532. As shown, the nonlinear pathway 532 extends from the outermost tip of the first arm 520 to the outermost tip of the second arm 522. The nonlinear pathway 532 defines a pathway within the definition provided above because the cross-sectional shape of the selectively bendable portion 530 has a relatively consistent width perpendicular to the nonlinear pathway 532.

The nonlinear pathway 532 has a width 534 within the main portion of the first arm 520 and the second arm 522. The nonlinear pathway 532 also has a width 536 across the spine 524. Additionally, the nonlinear pathway 532 has a width 538 toward the outermost ends of the first arm 520 and the second arm 522. The width 536 may be larger than the width 534, and the width 534 may be larger than the width 538, which tapers to zero at the ends of the nonlinear pathway 532. However, the width of the cross-sectional shape is still relatively consistent along the length of the nonlinear pathway 532 despite these differences. In other embodiments (not shown), one or more of the first arm 520, the second arm 522, and the spine 524 may have a taper, a bump, recess, or other irregularity; such irregularities may change the shape of the nonlinear pathway 532, but unless they are extreme, they do not keep the cross-sectional shape from being one that follows a pathway.

The nonlinear pathway 532 has linear segments within the first arm 520 and the second arm 522, but has a small radius of curvature (e.g., a near-vertex as described above) through the spine 524. Thus, the nonlinear pathway 532 is nonlinear and is also V-shaped within the definition provided above. In alternative embodiments, a nonlinear pathway like the nonlinear pathway 532 may be broken by one or more features such as the slot 240 of FIGS. 2A-2D. A "break" in a pathway may be defined as a location at which the material at the pathway is interrupted, but the pathway is still readily discernible. For example, the cross-section shown in FIG. 2B still presents a readily discernible V-shaped nonlinear pathway, despite the presence of the break defined by the intersection of the slot 240 with the cross-sectional shape.

In operation, the implant manipulator 500 may function in the manner illustrated in FIGS. 2B-2D. The V-shape may bend at or near the spine 524 to bring the first arm 520 and the second arm 522 close to a coplanar condition as in FIG. 2C, or may bend the other way to bring the first arm 520 and the second arm 522 close to a parallel condition as in FIG. 2D. Thus, the V-shape may be altered to facilitate or restrict bending as desired.

Referring to FIG. 5B, an end view illustrates an implant manipulator 550 according to one alternative embodiment of the invention. The implant manipulator 550 may have an arcuate or U-shaped cross-sectional shape. More precisely, the implant manipulator 550 may have a first arm 570 and a second arm 572 that are connected together via a spine 574. The first arm 570 and the second arm 572 are both curved, and share the same radius of curvature 590. The spine 574 does not form a vertex like the spine 524 of FIG. 5A, but rather represents a continuous transition between the first arm 570 and the second arm 572. In FIG. 5B, the spine 574 preserves the radius of curvature of the first arm 570 and the second arm 572, although this need not be the case with other U-shaped cross-sectional shapes.

Generally, a "U-shape" includes any shape with only two arms that join at a radius to define a round in place of the vertex of a V-shape, leaving an open space, such as the space 576, between the arms with unrestricted access to the space from outside the cross-sectional shape. A U-shape may have arms that are straight or curved.

The cross-sectional shape of the selectively bendable portion 580 may extend along a nonlinear pathway 582. As shown, the nonlinear pathway 582 extends from the outermost tip of the first arm 570 to the outermost tip of the second arm 572. The nonlinear pathway 582 defines a pathway within the definition provided above because the cross-sectional shape of the selectively bendable portion 580 has a relatively consistent width perpendicular to the nonlinear pathway 582.

The nonlinear pathway 582 has a width 584 within the main portion of the first arm 570, the second arm 572, and the spine 574. Additionally, the nonlinear pathway 582 has a width 588 toward the outermost ends of the first arm 570 and the second arm 572. The width 584 may be larger than the width 588, which tapers to zero at the ends of the nonlinear pathway 582. However, the width of the cross-sectional shape is still relatively consistent along the length of the nonlinear pathway 582 despite these differences. In other embodiments (not shown), one or more of the first arm 570, the second arm 572, and the spine 574 may have a taper, a bump, recess, or other irregularity; such irregularities may change the shape of the nonlinear pathway 582, but unless they are extreme, they do not keep the cross-sectional shape from being one that follows a pathway.

The nonlinear pathway 582 has no linear segments, but rather has a constant radius of curvature 590 through the first arm 570, the second arm 572, and the spine 574. The first arm 570 and the second arm 572 join at the spine, 574, and all of them share the same radius of curvature 590. Since the spine 574 has a relatively large radius, the nonlinear pathway 582 is nonlinear and is also U-shaped within the definition provided above.

In operation, the implant manipulator 550 may function in a manner somewhat similar to that of FIGS. 2B-2D. More precisely, as shown in FIG. 5B, the implant manipulator 550 may generally resist bending along the lateral direction 104 or the transverse direction 106 because the cross-sectional shape in FIG. 5B has significant mass displaced from its geometric center along both directions. However, if the first arm 570 and the second arm 572 were to be splayed outward so that the radius of curvature 590 is effectively increased (analogous to FIG. 2C), the flexural rigidity of the implant manipulator 550 with reference to bending along the transverse direction 106 would be effectively decreased, while the flexural rigidity for bending along the lateral direction 104 would be increased. If desired, the cross-sectional shape of the implant manipulator 550 may even flex sufficiently that the nonlinear pathway 582 extends in a substantially straight line.

If the first arm 570 and the second arm 572 were to be urged together so that the radius of curvature 590 is effectively decreased (analogous to FIG. 2D), the flexural rigidity of the implant manipulator 550 with reference to bending along the lateral direction 104 would be effectively decreased, while flexural rigidity for bending along the transverse direction 106 would be decreased. If desired, the cross-sectional shape of the implant manipulator 550 may flex such that the radius of curvature 590 becomes variable along the length of the nonlinear pathway 582. For example, the spine 574 may experience greater deflection than the second arm 572 and the spine 574 so that, at the spine 574, the radius of curvature is smaller than at the first arm 570 and the second arm 572. If desired, the cross-sectional shape of the implant manipulator 550 may vary sufficiently that the ends of first arm 570 and the second arm 572 come into contact with each other.

In alternative embodiments (not shown), an implant manipulator may have a U-shaped cross-sectional shape like the implant manipulator 550 of FIG. 5B in combination with other features disclosed in connection with other embodiments herein. For example, such an implant manipulator may have a slot like the slot 240 of FIGS. 2A-2D, an implant interface 360 like that of FIGS. 3A-3C, or the like. Alternatively, such an implant manipulator may have other features that facilitate change of its cross-sectional shape. For example, such an implant manipulator may have a differently-shaped slot, a groove or other recess that does not extend fully through its spine, a region of more flexible material (for example, at the spine), or any other change disclosed elsewhere in this specification.

Figure 5C:
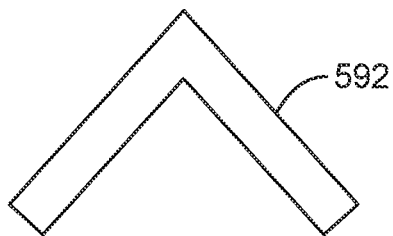

Referring to FIG. 5C, an end view illustrates an implant manipulator 592 according to another embodiment of the invention. The implant manipulator 592 may be similar to the implant manipulator 500 of FIG. 5A, except that the corners and edges of the implant manipulator 592 are squared rather than rounded. Such squared edges may facilitate tissue puncturing and/or penetration. The use of squared or rounded edges may depend on the desired tissue penetration characteristics of the implant manipulator.

Figure 5D:
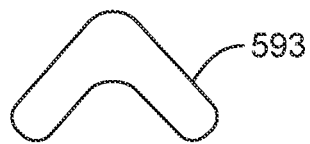

Referring to FIG. 5D, an end view illustrates an implant manipulator 593 according to another alternative embodiment of the invention. The implant manipulator 593 may be similar to that of FIG. 5A, but with shorter arms. The arms of an implant manipulator may be shortened or lengthened to obtain the desired bending and/or tissue penetration characteristics.

Figure 5E:
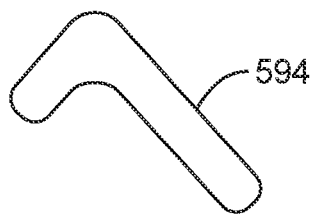

Referring to FIG. 5E, an end view illustrates an implant manipulator 594 according to another alternative embodiment of the invention. The implant manipulator 594 may be similar to that of FIG. 5A, but with arms of unequal length. Such a configuration may further provide a desired set of bending and/or tissue penetration characteristics.

Figure 5F:
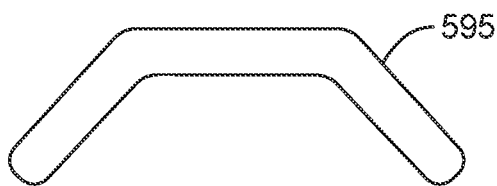

Referring to FIG. 5F, an end view illustrates an implant manipulator 595 according to another alternative embodiment of the invention. The implant manipulator 595 may have an elongated spine between shorter arms. The arms and/or spine may flex to selectively restrict or facilitate bending. Such a configuration may further provide a desired set of bending and/or tissue penetration characteristics.

Figure 5G:
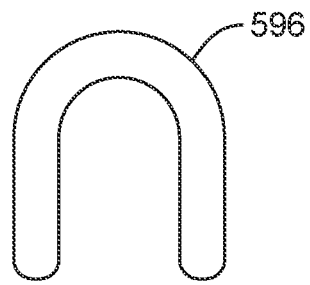

Referring to FIG. 5G, an end view illustrates an implant manipulator 596 according to another alternative embodiment of the invention. The implant manipulator 596 may have a spine with a relatively large radius of curvature, with arms that extend from the spine generally parallel to each other. Like the spine 574 of the implant manipulator 550 of FIG. 5B, the spine of the implant manipulator 596 may flex via variation of its center of curvature. The result of such flexure may be alteration of the relative orientations of the arms, thereby selectively facilitating or restricting bending.

Figure 5H:
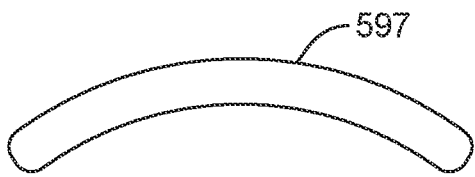

Referring to FIG. 5H, an end view illustrates an implant manipulator 597 according to another alternative embodiment of the invention. The implant manipulator 597 may be similar to the implant manipulator 550 of FIG. 5B, but with a larger radius of curvature. Such a configuration may further provide a desired set of bending and/or tissue penetration characteristics.

The V-shaped nonlinear pathway 532 and the U-shaped nonlinear pathway 582 of FIGS. 5A and 5B, and the nonlinear pathways of FIGS. 5C-5H are merely exemplary; a wide variety of alternative cross-sectional shapes may be used within the scope of the present invention. For example, in alternative embodiments (not shown), a selectively flexible portion of an implant manipulator may have a C-shaped, D-shaped, H-shaped, I-shaped, J-shaped, K-shaped, L-shaped, M-shaped, N-shaped, O-shaped, S-shaped, T-shaped, W-shaped, X-shaped, Y-shaped, or Z-shaped cross-section extending along the corresponding nonlinear pathway. Such cross-sectional shapes may also be variable between different configurations to provide a selectively bendable portion, the flexural rigidity of which can be controlled through variation of the cross-sectional shape.

Referring to FIGS. 6A-6C, end views illustrate how the angulation of the V-shaped cross-section can vary to alter the stiffness and profile of the device. More specifically, FIG. 6A illustrates an implant manipulator 600 according to one alternative embodiment, FIG. 6B illustrates the implant manipulator 500 of FIG. 5A, and FIG. 6C illustrates an implant manipulator 650 according to another alternative embodiment of the invention.

Referring to FIG. 6A, an end view illustrates the implant manipulator 600. The implant manipulator 600 may have a first arm 620 and a second arm 622 that are joined at a spine 624 to define a V-shaped cross-sectional shape, as described in connection with FIG. 5A. The implant manipulator 600 may have a selectively bendable portion 630 having the cross-sectional shape shown in FIG. 6A. In its generally unaltered (i.e., undeflected) state, the cross-sectional shape may have an angle 640 between the first arm 620 and the second arm 622. As shown in FIG. 6A, the angle 640 may be an obtuse angle, i.e., an angle greater than 90°. The angle 640 may fall within the range of 90° to 150°. More particularly, the angle 640 may fall within the range of 100° to 140°. Yet more particularly, the angle 640 may fall within the range of 110° to 130°. Still more particularly, the angle 640 may be 120°.

Referring to FIG. 6B, an end view illustrates the implant manipulator 500. The various features of the implant manipulator 500 are described in connection with FIG. 5A. As shown in FIG. 6B, the cross-sectional shape of the implant manipulator 500 may have an angle 540 between the first arm 520 and the second arm 522, in its unaltered state. The angle 540 may be a right angle, i.e., a 90° angle.

Referring to FIG. 6C, an end view illustrates the implant manipulator 650. The implant manipulator 650 may have a first arm 670 and a second arm 672 that are joined at a spine 674 to define a V-shaped cross-sectional shape, as described in connection with FIG. 5A. The implant manipulator 650 may have a selectively bendable portion 680 having the cross-sectional shape shown in FIG. 6C. In its unaltered state, the cross-sectional shape may have an angle 690 between the first arm 670 and the second arm 672. As shown in FIG. 6C, the angle 690 may be an acute angle, i.e., an angle less than 90°. The angle 690 may fall within the range of 30° to 90°. More particularly, the angle 690 may fall within the range of 40° to 80°. Yet more particularly, the angle 640 may fall within the range of 50° to 70°. Still more particularly, the angle 640 may be 60°.

The implant manipulator 500 generally has high flexural rigidity for bending along the lateral direction 104 or along the transverse direction 106. The larger angle 640 of the implant manipulator 600 provides greater flexural rigidity for bending along the lateral direction 104, but less flexural rigidity for bending along the transverse direction 106. Conversely, the smaller angle 690 of the implant manipulator 650 provides greater flexural rigidity for bending along the transverse direction 106, but less flexural rigidity for bending along the lateral direction 104. Thus, the angulation of arms in a V-shaped cross-section may be tailored meet the desired bending characteristics of the instrument. Additionally, the length of the arms may be altered to further alter the stiffness and profile of the instrument.

Figure 7A:
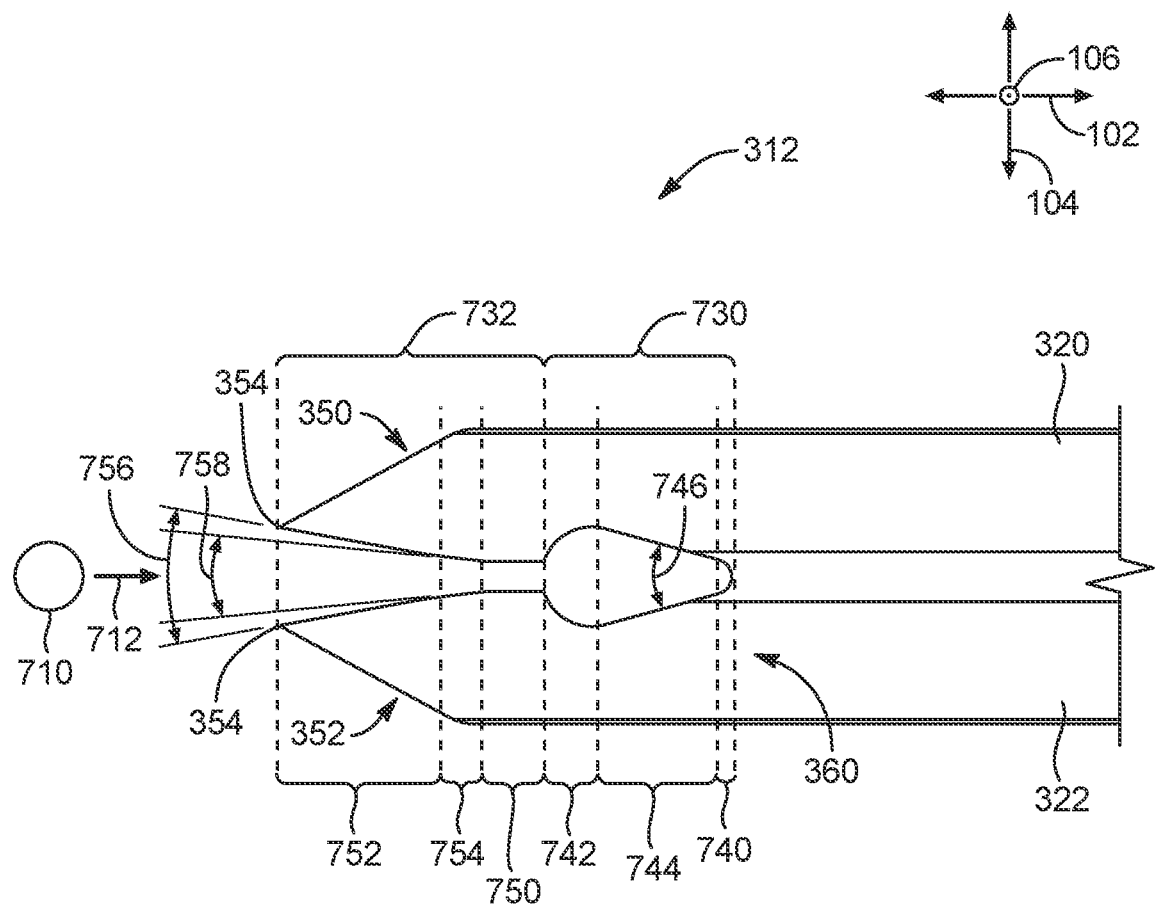
FIG. 7A is a top view of the distal end of the needle of FIGS. 3A-3C illustrating the suture capture feature of the needle in greater detail.

Referring to FIG. 7A, a top elevation view illustrates the distal end 312 of the implant manipulator 300 of FIGS. 3A-3C or the needle 400 of FIGS. 4A-4C in greater detail. The implant interface 360 may take the form of a suture capture feature 360 designed to retain suture 710 in response to relative motion by which the suture comes toward the distal end 312, as indicated by the arrow 712.

As in FIGS. 3A-3C and 4A-4D, the suture capture feature 360 may have a first member 350 and a second member 352, each of which has a tip 354. Each of the tips 354 may be sharp to enable the first member 350 and the second member 352 to puncture tissue with relative ease and little trauma. Thus, each of the tips 354 may be acutely-angled. The suture capture feature 360 also has a capture hole 730 shaped and sized to receive the suture, and a channel 732 that extends between the first member 350 and the second member 352 to provide access to the capture hole 730.

As shown, the capture hole 730 may have a proximal section 740, a distal section 742, and an intermediate section 744 between the proximal section 740 and the distal section 742. The distal section 742 may have a generally semicircular shape, broken by the channel 732, that widens toward the intermediate section 744. The diameter of the semicircular shape may be sized larger than the uncompressed diameter of the suture 710 the suture capture feature 360 is designed to retain. According to one embodiment, the suture capture feature 360 is made to capture a #2 suture 710 with an uncompressed outer diameter of about 0.40 mm. The semicircular shape of the distal section 742 may be sized to receive the suture 710 without compression so that the suture 710, when residing in the distal section 742, may be drawn through the distal section 742 along the transverse direction 106. According to one example, the diameter of the semicircular shape of the distal section 742 is about 0.76 mm. In alternative embodiments, this diameter ranges from 0.50 mm to 1.00 mm, or more particularly from 0.60 mm to 0.90 mm, or yet more particularly from 0.70 mm to 0.80 mm.

The proximal section 740 may also have a generally semicircular shape that widens toward the intermediate section 744. The diameter of the semicircular shape of the proximal section 740 may be smaller than the uncompressed diameter of the suture 710 so that the suture 710 can be wedged within the proximal section 740 by urging the suture 710 against the proximal section 740 in the direction shown by the arrow 712. Thus, the suture 710 may be firmly retained to restrict further relative motion between the suture 710 and the distal end 312 in any direction, and particularly, in the transverse direction 106. The extended length of the capture hole 730 may also increase the ability of the first arm 350 and the second arm 352 to flex outward relative to each other to widen the channel 732, thereby permitting passage of the suture 710 through the channel 732. According to one example, the diameter of the semicircular shape of the proximal section 740 is about 0.25 mm. In alternative embodiments, this diameter ranges from 0.05 mm to 0.45 mm, or more particularly from 0.15 mm to 0.35 mm, or yet more particularly from 0.20 mm to 0.30 mm.

The intermediate section 744 may have straight walls that define a taper angle 746 leading from the distal section 742 to the proximal section 740. The taper angle 746 may control how much force is needed to capture the suture 710 in the proximal section 740, and also controls the overall length of the capture hole 730. A more gentle taper angle 746 may enable capture with less force. According to one embodiment, the taper angle 746 may be about 30°. According to alternative embodiments, the taper angle 746 ranges from 10° to 50°, or more particularly, from 20° to 40°, or yet more particularly, from 25° to 35°.

In addition to controlling suture retention characteristics, the shape of the capture hole 730 may also control deflection of the first member 350 and the second member 352. The first member 350 and the second member 352 may deflect apart to enable the suture 710 to pass from a location distal to the distal end 312 into the capture hole 730. In the alternative, the distal end 312 may be rigid enough that there is no significant outboard flexure of the first member 350 and the second member 352. Thus, the suture 710 may simply deflect sufficiently to pass through the channel 732 without significant flexure of the suture capture feature 360.

In alternative embodiments, a capture hole may take on a number of different shapes. For example, including round, oval, rectangular, square, triangular, or any combination of these or other similar shapes may be used. The shape of the suture capture hole may be adapted to the desired retention characteristics of the suture capture hole, the type of suture to be used, the surrounding material available, and other factors.

The channel 732 may have a proximal section 750, a distal section 752, and an intermediate section 754. The suture 710 may enter through the distal section 752, pass through the intermediate section 754, and then pass through the proximal section 750 to enter the capture hole 730. Thus, the distal section 752 may advantageously be large enough to receive the suture 710 without precise alignment of the suture 710 with the axis of the distal end 312. This would allow for some variance or error in the trajectory that the distal end 312 takes towards the suture 710, post, and/or other features present on an associated instrument that facilitate spreading of the first member 350 and the second member 352, or that help urge motion of the suture 710 through the channel 732. The space between the tips 354 may advantageously not be so large as to adversely affect the ability of the needle to easily penetrate through tissue, or to cause unnecessary trauma to the tissue.

According to one example, the tips 354 of the first member 350 and the second member 352, when in their natural or undeflected state, may be about 0.76 mm apart when used with a #2 sized suture. This distance may be about twice the diameter of the suture used; this ratio may be used to properly dimension a distal end like the distal end 312 for a wide range of suture sizes. This distance may be the same as the width of the capture hole 730 in the lateral direction 104. In alternative embodiments, this displacement ranges from 0.50 mm to 1.00 mm, or more particularly from 0.60 mm to 0.90 mm, or yet more particularly from 0.70 mm to 0.80 mm.

The distal section 752 may taper toward the intermediate section 754 with a taper angle 756 that is large enough to guide the suture 710 from a variety of possible locations between the tips 354 to the intermediate section 754. According to one embodiment, the taper angle 756 may be about 20°. According to alternative embodiments, the taper angle 756 ranges from 5° to 35°, or more particularly, from 10° to 30°, or yet more particularly, from 15° to 25°.

The intermediate section 754 may also have a taper angle 758 which may be smaller (i.e., shallower) than the taper angle 756. The taper angle 758 may be selected such that, as the suture 710 passes through the intermediate section 754, the suture 710 pushes the walls of the intermediate section 754 apart to induce flexure in the distal end 312 to spread the first member 350 and the second member 352 apart. However, the suture 710 may lack the rigidity to flex the first member 350 and the second member 352 apart. Thus, according to one embodiment of the invention, the distal end 312 may be flexed by the introduction of a post into the channel 732. This will be shown in connection with FIGS. 22-28. The taper angle 758 additionally or alternatively may also be selected such that the suture 710 is compressed to the desired extent prior to entry into the proximal section 750. In the alternative, as mentioned previously, the first member 350 and the second member 352 may be designed such that they do not flex apart. In such an embodiment, a post may not need to be used.

The taper angle 758 may control how much force is needed to get the suture 710 and/or the post to pass through the intermediate section 754 and into the proximal section 750. A small or shallow taper angle 758 may facilitate entry of the suture 710 and/or post into the proximal section 750 but may require additional motion of the distal end 312 along the longitudinal direction 102 to position the suture 710 and/or post within the proximal section 750. Conversely, a steeper or larger taper angle 758 may increase the force, but reduce the displacement, required to position the suture 710 and/or post within the proximal section 750.

According to one example, the taper angle 758 may be about 10°. According to alternative embodiments, the taper angle 758 ranges from 2.5° to 17.5°, or more particularly, from 5° to 15°, or yet more particularly, from 7.5° to 12.5°.

The proximal section 750 may have walls that are substantially parallel to each other. The walls may be spaced apart such that the suture 710 must compress to pass through the proximal section 750, whether or not a post is used to cause flexure of the distal end 312. The walls may further be spaced apart such that, even with the first member 350 and the second member 352 flexed apart, the proximal section 750 remains too small to permit the suture 710 to pass through without compression of the suture 710. This may have the advantage of enabling the suture 710 to be captured against the corners defined by the intersection of the distal section 742 of the capture hole 730 with the proximal section 750 of the channel 732. However, in alternative embodiments, when flexed apart, the walls of the proximal section may be sufficiently spaced apart to permit the suture 710 to pass relatively freely through the proximal section, i.e., without significant compression of the suture 710. In other alternative embodiments, the walls of the proximal section may be sufficiently spaced apart to permit the suture 710 to pass relatively freely therethrough without flexure of the suture capture feature.

More specifically, once the suture 710 is positioned within the capture hole 730, the distal end 312 may be drawn proximally such that the suture 710 is pinched between the corners and/or compressed against the corners defined by the intersection of the distal section 742 of the capture hole 730 with the proximal section 750 of the channel 732. This pinching motion may restrict further motion of the suture 710 until it is pulled proximally toward the center of the capture hole 730. In particular, motion of the suture 710 in the transverse direction 106 may be restricted or prevented by this pinching motion. Thus, the suture 710 can be drawn through a hole in tissue or in an implant within the body as the distal end 312 is drawn proximally.

According to one example, where the suture 710 has an uncompressed diameter of 0.40 mm, the walls of the proximal section 750 may be spaced apart 0.25 mm. The walls of the proximal section 750 may be spaced apart by a distance equal to the diameter of the semicircular shape of the proximal section 740 of the capture hole 730. In alternative embodiments, the wall spacing ranges from 0.05 mm to 0.45 mm, or more particularly from 0.15 mm to 0.35 mm, or yet more particularly from 0.20 mm to 0.30 mm.

Various other dimensions of the exemplary embodiment of FIG. 7A will be provided, as follows. The longitudinal lengths of the proximal section 740, the distal section 742, and the intermediate section 744 of the capture hole 730 may be about 0.125 mm, about 0.38 mm, and about 0.94 mm, respectively. The longitudinal lengths of the proximal section 750, the distal section 752, and the intermediate section 754 of the channel 732 may be about 0.43 mm, about 1.27 mm, and about 0.35 mm, respectively. The distal end 312 may be 0.223 mm wide proximally of the first member 350 and the second member 352. These dimensions may be particularly applicable to the capture of the #2 suture referenced above; accordingly, all of the linear dimensions set forth herein may need to be increased or decreased if the suture to be captured is larger or smaller, respectively, than a #2 suture.

In operation, the distal end 312 may first be aligned with the suture 710 and/or post, at least so that the majority of the suture 710 and/or post is positioned inboard of the tips 354 of the first member 350 and the second member 352. The distal end 312 may then be advanced toward the suture 710 and/or post so that the suture 710 and/or post enters the distal section 752 of the channel 732. The distal end 312 may be further advanced so that the suture 710 and/or post passes into the intermediate section 754.

The distal end 312 may be further urged distally so that the suture 710 and/or post spreads the walls of the intermediate section 754 apart to cause the first member 350 and the second member 352 to move apart and/or compress the suture 710. The distal end 312 may be further urged distally so that the suture 710 and/or post enters the proximal section 750 of the channel 732. Further urging of the distal end 312 distally may cause the suture 710 and/or post to advance through the proximal section 750 of the channel 732, thereby driving the first member 350 and the second member 352 further apart and/or further compress the suture 710. Then, the suture 710 and/or post may enter the capture hole 730.

With the suture 710 in the capture hole 730, the distal end 312 may be urged proximally to pinch the suture 710 between the corners defined by the intersection of the distal section 742 of the capture hole 730 with the proximal section 750 of the channel 732. The distal end 312 may be further urged proximally until the distal end 312 is outside the body, where the suture 710 may be shifted back toward the center of the capture hole 730 and then moved along the transverse direction 106 to exit the capture hole 730.

Alternatively, with the suture 710 in the capture hole 730, the distal end 312 may be urged distally to pinch the suture 710 between the tapering walls of the intermediate section 744 and/or between the opposing sides of the proximal section 740 of the capture hole 730. The distal end 312 may then be urged proximally as set forth above, and the suture 710 may be moved toward the center of the capture hole 730 to permit the suture 710 to move transversely out of the capture hole 730.

In the alternative to the foregoing capture method, suture capture may be carried out without significant flexure of the distal end 312. This may be accomplished without the use of a post. In such an alternative method, the steps are similar to those set forth above, but without the associated flexure of the first member 350 and the second member 352. In place of such flexure, the suture 710 may compress to move through the channel 732. Alternatively, a pusher (not shown) can be used to push the suture 710 material through channel 732 and into the capture hole 730. Lastly, two ends of the suture 710 may be grasped to secure the suture 710 as it is either pulled into the suture capture hole 10, or the distal end 312 is advanced until the suture 710 resides in the capture hole 730.

Referring to FIG. 7B, a top elevation view illustrates the distal end 762 of an implant manipulator (not shown) according to another alternative embodiment. The implant manipulator may have a proximal end 310 and an intermediate portion 314 like those of the needle 300 of FIGS. 3A-3C or the needle 400 of FIGS. 4A-4C. The distal end 762 may have an implant interface 764 that may take the form of a suture capture feature 764 designed to retain suture 710 in response to relative motion by which the suture comes toward the distal end 312, as indicated by the arrow 712. The distal end 762 may also have a first member 770 and a second member 772, each of which has a tip 774 with an acute angle selected to facilitate puncturing of tissue.

The suture capture feature 764 is somewhat similar to the suture capture feature 360. The suture capture feature 764 may have a capture hole 780 and a channel 782 extending between the first member 770 and the second member 772 to provide access to the capture hole 780 from distally of the distal end 762. The suture capture feature 764 may generally function similarly to the suture capture feature 360 shown in FIG. 7A. Thus, in response to motion of the suture 710 and/or a post along the direction shown by the arrow 712, the first member 770 and the second member 772 may spread apart and/or the suture 710 may be compressed as it travels through the channel 782.

The capture hole 780 and the channel 782 are different from those of the suture capture feature 360 of FIG. 7A. More specifically, the capture hole 780 may simply be circular in shape, except where it joins the channel 782. The capture hole 780 may be sized somewhat larger than the uncompressed diameter of the suture 710. For a #2 suture, the capture hole 780 may be 0.76 mm in diameter. The channel 782 may have a proximal section 790, a distal section 792, a distal intermediate section 794, and a proximal intermediate section 796. The proximal section 790, the distal section 792, and the proximal intermediate section 796 may be substantially the same as the proximal section 750, the distal section 752, and the intermediate section 754, respectively, of the suture capture feature 360.

The distal intermediate section 794 may be between the distal section 792 and the proximal intermediate section 796. The distal intermediate section 794 may have substantially straight, parallel walls like those of the proximal section 790, but with a larger width. The walls of the distal intermediate section 794 may be 0.30 mm apart.

The distal intermediate section 794 may serve to lengthen the channel 782. This may serve to facilitate flexure of the first member 770 and the second member 772, as a longer moment arm is acting on them during passage of the suture 710 and/or the post through the channel 782. The distal intermediate section 794 may also divide the tactile response of the implant manipulator into more distinct events so that a surgeon can easily tell by the feel of the instrument where the suture 710 is. For example, the surgeon, if operating the implant manipulator manually, may feel some resistance as the suture 710 enters the distal intermediate section 794 from the distal section 792. The surgeon may feel a distinct resistance again when the suture 710 passes from the distal intermediate section 794, through which it passes relatively freely, to the proximal intermediate section 796.

Figure 8:
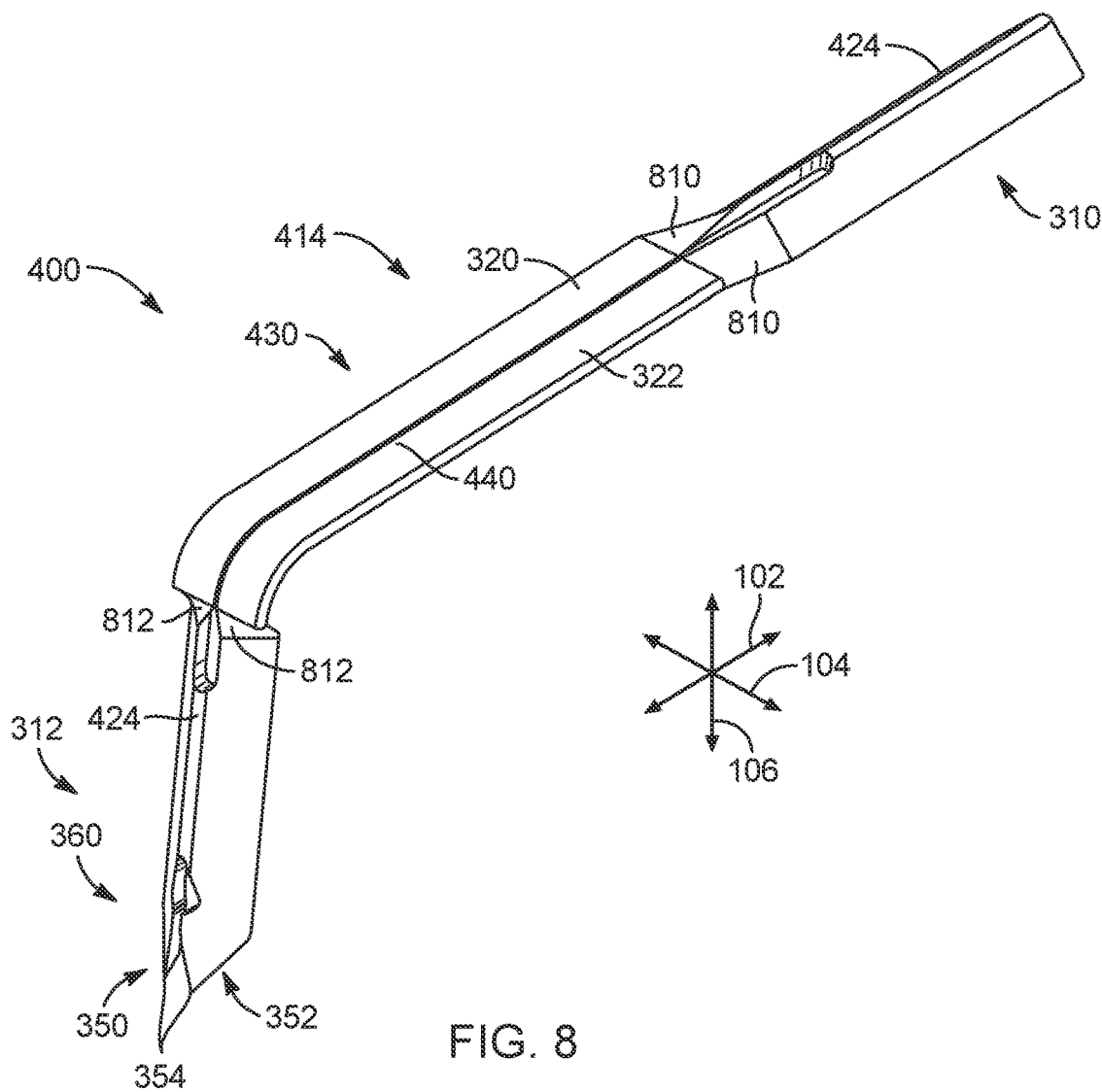
FIG. 8 is a perspective view of the needle of FIGS. 4A-4C with the needle bent in a downward direction.
Figure 9:
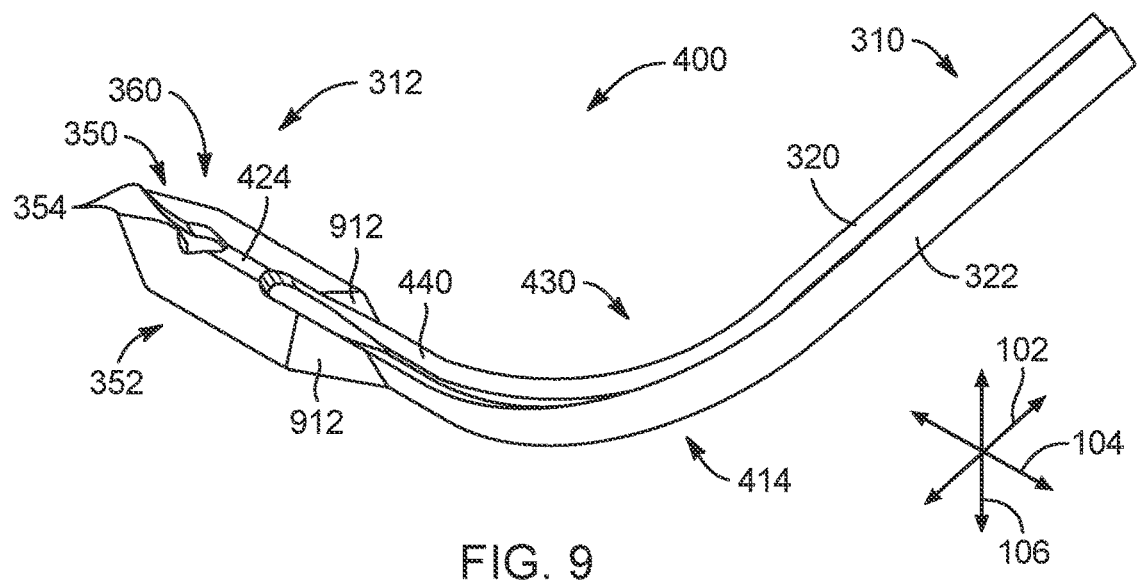
FIG. 9 is a perspective view of the needle of FIGS. 4A-4C with the needle bent to the right.

Referring to FIGS. 8 and 9, perspective views illustrate how the needle 400 of FIGS. 4A-4C may bend. As mentioned previously, the selectively bendable portion 430 may be reconfigurable to enable significant bending along the lateral direction 104 or the transverse direction 106. In FIG. 8, the needle 400 is shown bent in a downward direction, along the transverse direction 106. The proximal end 310 and the distal end 312 may still have the original V-shaped cross-sectional shape; the presence of the spine 424 at the proximal end 310 and the distal end 312 may restrict the ability of the cross-sectional shape at the proximal end 310 and the distal end 312 to change. However, the slot 440 may allow the first arm 320 and the second arm 322 to rotate relative to each other about the longitudinal direction 102 so that the first arm 320 and the second arm 322 become substantially coplanar, as shown in FIG. 2C. This enables the selectively bendable portion 430 to bend along the transverse direction 106 so that the distal end 312 can bend upward or downward relative to the proximal end 310.

FIG. 8 shows the selectively bendable portion 430 flexed to orient the distal end 312 downward relative to the proximal end 310. Similarly, with the first arm 320 and the second arm 322 in the generally coplanar configuration, the selectively bendable portion 430 may flex to orient the distal end 312 upward relative to the proximal end 310.

A transitional region 810 may exist between the proximal end 310 and the selectively bendable portion 430, wherein the cross-sectional shape transitions between the V-shaped cross-sectional shape of the proximal end 310 to the generally coplanar cross-sectional shape of the selectively bendable portion 430. The proximal end 310 may thus remain relatively rigid relative to bending along the lateral direction 104 and the transverse direction 106. This may facilitate retention of the proximal end 310 in a user's hand (not shown), in an actuator (not shown), or in another instrument (not shown).

A transitional region 812 may similarly exist between the distal end 312 and the selectively bendable portion 430, wherein the cross-sectional shape transitions between the V-shaped cross-sectional shape of the distal end 312 to the generally coplanar cross-sectional shape of the selectively bendable portion 430. The distal end 312 may thus remain relatively rigid relative to bending along the lateral direction 104 and the transverse direction 106. This may facilitate retention of an implant such as the suture 710 with the distal end 312, and may also facilitate puncturing of tissue with the distal end 312. If the distal end 312 were to be easily bendable in the lateral direction 104 or the transverse direction 106, axial force pressing the tips 354 into tissue could lead the tips 354 to skive or otherwise deflect from the tissue to be penetrated as the distal end 312 buckles or bends. Thus, keeping the distal end 312 relatively rigid may provide distinct advantages for the invention.

FIG. 9 shows the selectively bendable portion 430 flexed to orient the distal end 312 to the right relative to the proximal end 310. Similarly, with the first arm 320 and the second arm 322 in the generally parallel configuration like that of FIG. 2D, the selectively bendable portion 430 may flex to orient the distal end 312 to the left relative to the proximal end 310.

A transitional region 912 may exist between the distal end 312 and the selectively bendable portion 430, wherein the cross-sectional shape transitions between the V-shaped cross-sectional shape of the distal end 312 to the generally parallel cross-sectional shape of the selectively bendable portion 430. The distal end 312 may thus remain relatively rigid relative to bending along the lateral direction 104 and the transverse direction 106. As mentioned previously, the relative rigidity of the distal end 312 may facilitate implant retention and/or tissue penetration. A similar transitional region may exist between the proximal end 310 and the selectively bendable portion 430.

Referring to FIGS. 10A-11B, there are a number of mechanisms by which a suture, such as the suture 710, may be retained by an implant interface such as the suture capture feature 764 of FIG. 7B. As mentioned previously, one such mechanism is deflection of the distal end 762 that spreads the first member 770 and the second member 772 apart. Such deflection may be carried out by a post or pusher (not shown), or by the suture 710 itself. Different modes of flexure are possible, as will be shown and described in connection with FIGS. 10B and 11B.

Figure 10A:
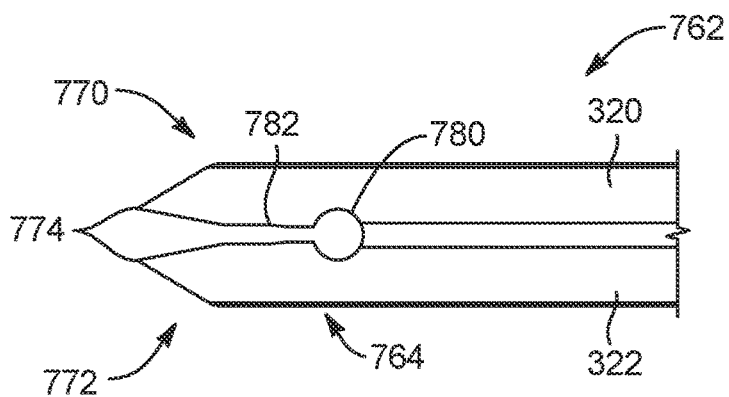
FIGS. 10A-10B are top views of the needle of FIG. 7B illustrating how the suture capture slot may be forced open via non-planar spreading of the first and second members.
Figure 11A:
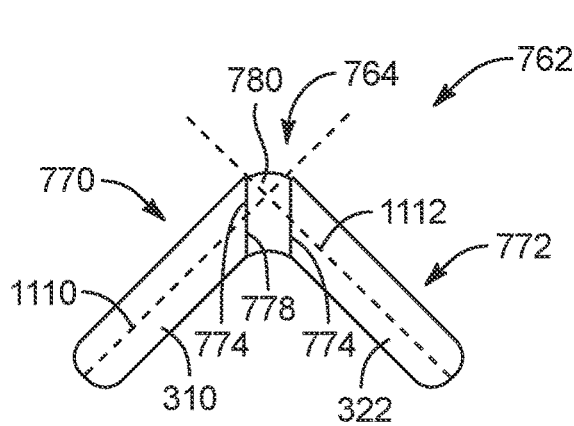
FIGS. 11A-11B are end views of the needle of FIG. 7B illustrating how the suture capture slot may be forced open via lateral compression of the sides.

FIGS. 10A and 11A provide a top elevation view and an end view, respectively, of the distal end 762 of FIG. 7B, in the undeflected state. The channel 782 thus has the shape shown in FIG. 7B, and the first member 770 and the second member 772 extend generally parallel to each other. The first member 770 and the second member 772 may be generally orthogonal to each other, as best seen in FIG. 11A. More precisely, the first member 770 generally resides in a first plane 1110, and the second member 772 generally resides in a second plane 1112 that is generally orthogonal to the first plane 1110.

Figure 10B:
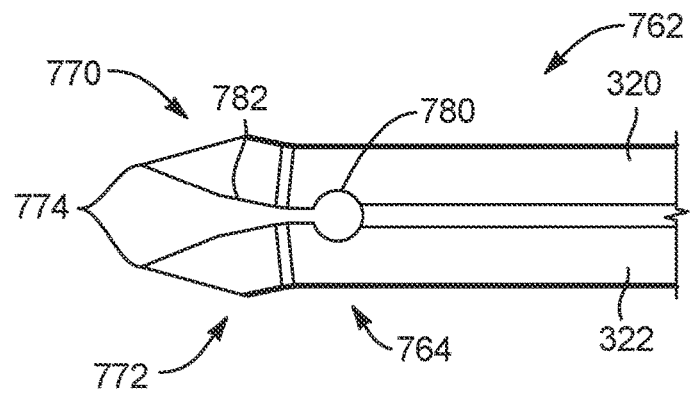

In FIG. 10B, the first member 770 and the second member 772 have been spread apart along the lateral direction 104 to enable the suture 710 to pass through the channel 782 and into the capture hole 780. This motion involves out-of-plane motion of each of the first member 770 and the second member 772. An item that moves out-of-plane moves in a manner that removes it from the plane in which it was prior to the motion. Thus, a thin, flat object that rotates about an axis perpendicular to its large face moves in-plane. Likewise, such an object that moves in a direction parallel to its large face moves in-plane. However, if such an object rotates about an axis that is non-perpendicular to its large face, or moves along a direction nonparallel to its large face, such motion is out-of-plane.

The first member 770 and the second member 772 may each move out-of-plane to reach the configuration shown in FIG. 10B because each of the first and second members 770, 772 moves out of the plane in which it naturally resides. Thus, the first member 770 moves out of the first plane 1110 and the second member 772 moves out of the second plane 1112.

Figure 11B:
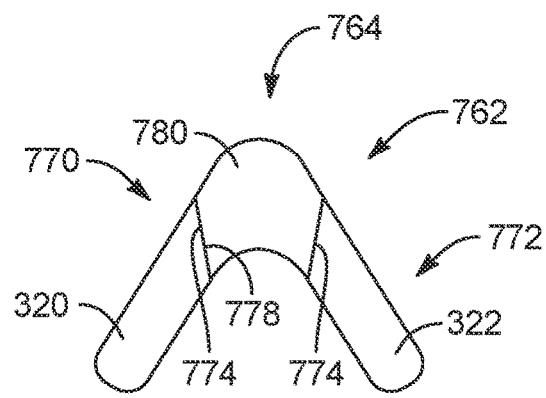

In FIG. 11B, the channel 782 is opened through a different mechanism. More specifically, the first arm 320 and the second arm 322 may be compressed toward each other. As a result, the walls of the channel 782 may generally flex apart to widen the channel 782. This may be accomplished through the use of an instrument (not shown) that has a window or side walls that reduce in width, such that when the distal end 312 is advanced through the instrument, the first arm 320 and the second arm 322 are compressed against the side walls to open the channel 782. Again, out-of-plane flexure of the first member 770 and the second member 772 has occurred to open the channel 782 sufficiently to accommodate passage of the suture 710.

In an alternative embodiment (not shown), the walls of the channel 782 may be angled differently than shown in FIG. 11A to enhance this effect. For example, in place of the configuration of FIG. 11A, the walls of the channel 782 may be angled toward each other so that the channel 782 is narrower at the top than it is at the bottom. Thus, when the first arm 320 and the second arm 322 are compressed toward each other, the walls of the channel 782 may be brought into a more nearly parallel configuration, thereby increasing the width of the narrowest portion of the channel 782.

The various implant manipulators shown and described in FIGS. 1-11B may be used with a wide variety of instruments. In some embodiments, an actuator may be used to control advancement of the implant manipulator into and out of the tissue. Such actuators may be manually operated or drive through the use of motors and/or control systems. FIGS. 12-33 illustrate a number of various instruments that may be used with rigid or flexible implant manipulators. Several of these instruments are designed for use with flexible implant manipulators that pass suture through tissue; those of skill in the art will readily comprehend how their use and configuration may be adapted to rigid implant manipulators and/or implant manipulators designed for use with other implants such as bone anchors, joint replacements, grafts, and the like.

Figure 12:
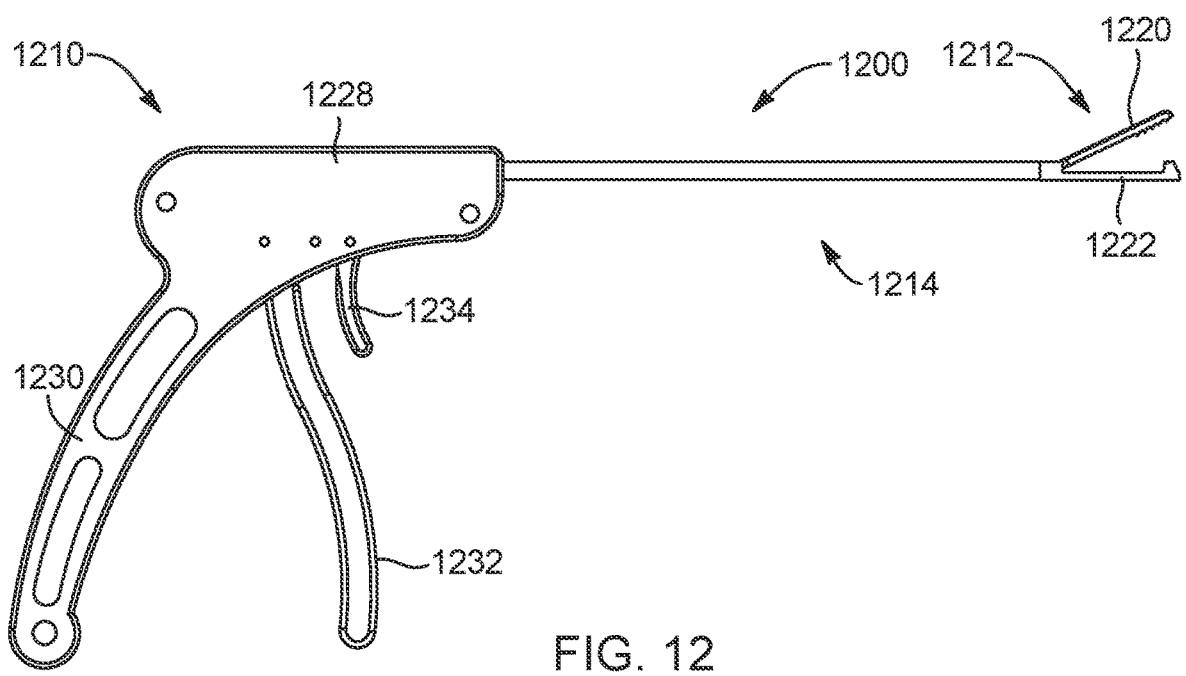
FIG. 12 is a side elevation view of a suture passer with a pair of tissue grasping jaws and a needle that passes from the bottom jaw to the top jaw.

Referring to FIG. 12, a side elevation view illustrates an actuator, which may take the form of an instrument 1200 that may be used to pass the needle 400 into a desired location within tissues such that the distal end 312 is able to capture, retain, and reposition suture therein. The instrument 1200 may thus be called a suture passer. The instrument 1200 may have a proximal end 1210, a distal end 1212, and an intermediate portion 1214. The instrument may pass the distal end 312 between a pair of tissue grasping jaws including an upper jaw 1220 and a lower jaw 1222 at the distal end 1212 of the instrument 1200.

The upper jaw 1220 may pivot around a pin in the lower jaw 1222 and rotate toward and away from the lower jaw 1222. The distal end 312 of the needle 400 may pass upward from the lower jaw 1222 toward the upper jaw 1220. The upper jaw 1220 may temporarily capture a strand of suture material that is ultimately retrieved by the suture capture feature 360 of the needle 400 and pulled back down toward the lower jaw 1222. A structure like that of FIG. 27 may optionally be used to temporarily retain the suture.

The proximal end 1210 of the instrument 1200 may include a chassis 1228 that generally contains the mechanical workings (not shown) of the instrument 1200, a handle 1230, a first user control, which may take the form of a first trigger 1232, and a second user control, which may take the form of a second trigger 1234. According to one example, the second trigger 1234 may be used to control actuation of the needle 400 through the instrument 1200, and the first trigger 1232 may control actuation of the upper jaw 1220 toward the lower jaw 1222. Thus, a surgeon may independently control grasping of tissue and puncture and suture retrieval through the tissue. Those of skill in the art will recognize that many other types of user controls may be used in the alternative to the first trigger 1232 and the second trigger 1234, including sliders, push buttons, and the like. Additionally, in alternative embodiments, one or more than two user controls may be provided and may perform functions different from those recited above.

The intermediate portion 1214 may have a shaft 1240 that is of adequate length such that the handle 1230 and the chassis 1228 may remain outside the body while the distal end 1212 is inserted through a working portal or cannula to reach a joint space, a wound, or another anatomical region that requires suturing.

Figure 13A:
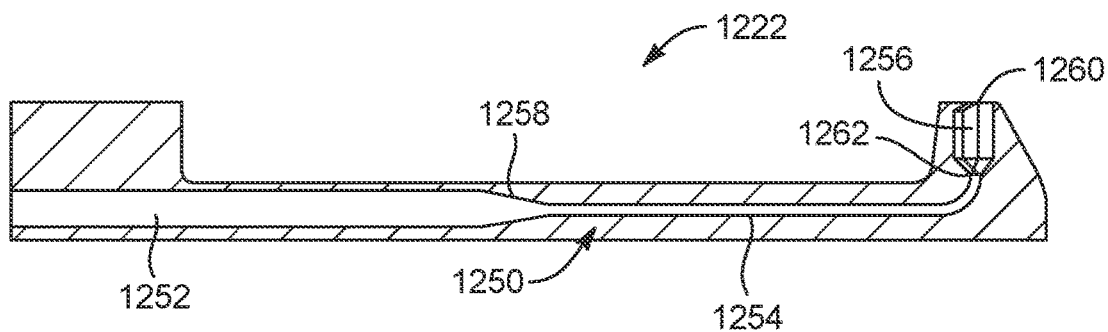
FIG. 13A is side elevation, section view of the lower jaw of the instrument of FIG. 12 demonstrating how the bore of the lower jaw varies in cross-sectional shape.
Figure 13B:
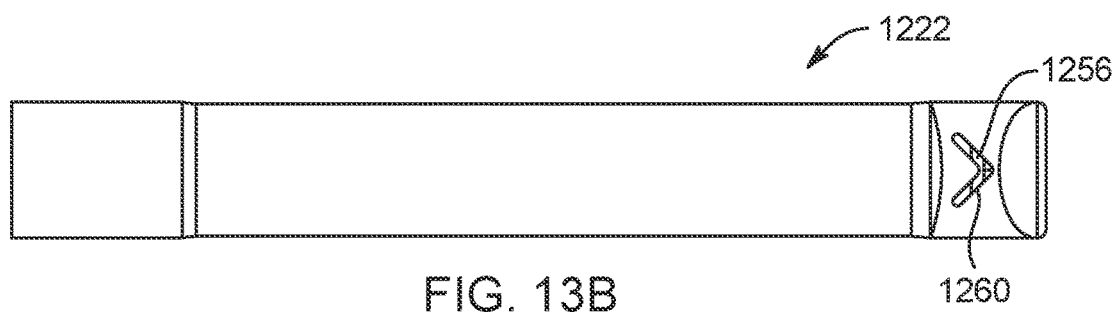
FIG. 13B is a top view of the lower jaw of the instrument illustrating the V-shaped cross-sectional shape of the bore at the distal tip to accommodate the needle.
Figure 14A:
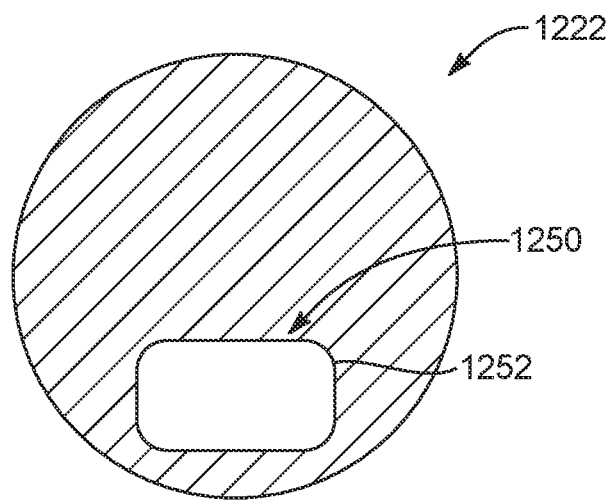
FIG. 14A is a section view of the bore of FIG. 13B.
Figure 14B:
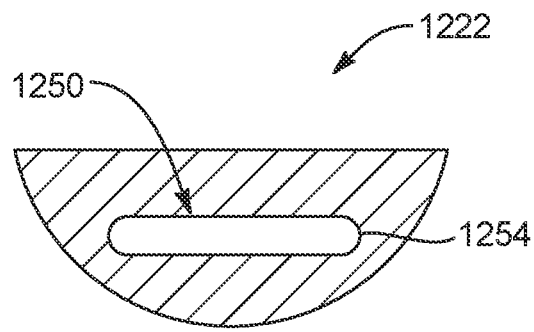
FIG. 14B is another section view of the bore of FIG. 13B.
Figure 14C:
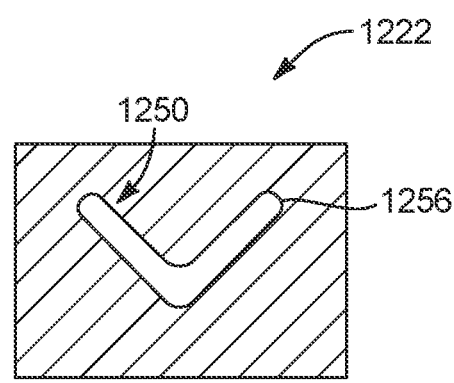
FIG. 14C is another section view of the bore of FIG. 13B.

Referring to FIGS. 13A-14C, the lower jaw 1222 of the instrument 1200 is shown in greater detail. FIGS. 13A and 13B, side elevation and top elevation views, respectively, illustrate the lower jaw 1222 of the instrument 1200 in greater detail. FIGS. 14A-14C illustrate section views of various portions of the lower jaw 1222. The lower jaw 1222 may have a bore 1250 shaped to cause the needle 400 to bend as it moves through the lower jaw 1222 in a manner similar to that of FIG. 8.

In order to accomplish the varying cross-sectional shapes of the needle 400, the lower jaw 1222 may include three distinct sections including a first section 1252, a second section 1254, and a third section 1256 as shown in FIG. 13A. The first section 1252 may accommodate the needle 400 with its substantially undeflected V-shaped cross-sectional shape, as shown in FIG. 2B. The cross-sectional shape of the first section 1252 may be relatively rectangular as shown in FIG. 14A.

The second section 1254 may accommodate the needle 400 with its substantially flat, coplanar cross-sectional shape, as shown in FIG. 2C. The cross-sectional shape of the second section 1254 may thus be a relatively thin, wide rectangular shape, as shown in FIG. 14B, by comparison with the first section 1252. In order to assist this shape change, a first transitional region 1258 may be present between the first section 1252 and the second section 1254. In this first transitional region 1258, the cross-sectional shape of the bore 1250 gradually alters between the shape of the first section 1252 and the shape of the second section 1254.

The third section 1256 may then cause the needle 400 to revert back to the more rigid V-shaped configuration as it exits an aperture 1260 of the lower jaw 1222 as shown in FIG. 13B. In this third section 1256, the cross-sectional shape may be substantially V-shaped as shown in FIG. 14C. A second transitional region 1262 may also exist between the second section 1254 and the third section 1256 to gradually force the cross-sectional shape of the needle 400 to change as it passes from the second section 1254 to the third section 1256. Thus, the needle 400 may bend to extend upward, toward the upper jaw 1220, and yet retain sufficient stiffness at the aperture 1260 to enable it to effectively pierce tissue. "Piercing" tissue relates to pushing a sharp feature into the tissue to form an opening in the tissue, as opposed to simply moving a feature into an existing hole in the tissue.

Figure 15:
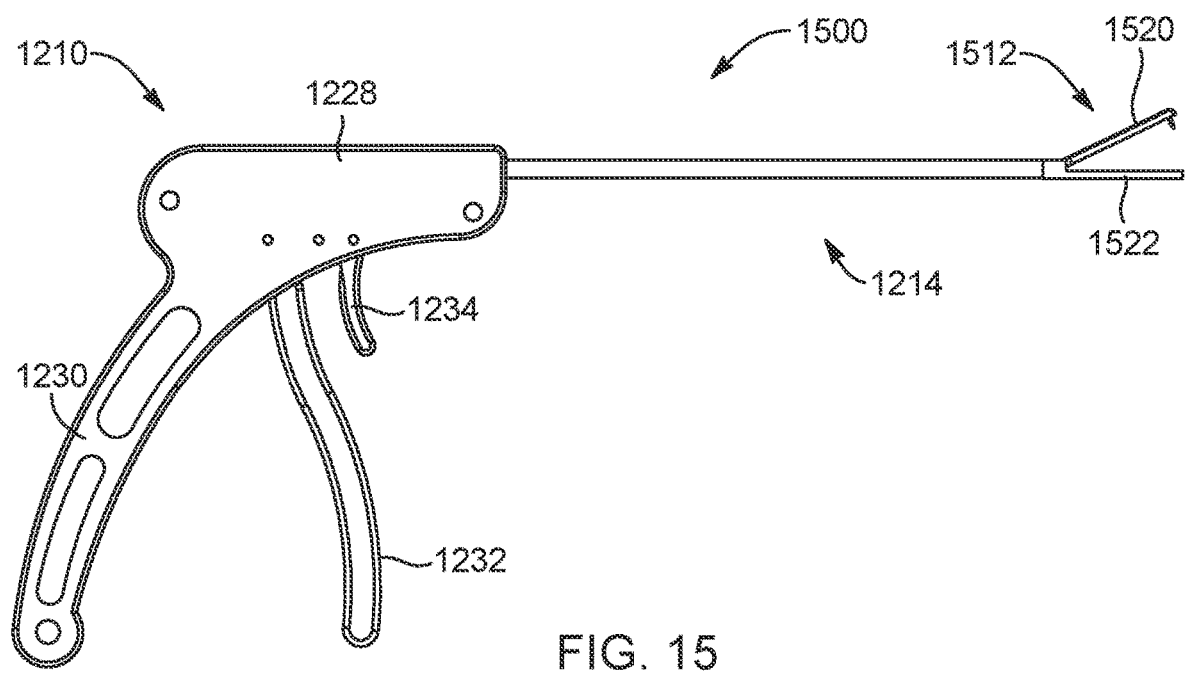
FIG. 15 is a side elevation view of a suture passer with a pair of tissue grasping jaws with a needle that passes from the top jaw to the bottom jaw.

Referring to FIG. 15, a side elevation view illustrates an instrument 1500 according to one alternative embodiment. The instrument 1500 may be a suture passer with a proximal end 1210 and an intermediate portion 1214 like those of FIG. 12. However, the instrument 1500 may have a distal end 1512 with an upper jaw 1520 and a lower jaw 1522 that are configured differently from those of FIG. 12.

The instrument 1500 may pass an implant manipulator, such as the needle 400 of FIGS. 4A-4C, from the upper jaw 1520 to the lower jaw 1522. The lower jaw 1522 may temporarily capture a strand of suture material that is ultimately retrieved by the suture capture feature 360 of the needle 400 and pulled back up toward the upper jaw 1520. Thus, the upper jaw 1520 may have a bore like the bore 1250 of the instrument 1200 of FIGS. 12-14C.

As mentioned previously, the distal end 312 of the needle 400 may have the spine 424 intact, and may thus be resistant to flexure into the flat cross-sectional shape shown in FIG. 2C to permit bending of the distal end 312. There are a number of alterations to the upper jaw 1520 and the lower jaw 1522 that can be made that would allow for the distal end 312 of the needle 400 to remain in the V-shaped configuration while the needle 400 only bends in the regions where the slot 440 exists (e.g., in the selectively bendable portion 430).

According to one example, an instrument like the instrument 1500 may have an upper jaw or a lower jaw with a movable distal tip that translates, slides, pivots, or rotates to move the distal tip of the needle, without deformation, from a first position substantially parallel to the long axis of the instrument to a second position substantially perpendicular to the long axis of the instrument. One such example will be shown and described in connection with FIGS. 16A-18B.

Referring to FIGS. 16A-18B, a variety of views illustrate a distal end 1612 of an instrument (not shown) according to another embodiment of the invention. The distal end 1612 may have an upper jaw 1622 (or in other alternative embodiments, a lower jaw) with a main body 1650 and a sliding tip 1652. The distal end 1612 may facilitate re-orienting of the distal end 312 of the needle 400 in a manner that does not require significant bending of the distal end 312.

Figure 17:
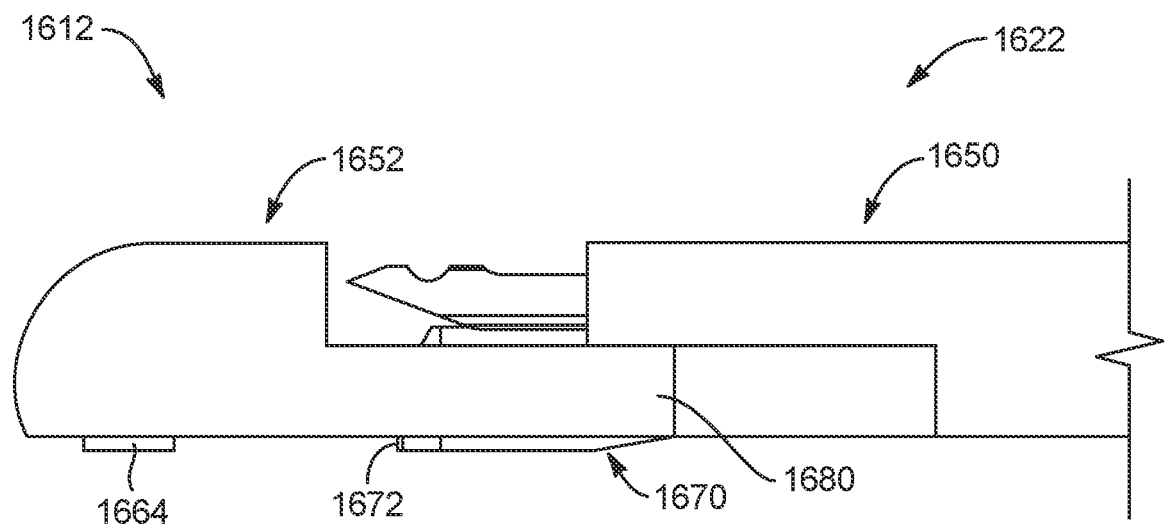
FIG. 17 is a side elevation view showing the distal end of the top jaw with the sliding tip in an extended position with the needle in an initial straight configuration.

The sliding tip 1652 may have a first position and a second position. In the first position, the sliding tip 1652 may be displaced from the main body 1650 along the axis of the distal end 1612 so that the needle 400 remains in a substantially straight configuration, proximal to distal, that is parallel to the upper jaw 1622. This first position is illustrated in FIG. 17. In a second position shown in FIGS. 18A-18B, the sliding tip 1652 may be retracted proximally such that it is positioned immediately adjacent to the main body 1650. The distal end 312 of the needle 400 is shown exiting the upper jaw 1622 in a direction substantially perpendicular to the upper jaw 1622.

Figure 16A:
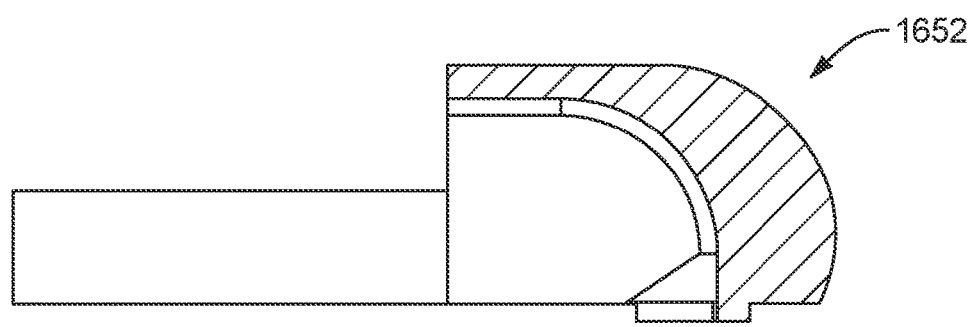
FIG. 16A is a side elevation, section view of a sliding tip of a suture passer according to an alternative embodiment of the invention.
Figure 16B:
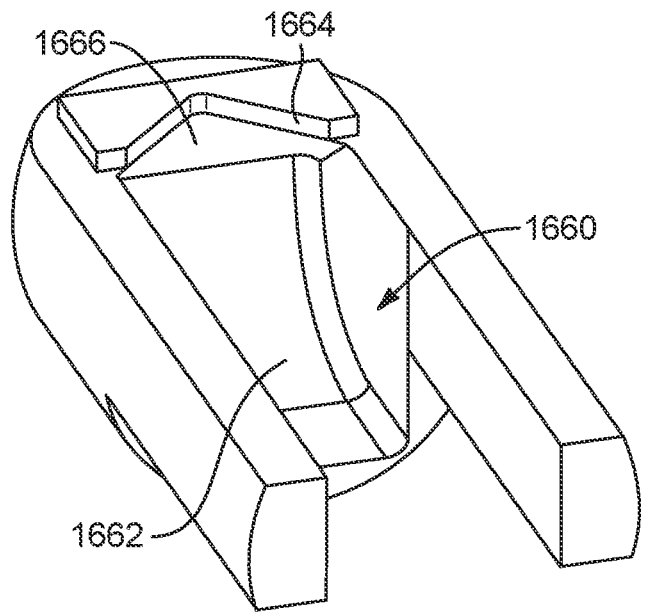
FIG. 16B is a perspective view of the underside of the sliding tip of FIG. 16A.

As best seen in FIGS. 16A and 16B, the sliding tip 1652 may have an interior contour 1660 defining a curved wall 1662, a V-shaped wall 1664 at the exit point of the upper jaw 1622, and a transitional region 1666 where the interior contour 1660 gradually transforms from the shape of the curved wall 1662 to that of the V-shaped wall 1664.

As the distal end 312 of the needle 400 is advanced through the upper jaw 1622, or the upper jaw 1622 is retracted, the distal end 312 of the needle 400 may initially begin to deflect downward as it contacts the curved wall 1662 of the upper jaw 1622. The flexure may occur along the region of the needle 400 where the slot 440 exists, e.g., the selectively bendable portion 430. The first arm 320 and the second arm 322 of the needle 400 may undergo a shape change from the V-shaped configuration (as in FIG. 2B) to a relatively flat configuration (as in FIG. 2C) such that the needle 400 can bend. As the needle 400 is further advanced, the distal end 312 may exit the upper jaw 1622 at the V-shaped wall 1664.

Figure 18A:
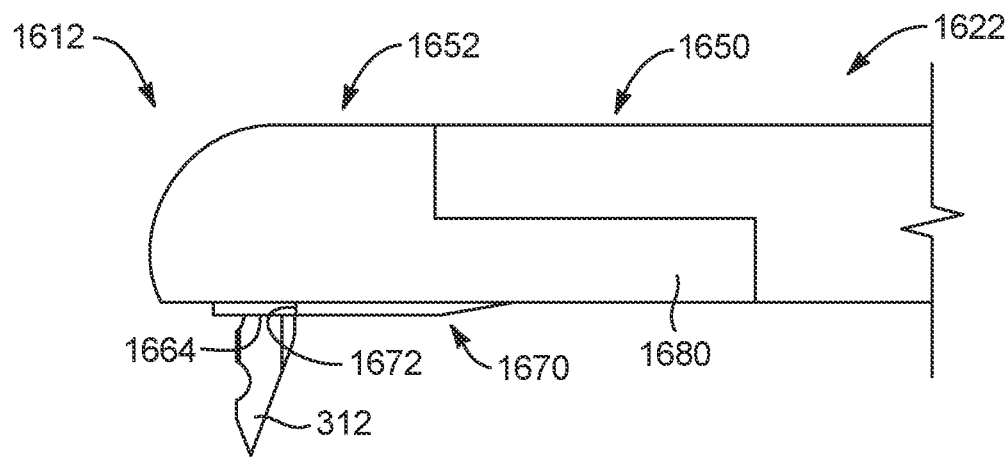
FIGS. 18A-18B are side elevation and bottom views of the distal end of the top jaw with the sliding tip in a retracted position with the needle bent downward.
Figure 18B:
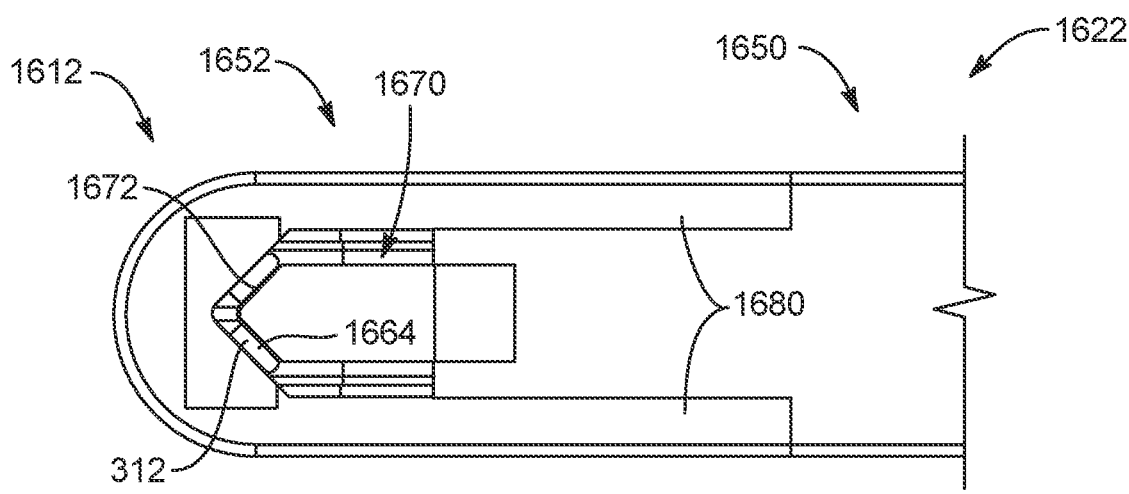
Figure 19:
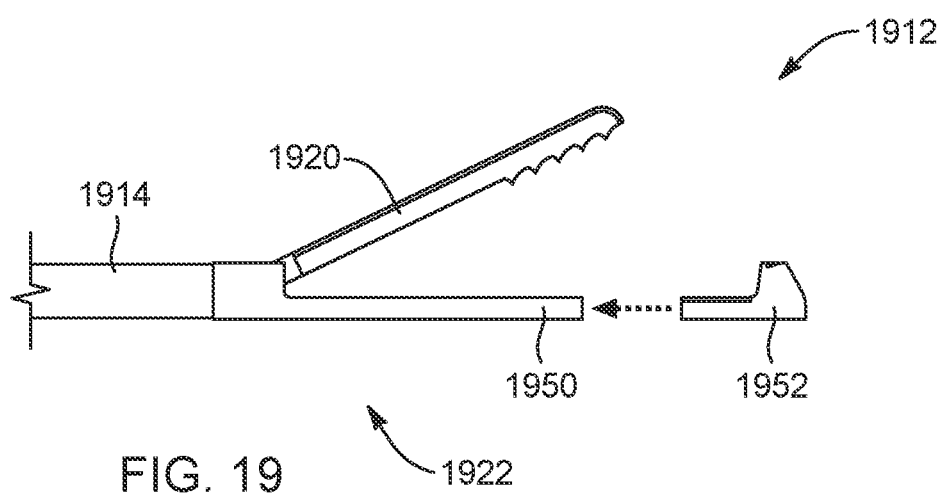
FIG. 19 is a side elevation view of a cartridge tip that may be slidably inserted into the distal end of an instrument according to an alternative embodiment of the invention.
Figure 20:
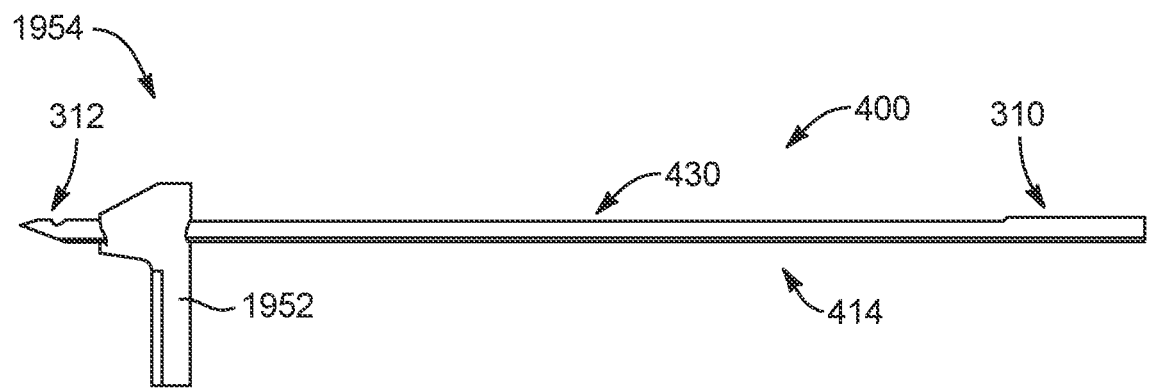
FIG. 20 is a side elevation view showing how the needle may be supplied pre-loaded into the cartridge.

As the selectively bendable portion 430 of the needle 400 reaches the V-shaped wall 1664, the first arm 320 and the second arm 322 may be forced back to a V-shaped configuration (as in FIG. 2B) as they slide along the interior contour 1660. The main body 1650 of the upper jaw 1622 may have an extending feature 1670 with a peaked surface 1672 that represents the interior portion of the V-shape, the exterior portion of which is provided by the V-shaped wall 1664, as shown in FIG. 18B. The V-shaped wall 1664 and the peaked surface 1672 may thus cooperate to force the first arm 320 and the second arm 322 of the needle 400 to exit the upper jaw 1622 in the generally rigid V-shaped configuration. Two extension arms 1680 may be in contact with the main body 1650 of the upper jaw 1622 to slidably couple the sliding tip 1652 to the main body 1650. The extension arms 1680 may be connected to an actuation rod (not shown) that connects to one of the user controls (not shown) of the instrument, allowing for the user to control the extension and/or retraction of the sliding tip 1652 relative to the main body 1650.

In the alternative to positioning such a mechanism on the upper jaw 1622, a corresponding lower jaw 1620 (not shown) may be modified to have a main body 1650 and a tip 1652 like those shown in FIGS. 16A-18B. Alternatively, the distal end 312 of the needle 400 may be captured inside a pivoting tip (not shown) of one of the jaws. As the pivoting tip pivots from a first position to a second position, the selectively bendable portion 430 of the needle 400 may flex and pivot around the curve while the distal end 312 remains in the V-shaped configuration.

The embodiments described above describe an instrument for which the needle may be inserted from the proximal end of the instrument and travels towards the distal end. However, in alternative embodiments, the needle may be inserted into the distal end of the instrument and moved proximally to seat in the proximal end.

Referring to FIGS. 19-21B, a variety of views illustrate a distal end 1912 of an actuator (not shown) according to another embodiment of the invention. As shown, the actuator may have an intermediate portion 1914 in addition to the distal end 1912. The distal end 1912 may have an upper jaw 1920 and a lower jaw 1922 that includes a main body 1950 and a cartridge 1952. The cartridge 1952 may be slidably inserted onto the end of the main body 1950. A needle like the needle 400 of FIGS. 4A-4C may be pre-loaded in the cartridge 1952 to provide an assembly 1954 that can be inserted into the end of the main body 1950 of the lower jaw 1922.

Figure 21A:
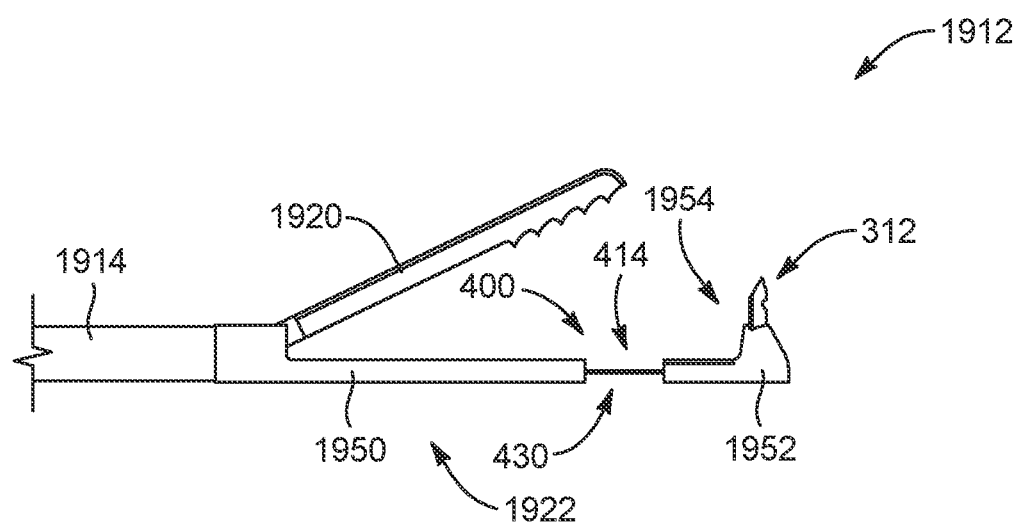
FIG. 21A is a side elevation view of the distal end of an instrument showing how the proximal end of the needle can be inserted into the instrument followed by the cartridge to complete the assembly.

FIG. 21A illustrates one manner in which the assembly 1954 may be inserted into engagement with the main body 1950. As shown, the proximal end 310 of the needle 400 may be inserted into the corresponding opening (not shown) in the main body 1950 of the lower jaw 1922. The assembly 1954 may need to be rotated to cause the needle 400 to flex such that the assembly 1954 can be fully inserted into main body 1950 as shown in FIG. 21B.

Figure 21B:
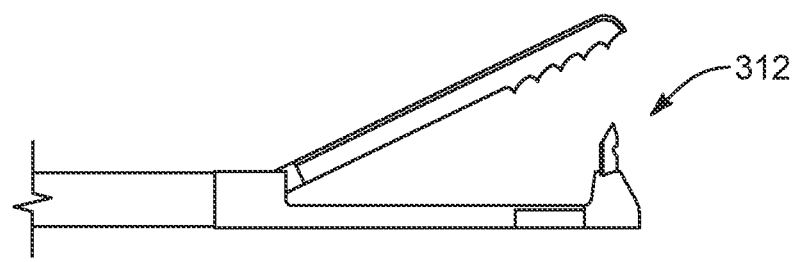
FIG. 21B is a side elevation view of the distal end of the instrument showing the final assembly of the cartridge into the lower jaw.
Figure 22:
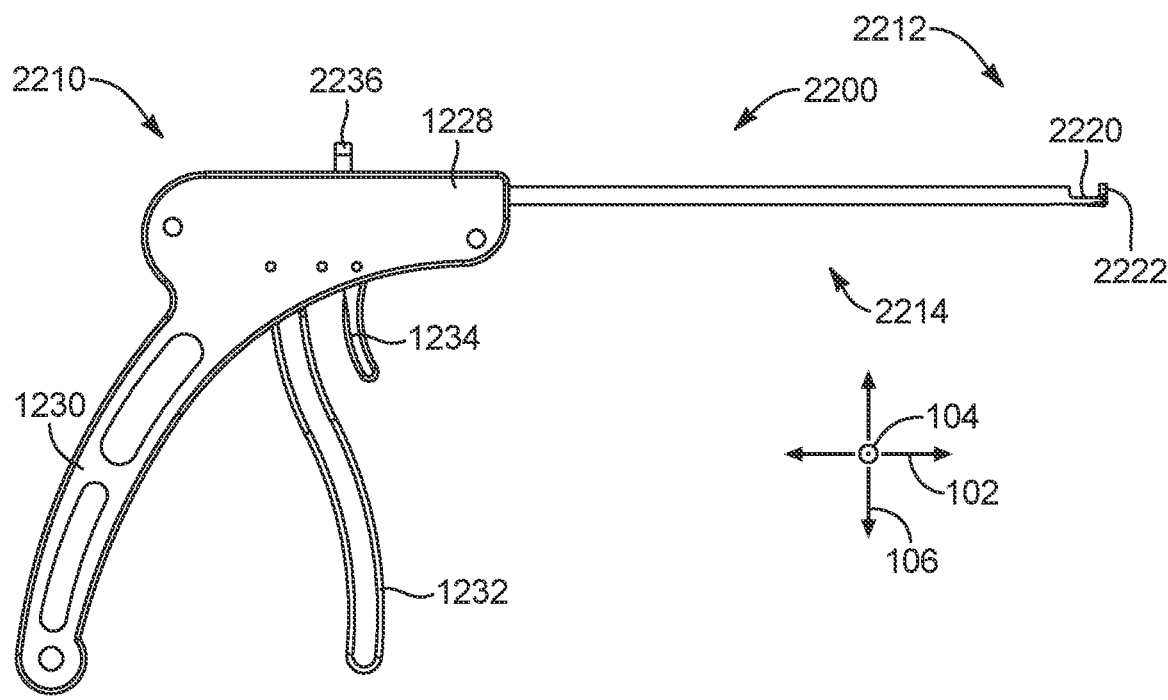
FIG. 22 is a side elevation view of a suture passer with a single jaw.

In general, the instrument of FIGS. 19-21B may provide the benefit of avoiding the needle having to pass through the distal end 312 through a nonlinear actuation pathway. Since the distal end 312 is positioned beyond the end of the bore that extends through the intermediate portion 1914 and through the lower jaw 1922, it need not follow a curved pathway. Rather, the intermediate portion 414, or more specifically, the selectively bendable portion 430, may bend to orient the distal end 312 generally perpendicular to the length of the instrument, as shown in FIG. 21B.

In other embodiments of the invention, an implant manipulator need not bend around a curve, but may instead remain in a rigid configuration as it translates along a single plane. As mentioned previously, the implant manipulator 100 and the implant manipulator 300 may both be substantially rigid. Such implant manipulators may be used in a wide variety of instruments.

Referring to FIGS. 22-28, various views illustrates an instrument 2200 according to another embodiment of the invention. The instrument 2200 may also be a suture passer, and may use a rigid needle like the needle 300 of FIGS. 3A-3C to pass suture through tissue. The instrument 2200 may have proximal end 2210, a distal end 2212, and an intermediate portion 2214 between the proximal end 2210 and the distal end 2212. The proximal end 2210 may be similar to the proximal end 1210 of the instrument 1200 of FIGS. 12-14C. Thus, the proximal end 2210 may have a handle 1230, a first user control in the form of a first trigger 1232, and a second user control in the form of a second trigger 1234. The intermediate portion 2214 may be similar to the intermediate portion 1214.

The distal end 2212 of the instrument 2200 may have a cutout section 2220 and jaw 2222 that pivots around a shaft or other pivot point proximate the distal terminus of the cutout section 2220. The cutout section 2220 may provide a location for the tissue to be inserted between the distal end 312 of the needle 300, which may reside within the interior of the intermediate portion 2214 proximally of the cutout section 2220, and the jaw 2222.

Figure 23A:
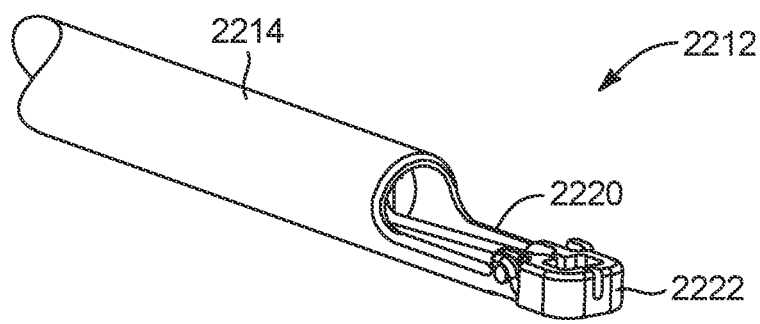
FIG. 23A is a perspective view showing the distal end of the instrument of FIG. 22 with the jaw in a first position.
Figure 23B:
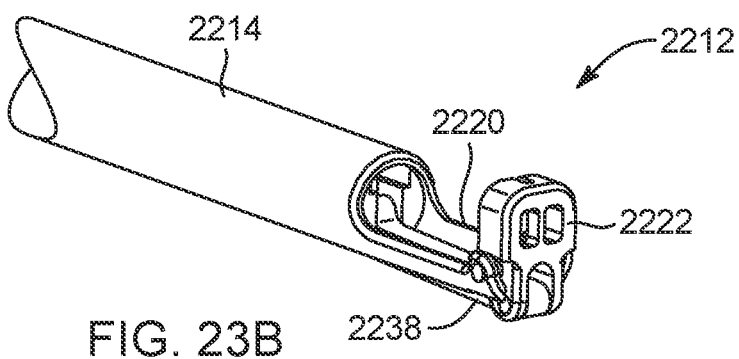
FIG. 23B is a perspective view showing the distal end of the instrument of FIG. 22 with the jaw in a second position.

The second trigger 1234 may be used to rotate the jaw 2222 between a first position in which the jaw 2222 is oriented generally parallel to the intermediate portion 2214, as shown in FIG. 23A, and a second position in which the jaw 2222 is oriented generally perpendicular to the intermediate portion 2214, as shown in FIG. 23B. The first trigger 1232 may be used to actuate the needle 300 from a first position in which the needle 30 is disposed entirely, or nearly entirely, within the intermediate portion 2214, to a second position in which the distal end 312 of the needle 300 extends across the cutout section 2220 to the jaw 2222. The needle 300 may be coupled at its proximal end 310 to a tab 2236 that connects to a needle carriage device (not shown) that pushes and pulls the needle 300 between the two positions as the first trigger 1232 is used.

FIG. 23A shows the jaw 2222 in the first position as described above. The jaw 2222 is substantially parallel to the intermediate portion 2214. This first position may be useful to manipulate the distal end 2212 of the instrument 2200 into a working cannula or other narrow access portal (not shown) and into the correct anatomical location because, in the first position, the profile of the distal end 2212 of the instrument 2200 is minimized.

FIG. 23B shows the jaw 2222 in the second position as described above. The jaw 2222 is substantially perpendicular to the intermediate portion 2214. This second position may be useful for suture passing steps as the distal end 312 of the needle 300 may need to pass into the jaw 2222. Further, this rotation of the jaw 2222 may also allow the height of the jaw 2222 along the transverse direction 106 to exceed the height of the intermediate portion 2214. A link 2238 may be connected to the jaw 2222 and to the second trigger 1234 so that actuation of the second trigger 1234 rotates the jaw 2222 between the first and second positions.

Figure 26:
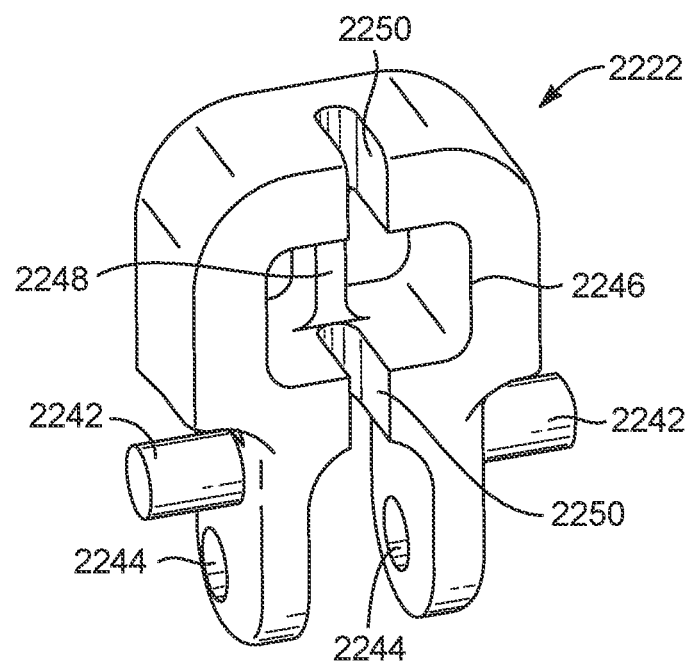
FIG. 26 is a perspective view of the jaw of the suture passer of FIG. 22.

FIG. 26 is an oblique view showing the jaw 2222 in greater detail. A first set of pins 2242 may be used to connect the jaw 2222 to the cutout section 2220 and provide a pivot point for the rotation of the jaw 2222 relative to the remainder of the instrument 2200. Two aligned holes 2244 may be used to connect the jaw 2222 to the actuation link 2238. A window 2246 may extend through the width of the jaw 2222 to accommodate passage of distal end 312 of the needle 300. The distal end of the window 2246 may have a central post 2248 that can be used to support the suture 710 and may be used to spread the suture capture feature 360 on the needle 300 as previously described. A slot 2250 may be provided to temporarily capture a section of a suture such as the suture 710. The narrow width of the slot 2250 may enable the slot 2250 to securely hold the suture 710 to temporarily capture it, while remaining able to release the suture 710 in response to application of a small removal force, such as that applied to the suture 710 such as when it is being retrieved by the needle 300. The slot 2250 may optionally have a boss or other positive feature (not shown) such as a bump, wedge, or bulge that provides a secondary constraint on the suture.

Figure 24:
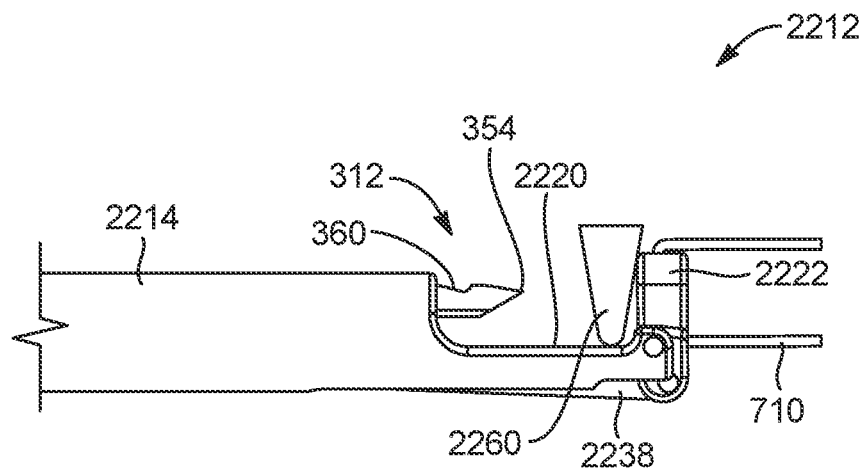
FIG. 24 is a side elevation view of the distal end of the instrument of FIG. 22 with the distal end positioned adjacent to a piece of tissue to be sutured.
Figure 27:
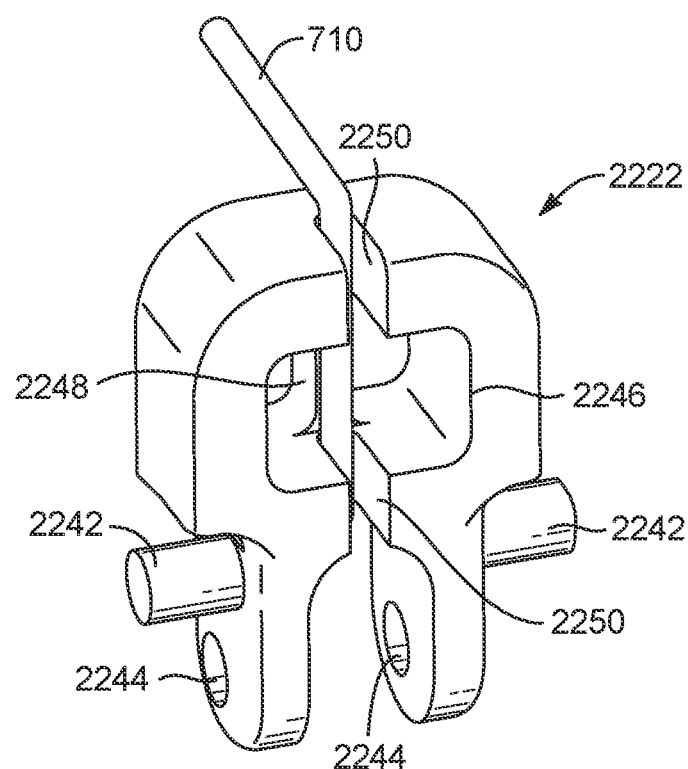
FIG. 27 is a perspective view of the jaw of the suture passer of FIG. 22 with the suture temporarily captured within the jaw.

In FIG. 27, a section of suture 710 is shown temporarily constrained within the slot 2250. The suture 710 may lay adjacent to the central post 2248. The suture 710 may be pre-loaded into the instrument 2200 prior to use. Once the suture 710 has been pre-loaded onto the instrument 2200, the jaw 2222 may be placed in the first position (FIG. 23A). The instrument 2200 may then be inserted into a working cannula or other portal with access to the desired location, i.e., the anatomical space at which suturing is to be performed. The jaw 2222 may then be actuated to the second position adjacent to and behind the piece of tissue 2260 to be sutured, as shown in FIG. 24.

Figure 25:
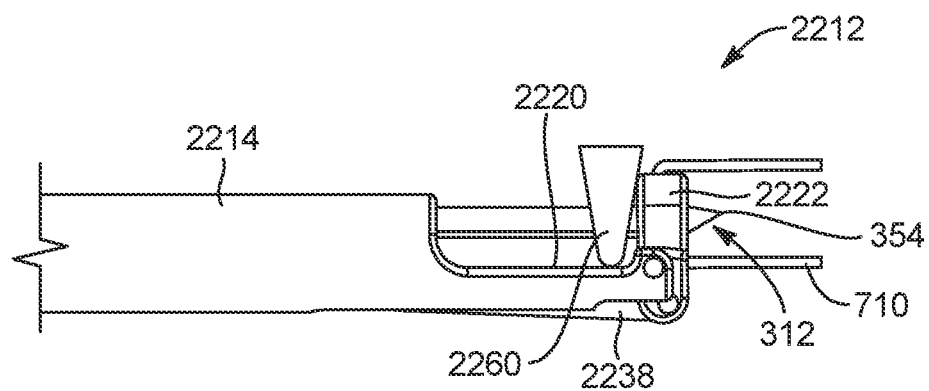
FIG. 25 is a side elevation view of the distal end of the instrument of FIG. 22 showing the needle passing through the tissue and into the jaw.

FIG. 25 shows the needle 300 after it has been actuated to an extended position. The tips 354 of the needle 300 have punctured the tissue 2260 and the distal-most portion of the distal end 312 has passed through the tissue 2260 and into the window 2246 of the jaw 2222. As the distal end 312 of the needle 300 is being extended into the jaw 2222, the suture 710 may translate into the suture capture feature 360. The central post 2248 may serve two purposes during this step of the procedure. First, the suture 710 may be prevented from being pushed distally by the advancing distal end 312 as the central post 2248 serves as a stop that the suture 710 cannot be pushed past. Second, the central post 2248 may be used to urge the first member 350 and the second member 352 of the distal end 312 to move apart (as shown in FIGS. 10B and/or 11B), allowing the suture 710 to enter the capture hole 730.

Figure 28:
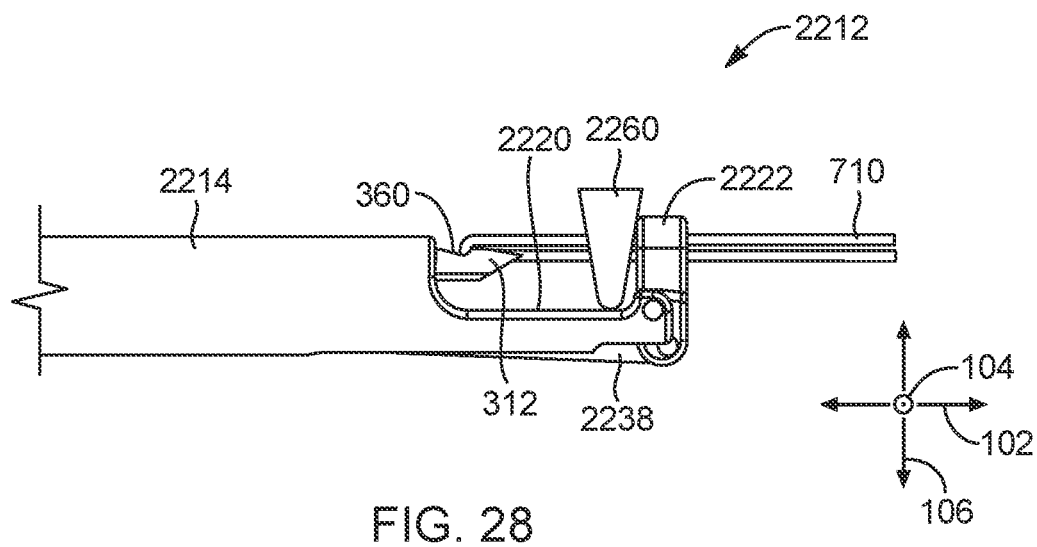
FIG. 28 is a side elevation view of the distal end of the suture passer of FIG. 22 showing retraction of the needle back through the tissue to retrieve the suture.

The needle 300 may then be retracted towards the proximal end 2210 of the instrument 2200 with the suture 710 retained in the capture hole 730 so that the suture 710 is drawn back through the tissue 2260 as shown in FIG. 28. The needle 300 may be retracted back into the intermediate portion 2214 such that the suture 710 is compressed between the interior wall of the intermediate portion 2214 and the needle 300, which compression may more securely lock the suture 710 in place. As the distal end 2212 of the instrument 2200 is then removed from the body, the suture 710 may be retained securely so as to not be dislodged from the instrument 2200. Lastly, to remove the suture 710 from the instrument 2200, the needle 300 may need to be slightly advanced, such that one end of the suture 710 can be pulled along the transverse direction 106 (i.e., up or down with reference to FIG. 28) and out of the capture hole 730.

The instrument 2200 provides a linear pathway for travel of the needle 300; accordingly, use of the generally rigid needle 300 is suitable. In alternative embodiments, the instrument 2200 may be modified to have a nonlinear actuation pathway for needle travel. For example, the intermediate portion 2214 may be curved along a radius of curvature to enable the distal end 2212 to move along an arcuate pathway through the body. Alternatively, the intermediate portion 2214 may remain straight, but the needle may be guided along a nonlinear actuation pathway proximate the distal end 2212.

Figure 29:
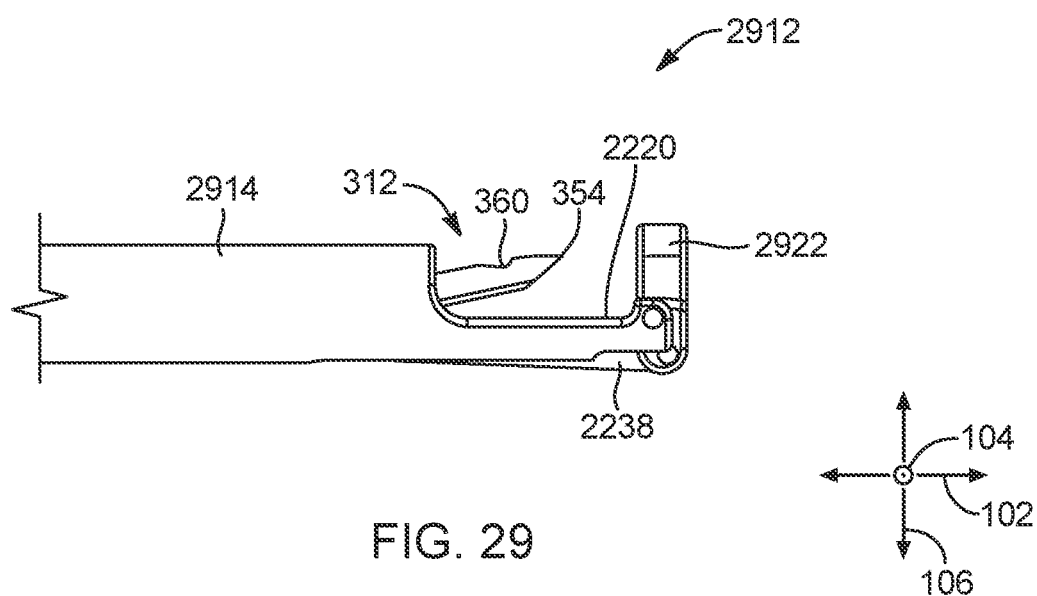
FIG. 29 is a side elevation view of a distal end of a suture passer according to an alternative embodiment of the invention, showing emergence of the needle at a non-parallel angle to the intermediate portion of the instrument.

In such embodiments, a flexible needle like the needle 400 of FIGS. 4A-4C may be used. According to one alternative embodiment, shown in FIG. 29, the needle 400 may need to travel along a pathway that curves at the distal end to provide a greater bite depth of tissue. In FIG. 29, an instrument (not shown) may be configured generally similarly to the instrument 2200 of FIGS. 22-28, except that the instrument of FIG. 29 has a distal end 2912 and an intermediate portion 2914 configured to carry out suturing with a greater bite depth in the tissue 2260. Thus, the distal end 312 of the needle 400 may exit the intermediate portion 2914 at an upward angle. The distal end 2912 may have a cutout section 2220, a jaw 2922, and a link 2238 that operate in a manner generally similar to those of the instrument 2200.

A feature such as a ramp, bump, post, pin or other feature may be positioned within the interior of the intermediate portion 2914, proximate its distal opening. The distal end 312 of the needle 400 may contact such a feature, which may then redirect the distal end 312 of the needle 400 as it exits the interior of the intermediate portion 2914. With this modified exit angle, the height of the jaw 2922 (along the transverse direction 106 as shown in FIG. 29) and/or location of the window 2246 (not shown in FIG. 29) may need to be altered from those of the jaw 2222 of FIGS. 22-28 so that the window 2246 can accommodate passage of the angled distal end 312.

Figure 30:
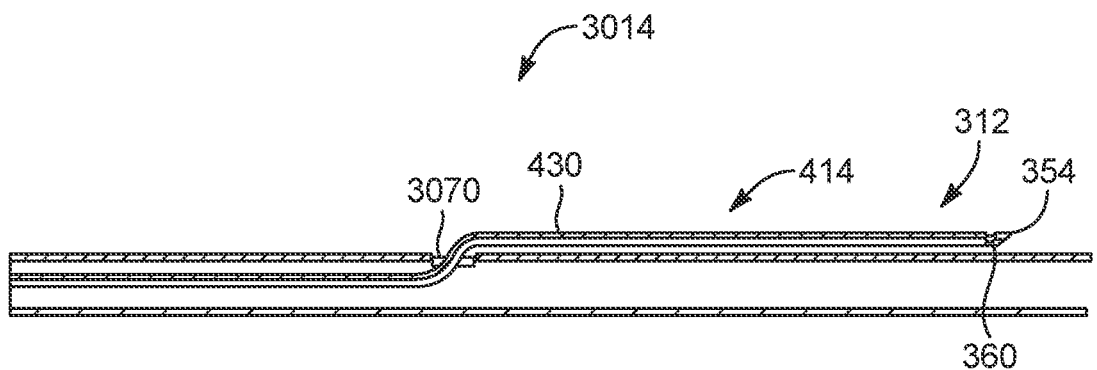
FIG. 30 is a side elevation, section view of an intermediate portion of an instrument according to an alternative embodiment of the invention, illustrating how the needle may be bent such that it exits the intermediate portion of the instrument proximally of the distal end.

FIG. 30 is a side elevation, section view illustrating an intermediate portion 3014 of an instrument (not shown) according to another alternative embodiment of the invention. The needle 400 may exit the intermediate portion 3014 through a window 3070, which may be on the upper surface of the intermediate portion 3014. This may allow the needle 400 to exit the intermediate portion 2914 at a more proximal location, while still keeping the overall profile of the entire instrument substantially the same so that it still fits through the desired cannula or other portal to the working location within the body. If desired, one or more various features such as ramps, bumps, posts, pins or the like may be positioned within the interior of the intermediate portion 3014 or outside the intermediate portion 3014 to enable the needle 400 to move along the nonlinear actuation pathway shown in FIG. 30.

Figure 31:
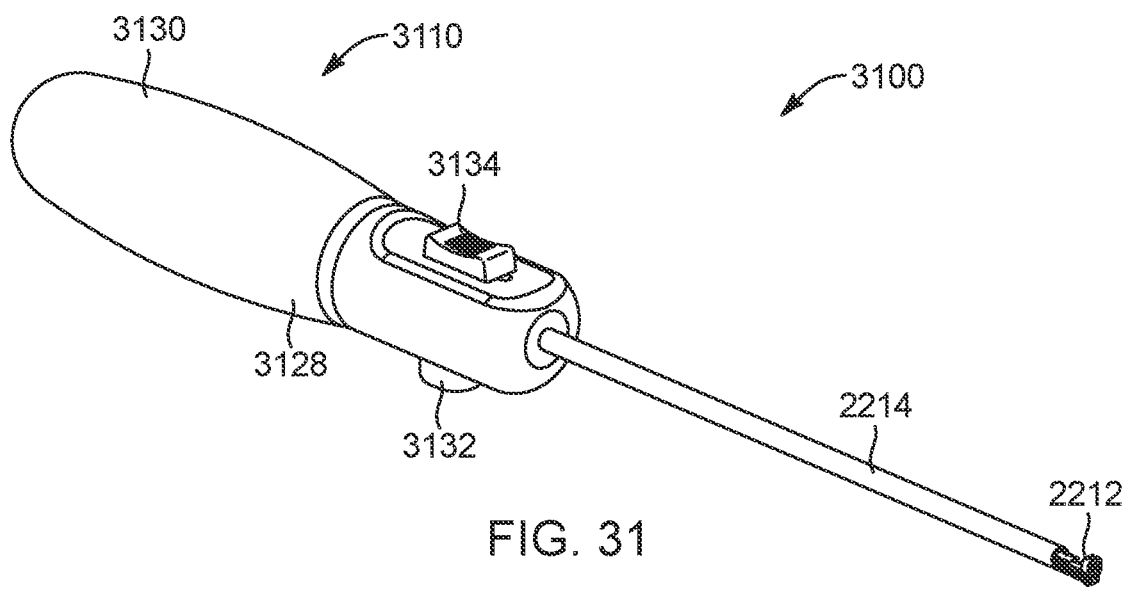
FIG. 31 is a perspective view showing a suture passer with an alternative proximal end.

In FIG. 31, a perspective view illustrates an instrument 3100 according to another embodiment of the invention. The instrument 3100 may have a distal end 2212 and intermediate portion 2214 like those of the instrument 2200 of FIGS. 22-28. However, the instrument 3100 may also have a proximal end 3110 that is different from the proximal end 2210 of the instrument 2200.

The proximal end 3110 of the instrument 3100 may have a handle 3130 with a straight style different from the pistol grip style illustrated in other figures herein. As with previous embodiments, the handle design of FIG. 31 may be used with a wide variety of user controls including push buttons, sliders, levers, triggers, or other similar mechanisms. In FIG. 31, the proximal end 3110 has a chassis 3128 that generally contains the mechanical workings (not shown) of the instrument 3100. A first user control may take the form of a push button 3132, and a second user control may take the form of a slider 3134. The push button 3132 and the slider 3134 may perform functions similar to the first trigger 1232 and the second trigger 1234 of FIG. 12. The distal end 2212 of the instrument 3100 may function in a manner similar to that of the instrument 2200. The instrument 3100 may simply provide different ergonomics and user controls.

The instruments disclosed herein with upper and lower jaws, such as the instrument 1200 and the instrument 1500, may have the ability to grasp the piece of tissue to be sutured prior to passing of the needle through the tissue. Such grasping may also be provided for instruments without such jaws like the instruments 2200 and 3000.

Figure 32:
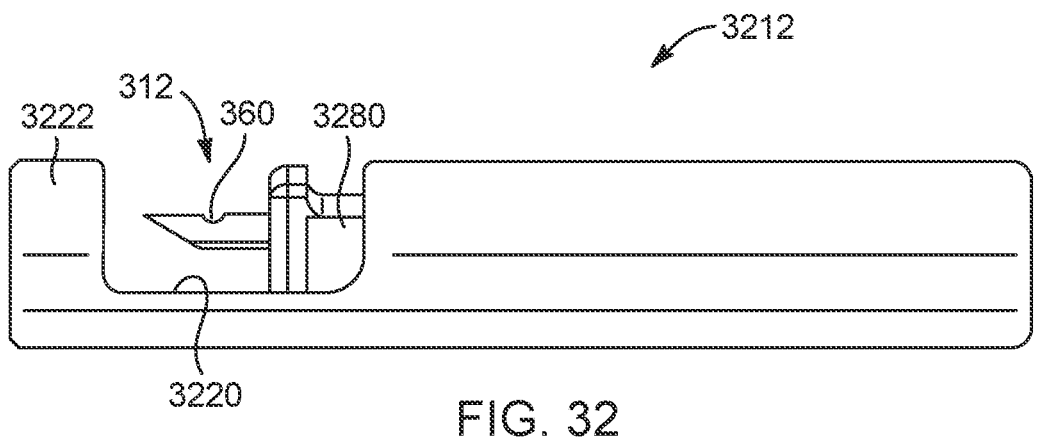
FIG. 32 is a side elevation view showing the distal end of a suture passer according to another alternative embodiment of the invention, with a proximal jaw that can be used to grasp the tissue prior to suture/needle passing.

Referring to FIG. 32, a distal end 3212 of an instrument (not shown) may have a cutout section 3220, a distal wall 3222, proximal jaw 3280 that may be used to grasp the tissue prior to suturing. The proximal jaw 3280 may extend distally in response to actuation of a user control at the proximal end (not shown) of the instrument until the section of tissue is pinched between the proximal jaw 3280 and the distal wall 3222. The distal wall 3222 may be formed as a single piece (i.e., unitarily formed) with the cutout section 3220, and may thus be a stationary feature. This may provide additional rigidity at the distal end 3212, particularly when the tissue is being pinched between the proximal jaw 3280 and the distal wall 3222. Alternatively, the distal wall 3222 may be replaced by a jaw that pivots relative to the cutout section 3220 in a manner similar to that of the jaw 2222 of FIG. 22.

A suture passing instrument according to the invention may also be used to place a continuous stitch through one or more pieces of tissue. This may be accomplished, for example, by housing two opposing needles in the distal end of the instrument. The needles may then be used to pass suture back and forth through the tissue.

Figure 33A:
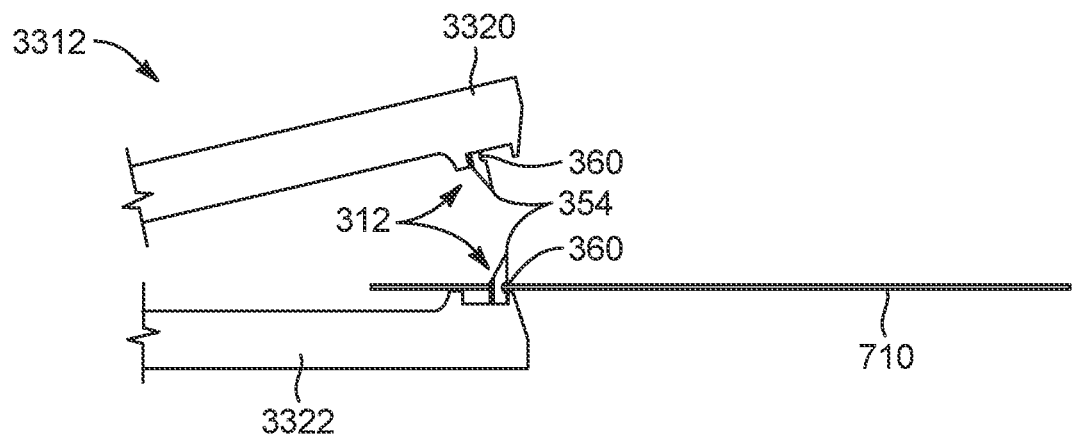
FIGS. 33A-33C are side elevation views of a distal end of a suture passer according to another alternative embodiment of the invention, showing how the two opposing needles may be used to pass suture back and forth between the top and bottom jaws.
Figure 33B:
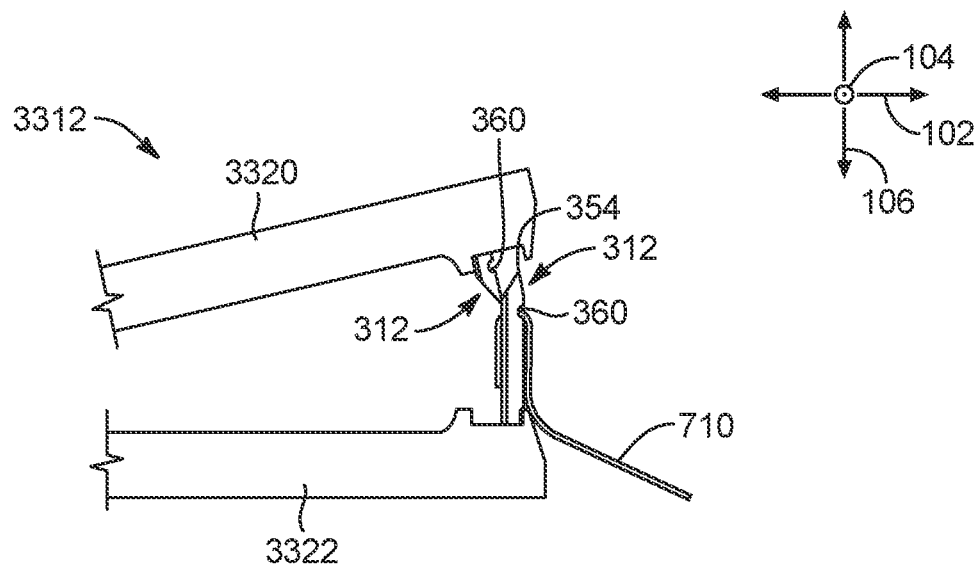
Figure 33C:
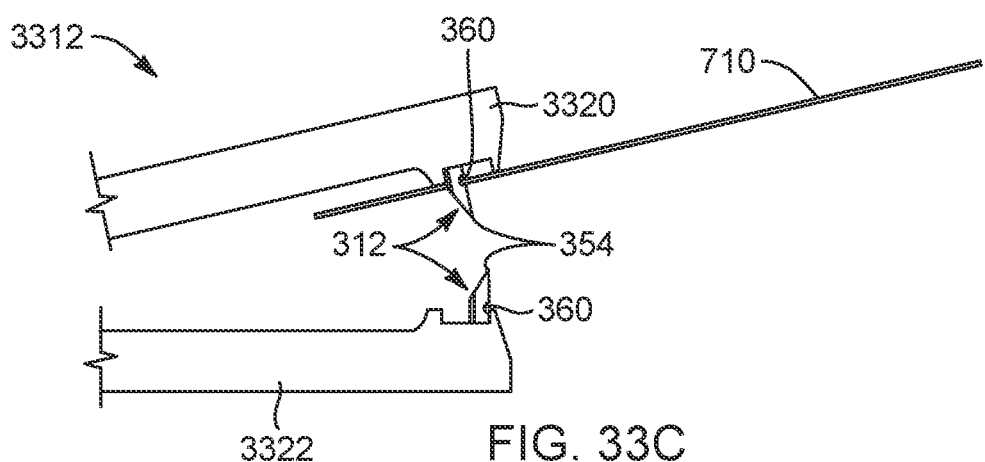

FIGS. 33A-33C illustrate a distal end 3312 of an instrument (not shown) according to another alternative embodiment, showing how a length of suture 710 may be passed from a lower jaw 3322 to an upper jaw 3320. FIG. 33A shows the suture 710 temporarily captured in the distal end 321 of a lower needle 400 housed within the lower jaw 3322.

In FIG. 33B, the distal end 312 of the lower needle 400 is extended out of the lower jaw 3322 carrying the suture 710 with it toward the upper jaw 3320. Once the distal end 312 of the lower needle 400 reaches the distal end 312 of an upper needle 400 housed in the upper jaw 3320, the suture 710 may be passed from the distal end 312 of the lower needle 400 to the distal end 312 of the upper needle 400. Additional features such as posts, wedges, pushers, or the like (not shown) may be positioned in or on the upper jaw 3320, the lower jaw 3322, and/or on the needles 400 themselves to open one or both of the channel 732 of the lower needle 400 and the channel 732 of the upper needle 400 to facilitate passage of the suture 710 from the capture hole 730 of one needle 400 to the capture hole 730 of the other needle 400.

In FIG. 33C, the lower needle 400 is retracted back into the lower jaw 3322, leaving the suture 710 in the upper needle 400. This process may then be reversed to pass the suture 710 back down from the upper jaw 3320 to the lower jaw 3322. The process may be repeated as many times as necessary to complete the continuous stitch. Each transfer of suture 710 to the opposing needle 400 may entail passage of the suture through the tissue. The distal end 3312 may be moved along the lateral direction 104 and/or the longitudinal direction 102 between each transfer so that the repeated passage of suture through the tissue defines stitching in the tissue.

As previously described in connection with FIG. 2, a flexible pusher such as the pusher 200 may be used to push or advance an implant through the body. One manner in which this may be done will be shown and described in connection with FIGS. 34-35B.

Figure 34:
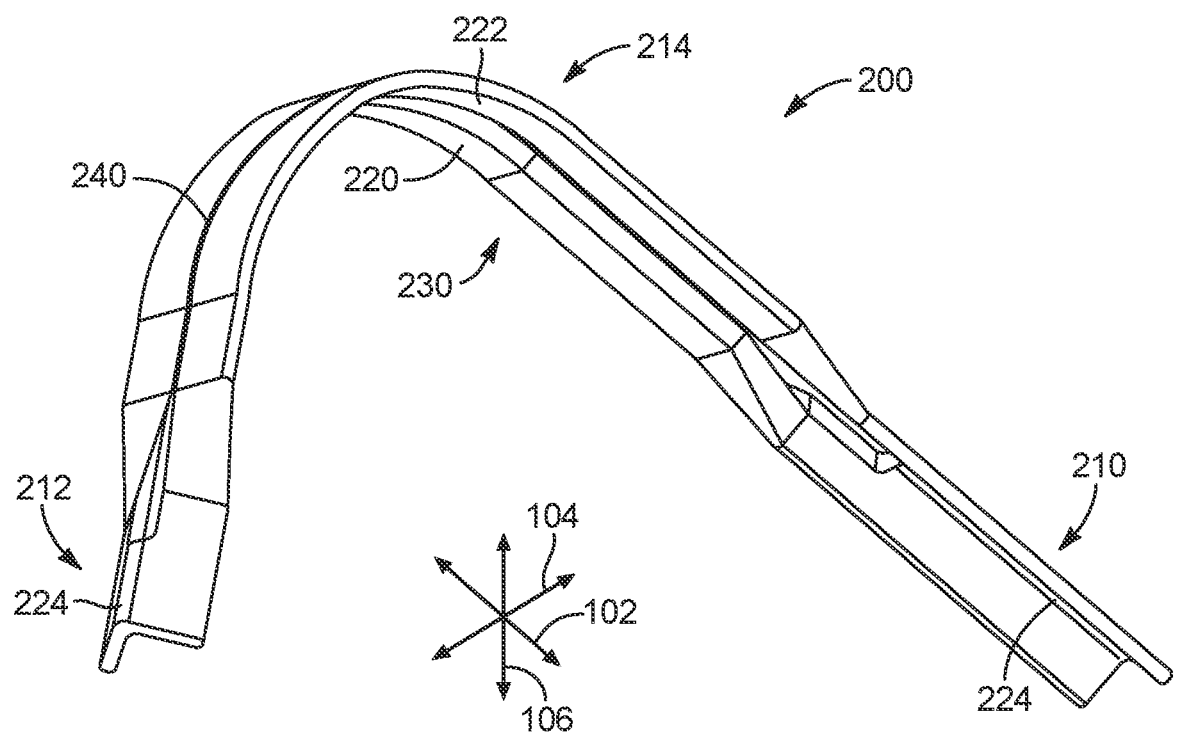
FIG. 34 is a perspective view showing how the pusher of FIGS. 2A-2D may be used to push implants or other devices along a curved pathway.

Referring to FIG. 34, a perspective view illustrates the pusher 200 is shown with a downward bend like that illustrated in FIG. 8 in connection with the needle 400. The proximal end 210 and the distal end 212 of the pusher 200 may retain the V-shaped cross-sectional shape shown in FIG. 2B, while the slot 240 may allow the first arm 220 and the second arm 222 of the pusher 200 to rotate into a substantially coplanar configuration as in FIG. 2C. Thus, the selectively bendable portion 230 may bend in the transverse direction 106.

The cross-sectional shape at the distal end 212 may be modified in a variety of ways, including the use of V-shaped, round, rectangular, square, oval, star, or hexagonal cross-sectional shapes. The shape at the distal end 212 may be dependent upon the implant it is designed to manipulate. In certain embodiments, the distal end 212 may have an implant interface (not shown) with various features that grip, interlock, or otherwise adhere to the implant until release is desired. The implant interface may include an active or passive connection mechanism including press-fits, collets, or tongue-groove systems, bayonet fittings, or any implant interface known in the art.

Figure 35A:
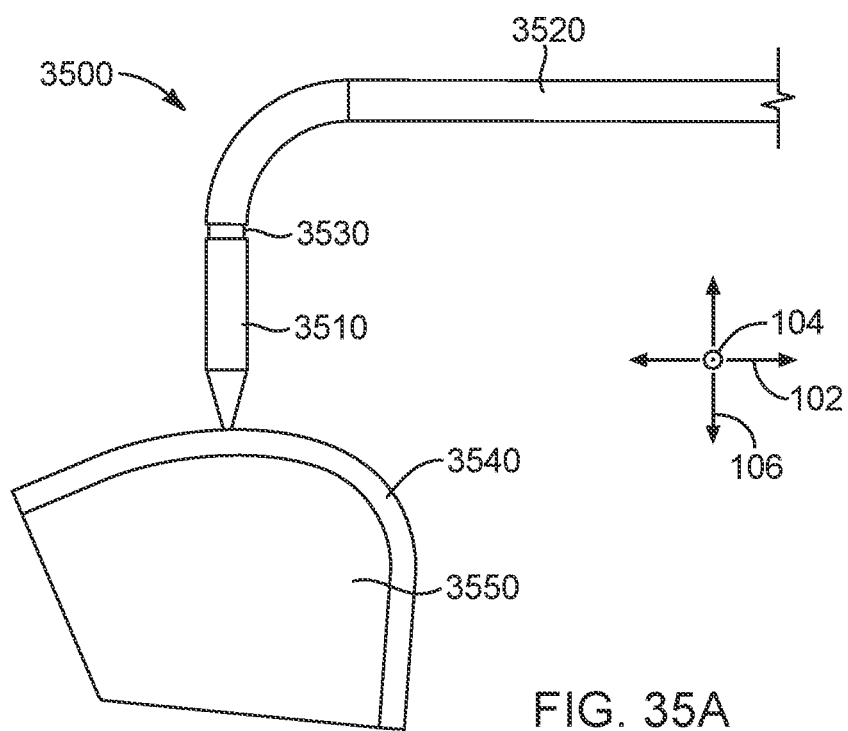
FIGS. 35A-35B are side elevation views showing how a pusher and a hollow shaft of an instrument according to an alternative embodiment may be used to insert a bone anchor into a bony surface along a nonlinear pathway.
Figure 35B:
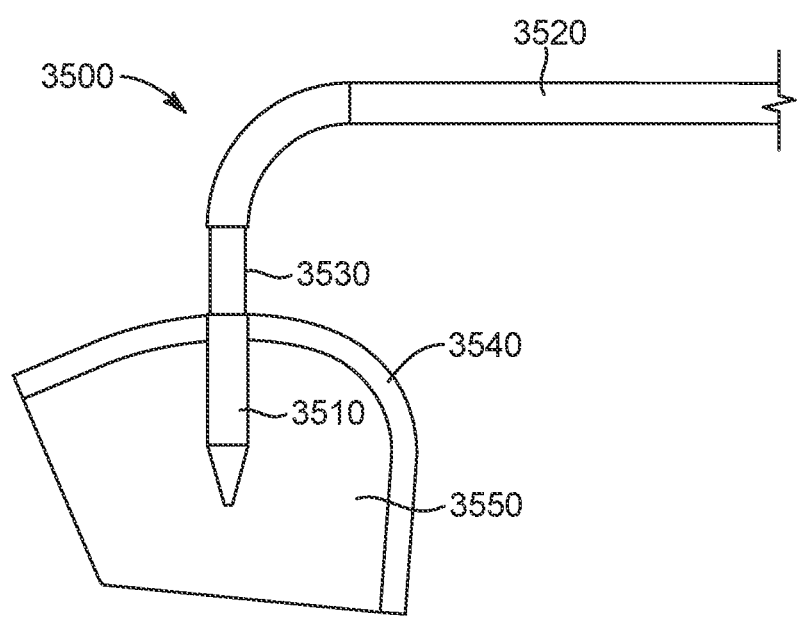

FIGS. 35A-35B demonstrate how a pusher 3500 according to another embodiment of the invention may be used to insert an implant in the form of a bone anchor 3510 along a curved insertion pathway to reach a desired location. A hollow shaft 3520 may house a pusher 3530, which may be flexible like the pusher 200 of FIGS. 2A-2D. The distal tip of the pusher 3530 may interface with the bone anchor 3510, which may be designed to be pushed into bone.

In FIG. 35A, the pusher 3530 may initially be retracted within the hollow shaft 3520. The bone anchor 3510 may be placed on the surface of a cortical layer 3540 of the bony implantation site. The pusher 3530 may then be pushed or extended through the hollow shaft 3520 using an actuator (not shown) on or proximate the hollow shaft 3520 to push the bone anchor 3510 through the cortical layer 3540 and into a cancellous layer 3550 of bone as shown in FIG. 35B. If desired, one or more features such as clips, clamps, bone screws, or the like may be used to temporarily dock hollow shaft 3520 to the cortical layer 3540 so that a counter force can be applied to the cortical layer 3540 as the bone anchor 3510 is driven through it.

Figure 36A:
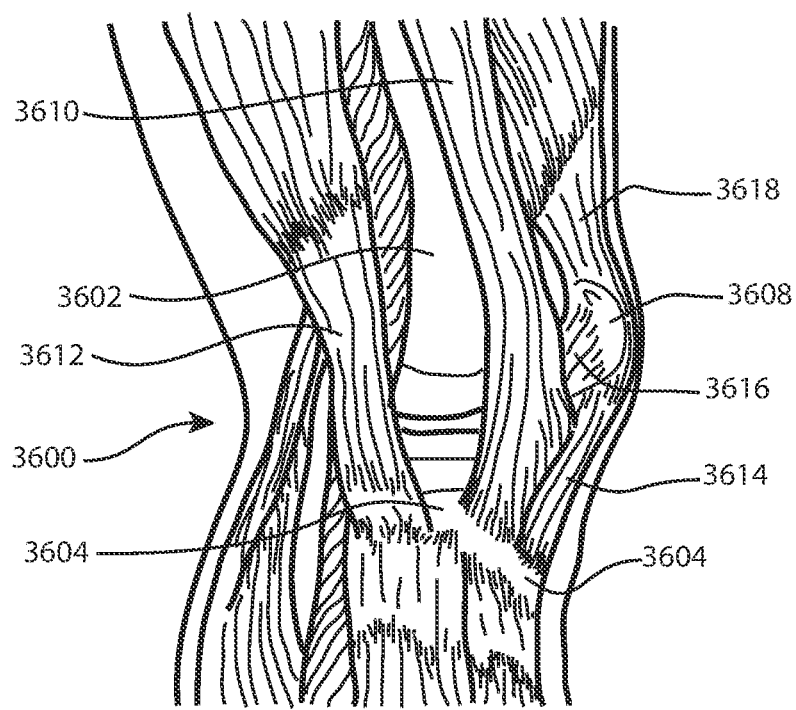
FIG. 36A is a side view of a human knee joint in an extended position.
Figure 36B:
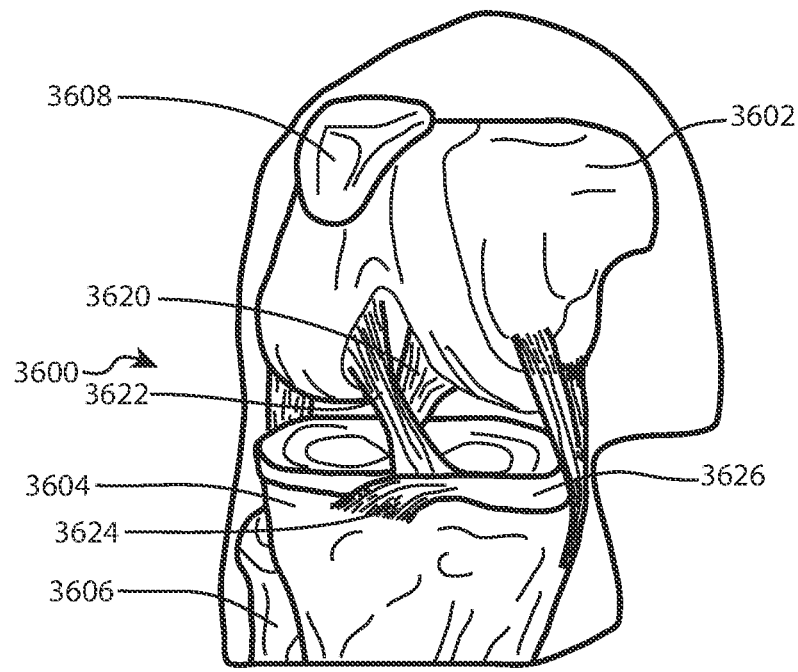
FIG. 36B is a perspective view of a human knee joint in a flexed position.
Figure 37:
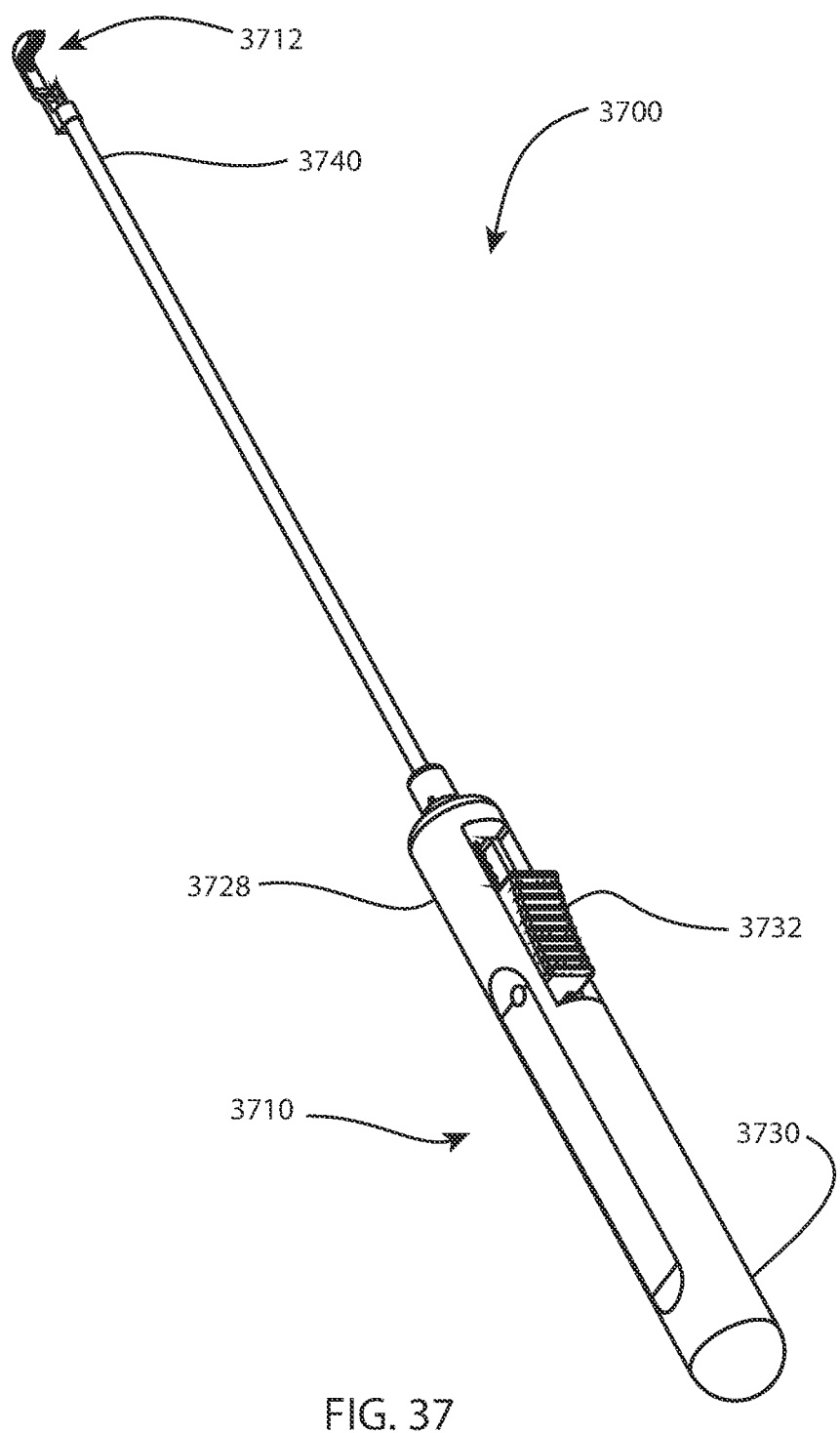
FIG. 37 is a perspective view of another suture passer.

Referring to FIGS. 36A-B, a human knee joint 3600 is shown in an extended position and a flexed position, respectively. The knee joint 3600 includes a femur 3602, a tibia 3604, and a patella 3608. A fibula 3606 is also shown in its anatomic relationship to the knee joint 3600. The knee joint 3600 also includes, or is proximate to, an iliotibial band 3610, a hamstring tendon 3612, a patellar tendon 3614, a lateral patellar retinaculum 3616, a quadriceps tendon 3618, a posterior cruciate ligament 3620, an anterior cruciate ligament 3622, a meniscal ligament 3624, and a meniscus 3626. The meniscus 3626 lies between complementary articular surfaces of the femur 3602 and the tibia 3604.

Referring to FIGS. 37-40, another instrument 3700 is shown. Instrument 3700 may also be a suture passer, and may be suitable for passing suture through tissue anywhere in the body, such as the meniscus 3626 in the knee 3600. The instrument 3700 may have a proximal end 3710, a distal end 3712, and an intermediate portion 3714 between the proximal end 3710 and the distal end 3712. The instrument 3700 may use a rigid needle 3716 to pass suture through tissue.

The proximal end 3710 may have a straight style handle 3730. The handle 3730 may be used with a wide variety of user controls including push buttons, sliders, levers, triggers, or other similar controls. The proximal end 3710 includes a chassis 3728 that generally contains the mechanical workings (not shown) of the instrument 3700. A first user control 3732 may take the form of a slider 3732. The slider 3732 may control actuation of a needle 3716 through the instrument 3700. The instrument 3700 may be used with a single hand, with the handle 3730 held in the palm of the user's hand, and the slider 3732 actuated by the thumb on the same hand.

Figure 38:
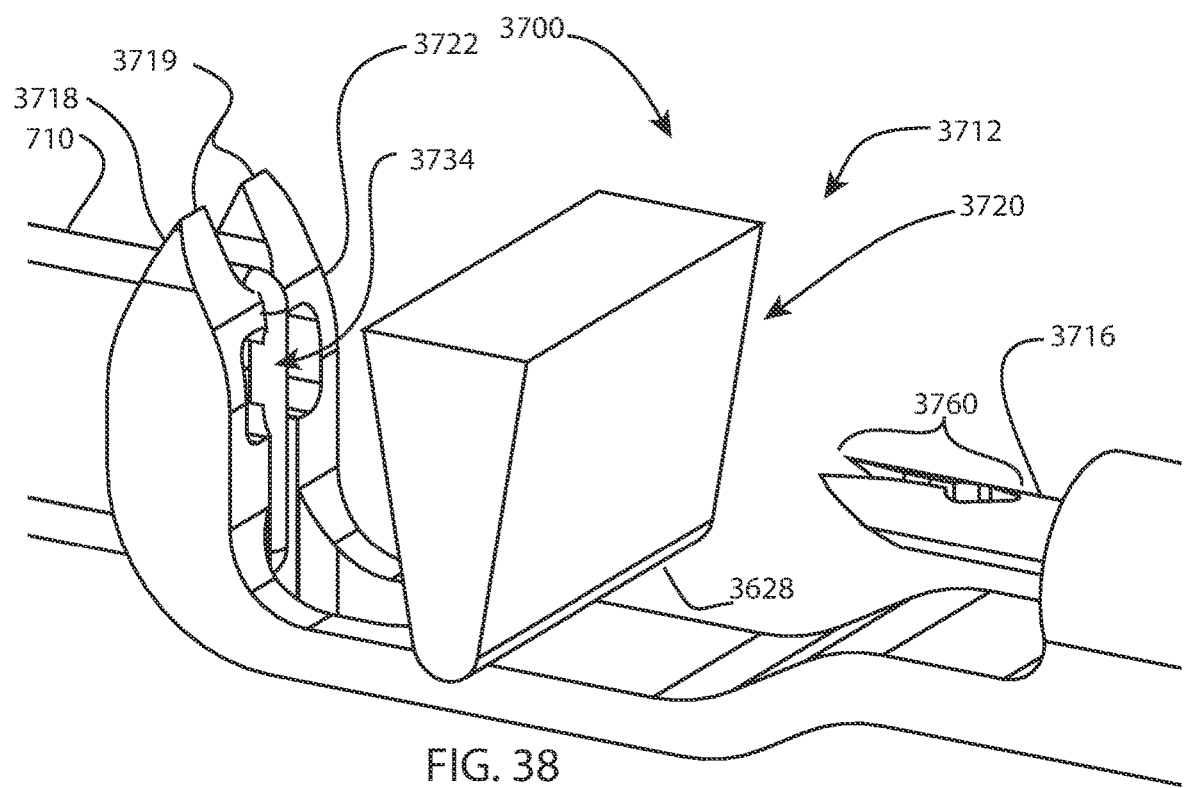
FIG. 38 is a perspective detail view of a distal tip portion of the suture passer of FIG. 37, a suture, and a tissue portion, with a needle of the suture passer in a partially retracted position.

Referring to FIGS. 38-41A, the distal end 3712 may have a cutout section 3720 and a distal wall 3722. The cutout section 3720 may provide a location for tissue to be inserted between the at least partially retracted needle 3716 and the distal wall 3722 (FIG. 38). The distal wall 3722 may be oriented transversely to, or generally perpendicular to, the intermediate portion 3714, in other words forming an angle of 45° to 135° with respect to the longitudinal axis of the intermediate portion 3714. FIG. 38 shows a distal wall 3722 which is substantially perpendicular to the intermediate portion 3714. The distal wall 3722 may be formed as a single piece (i.e., unitarily formed) with the cutout section 3720, and may thus be a stationary feature. This may provide additional rigidity at the distal end 3712, particularly when the tissue is being pinched between the needle tip and the distal wall 3722. Alternatively, the distal wall 3722 may be replaced by a jaw that pivots relative to the cutout section 3720 in a manner similar to that of the jaw 2222 of FIG. 22. A window 3734 may extend at least partially through the distal wall 3722 to accommodate passage of the distal end of the needle 3716 in line with the intermediate portion 3714. The window 3734 may extend longitudinally as shown, and may extend laterally through the distal wall 3722 in one or two dimensions, i.e., the height and/or width of the distal wall. The distal end of the window 3734 may have a central post 3736 (FIG. 41A) that can be used to support the suture 710 and may be used to spread the suture capture feature 3760 on the needle 3716 as previously described. In some examples, the post 3736 may stand alone, meaning that there is no distinct window framed by distal wall material. A slot 3738 may be provided to temporarily capture a section of a suture such as the suture 710. The slot 3738 may extend across a proximal face of the window 3734, and may be narrower than an uncompressed diameter of the suture 710. The narrow width of the slot 3738 may enable the slot 3738 to securely hold the suture 710 to temporarily capture it, while remaining able to release the suture 710 in response to application of a small removal force, such as that applied to the suture 710 such as when it is being retrieved by the needle 3716. The slot 3738 may optionally have a boss or other positive feature (not shown) such as a bump, wedge, or bulge that provides a secondary constraint on the suture. The window 3734, post 3736, and/or slot 3738 may together or separately be referred to as a suture holding feature or a target for the needle 3716. The distal wall 3722 may terminate in a distal tip 3718 which may include a sharp, blade-like extension 3719 that may be used to cut into or through various tissues such as tendons or ligaments. FIG. 41A shows a blade-like extension 3719 which is divided into two portions by the slot 3738, wherein the blade-like extension 3719 is beveled on two sides. This distal tip configuration may be included in any of the distal ends disclosed herein.

The intermediate portion 3714 may be similar to the intermediate portions 2214, 1214, or other intermediate portions disclosed herein. The intermediate portion 3714 may have a shaft 3740 that is of adequate length such that the handle 3730 and the chassis 3728 may remain outside the body while the distal end 3712 is inserted through a working portal or cannula to reach a joint space, a wound, or another anatomical region that requires suturing.

Referring to FIGS. 38-40 and 42A, the needle 3716 may be like the needle 300 of FIGS. 3A-3C, or it may have an arcuate or U-shaped cross-sectional shape like the implant manipulator 550 of FIG. 5B. A needle 3716 with an arcuate cross-sectional shape is illustrated. The needle 3716 includes a suture capture feature 3760 which may be similar to or identical to the suture capture feature 360 of needle 300 shown in FIG. 7A or other suture capture features disclosed herein. The suture capture feature 3760 may include a first member 3750, a second member 3752, a capture hole 3754, and a channel 3756 that extends between the first member 3750 and the second member 3752 to provide access to the capture hole 3754. The first member 3750 and the second member 3752 may be distally sharpened to easily pierce tissue. The needle 3716 and/or slider 3732 may be spring loaded or spring biased to remain in, and to return to, a retracted position except when the slider is urged distally to actuate, or move, the needle distally toward an extended position of the needle. The needle 3716 may reside completely, or at least partially, within the interior of the intermediate portion 3714 proximal to the cutout section 3720. The needle 3716 is in a partially retracted position when the distal tip of the needle is in the proximal half of the cutout section 3720, and is in a partially extended position when the distal tip of the needle is in the distal half of the cutout section.

Figure 39:
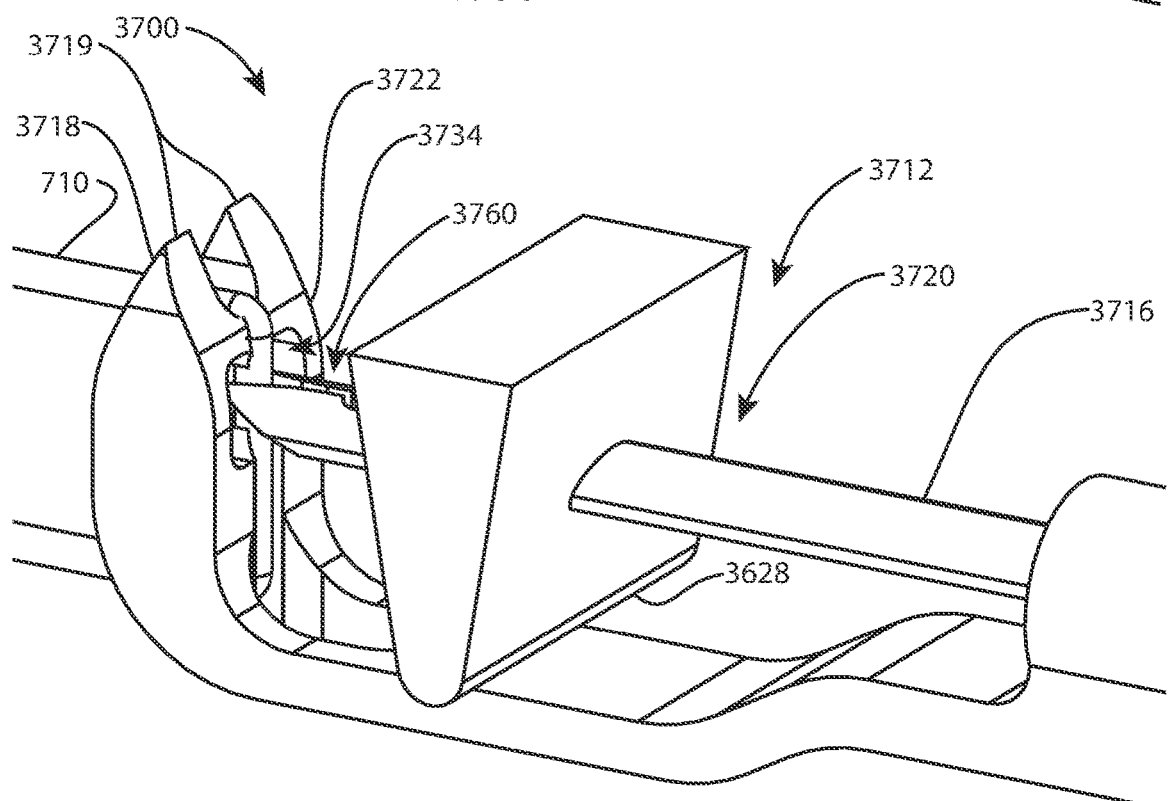
FIG. 39 is a perspective detail view of the distal tip portion of the suture passer, the suture, and the tissue portion of FIG. 38, with the needle of the suture passer in an extended position passing through the tissue portion.

Referring to FIGS. 38-40, a method of using instrument 3700 may include some or all of the following steps: loading the suture 710 in the slot 3738; manipulating the instrument 3700 to position a tissue portion 3628 in the cutout section 3720 (FIG. 38); actuating the needle 3716 to penetrate the tissue portion 3628 (FIG. 39) and push the suture 710 into the suture capture feature 3760; retracting the needle 3716 to a retracted position, pulling the suture 710 with it (FIG. 40); and removing the instrument 3700 from the body, pulling the suture 710 with it.

In FIG. 38, a strand of suture 710 is shown temporarily constrained within the slot 3738. The suture 710 may be pre-loaded into the slot 3738 of the instrument 3700 prior to use. The distal end 3712 of the instrument 3700 and the suture 710 may be inserted together into a desired location where suturing is to be performed, such as an intra-articular space in the knee joint 3600 between the distal femur 3602 and the meniscus 3626. The distal end 3712 and suture 710 may pass through a cannula or other portal to access the desired location. The proximal end 3710 may remain outside the body, or at least outside the suturing location. Once in the desired location, the distal end 3712 and suture 710 may be manipulated, moved, positioned, or otherwise oriented so that a tissue portion 3628 is within the cutout section 3720 between the retracted needle 3716 and the distal wall 3722.

In FIG. 39, the needle 3716 is shown in an extended position in which the needle 3716 has pierced the tissue 3628, the first member 3750 and the second member 3752 are received in the window 3734, and the suture 710 has entered the channel 3756. This state may be achieved by pushing the slider 3732 distally, thus advancing the needle 3716 distally through the tissue 3628 and at least partially into the window 3734. Pushing the slider 3732 farther distally advance the needle 3716 farther distally, and causes the suture 710 to migrate along the channel 3756 into the capture hole 3754. When the suture 710 is received in the channel 3756 and/or capture hole 3754, the needle 3716 is in the fully extended position.

As discussed previously, once the suture 710 is in the capture hole 3754, or captured in an intermediate or proximal section of the channel 3756, the needle 3716 can pull the suture 710 out of the slot 3738 and carry the suture with the needle as the needle is retracted. This state is illustrated in FIG. 40, which shows that the suture 710 has been released from the slot 3738 and pulled through the tissue 3628 by the retracting needle 3716. Retracting the needle 3716 may involve sliding the slider 3732 proximally, or simply releasing distal pressure on the slider 3732 to allow the spring bias to return the needle to the retracted position.

The instrument 3700 may then be removed from the suturing location, and may be removed from the body, pulling the suture 710 with it. The suture 710 may be removed from the suture capture feature 3760.

Another portion of the same suture 710, or a different suture, may be loaded into the slot 3738 of the instrument 3700, and the preceding process repeated at different locations on the tissue portion 3628 until the desired number of stitches are in place. Knots may be tied periodically to stabilize the stitches and/or the tissue 3628.

In one example, the preceding process may be executed a first time to pass a first free end of the suture 710 through a tissue 3628 to protrude from a first side of the tissue, the remainder of the suture 710 extending from the opposite side of the tissue. The preceding process may be executed a second time to pass a second free end of the suture 710 through a separate location in the tissue 3628 to protrude from the first side of the tissue beside the first free end of the suture 710, the remaining middle portion of the suture 710 forming a loop extending from the opposite side of the tissue. The first and second free ends of the suture 710 may be tied in a knot against the first side of the tissue 3628 to form a stitch. Multiple independent stitches may be placed in various locations in the tissue by repeating the steps in this paragraph for each independent stitch. One of skill in the art will appreciate the many types of stitches that may be created by passing suture through tissue with the instrument 3700.

Referring to FIG. 41B, another example of a distal end 4112 is shown for use with instrument 3700 or 4800, or other similar instruments disclosed herein. The distal end 4112 may have a cutout section 4120 and a distal wall 4122. The cutout section 4120 may provide a location for tissue to be inserted between an at least partially retracted needle and the distal wall 4122. The distal wall may be oriented transversely to, or generally perpendicular to, the intermediate portion, in other words forming an angle of 45° to 135° with respect to the longitudinal axis of the intermediate portion. FIG. 41B shows a distal wall 4122 which is substantially perpendicular to the intermediate portion. The distal wall 4122 may be formed as a single piece (i.e., unitarily formed) with the cutout section 4120, and may thus be a stationary feature. This may provide additional rigidity at the distal end 4112, particularly when the tissue is being pinched between a needle tip and the distal wall 4122. Alternatively, the distal wall 4122 may be replaced by a jaw that pivots relative to the cutout section 4120 in a manner similar to that of the jaw 2222 of FIG. 22. A window 4134 may extend at least partially through the distal wall 4122 to accommodate passage of the distal end of the needle 4116 in line with the intermediate portion. The window 4134 may extend longitudinally as shown, and may extend laterally through the distal wall 4122 in one or two dimensions, i.e., the height and/or width of the distal wall. The distal end of the window 4134 may have a central post 4136 (not shown) that can be used to support the suture 710 and may be used to spread the suture capture feature 4160 on the needle 4116 as previously described. In some examples, the post 4136 may stand alone, meaning that there is no distinct window framed by distal wall material. A slot 4138 may be provided to temporarily capture a section of a suture such as the suture 710. The slot 4138 may extend across a proximal face of the window 4134, and may be narrower than an uncompressed diameter of the suture 710. The narrow width of the slot 4138 may enable the slot 4138 to securely hold the suture 710 to temporarily capture it, while remaining able to release the suture 710 in response to application of a small removal force, such as that applied to the suture 710 such as when it is being retrieved by the needle 4116. The slot 4138 may optionally have a boss or other positive feature (not shown) such as a bump, wedge, or bulge that provides a secondary constraint on the suture. The window 4134, post 4136, and/or slot 4138 may together or separately be referred to as a suture holding feature or a target for the needle 4116. The distal wall 4122 may terminate in a distal tip 4118 which may include a sharp, blade-like extension 4119 that may be used to cut into or through various tissues such as tendons or ligaments. FIG. 41B shows a blade-like extension 4119 which is divided into two portions by the slot 4138, wherein the blade-like extension 4119 is beveled on one side, the proximal side facing the cutout section 4120. This distal tip configuration may be included in any of the distal ends disclosed herein.

Figure 42A:
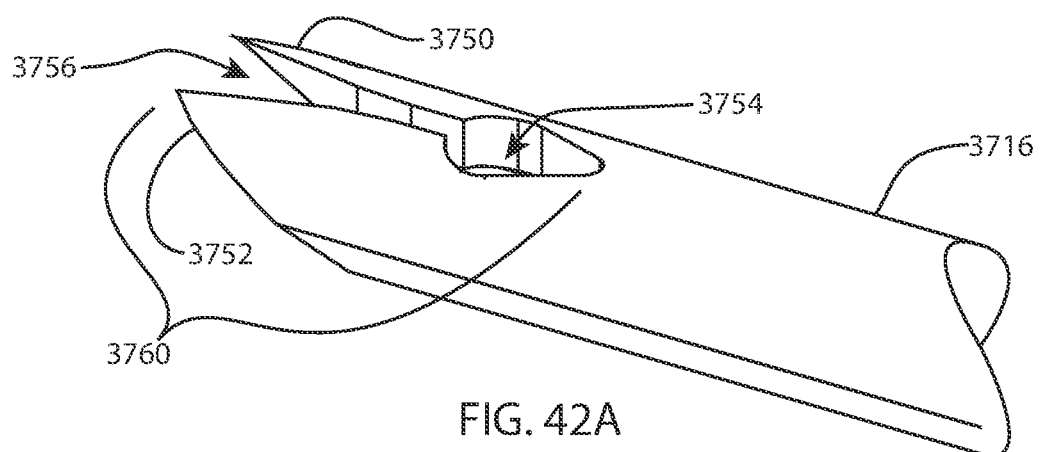
FIG. 42A is a perspective view of the needle of the suture passer of FIG. 37.
Figure 42B:
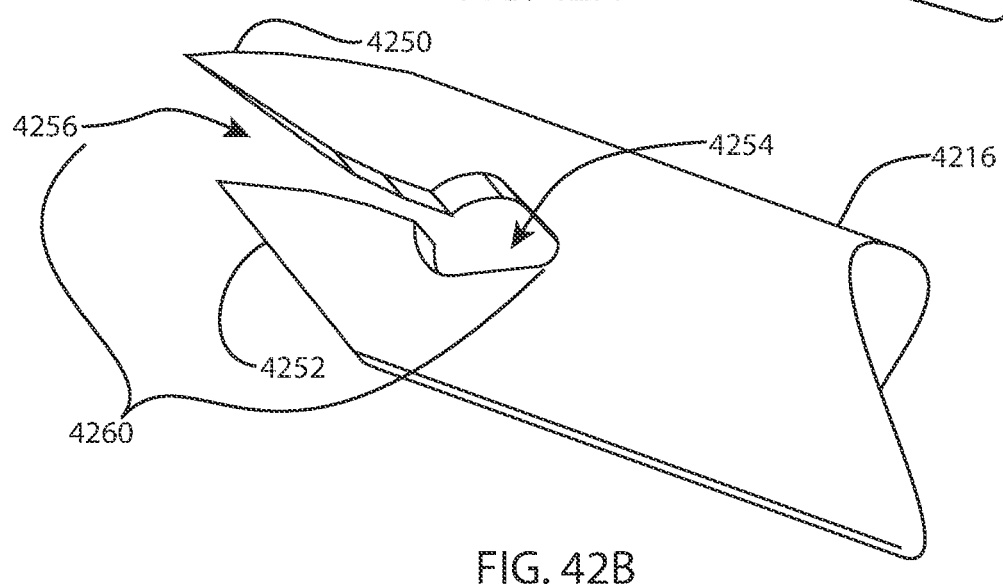
FIG. 42B is a perspective view of another needle for a suture passer.

Referring to FIG. 42B, another example of a needle 4216 is shown for use with the instruments disclosed herein. The needle 4216 may be like the needle 300 of FIGS. 3A-3C, or it may have an arcuate or U-shaped cross-sectional shape like the implant manipulator 550 of FIG. 5B. A needle 4216 with an arcuate cross-sectional shape is illustrated. The needle 4216 includes a suture capture feature 4260 which may be similar to or identical to the suture capture feature 360 of needle 300 shown in FIG. or other suture capture features disclosed herein. The suture capture feature 4260 may include a first member 4250, a second member 4252, a capture hole 4254, and a channel 4256 that extends between the first member 4250 and the second member 4252 to provide access to the capture hole 4254. The first member 4250 and the second member 4252 may be distally sharpened to easily pierce tissue. In this example, the first member 4250 is longer than the second member 4252. This may be beneficial as the force required to pierce the tissue may be reduced since only one sharp edge initially needs to penetrate through the tissue instead of two. Once the first tissue piercing edge of member 4250 has passed through the tissue the second tissue piercing edge of member 4252 may more easily pass through the initial cut in the tissue formed by the passage of the first edge. The needle 4216 and/or slider 4232 may be spring loaded or spring biased to remain in, and to return to, a retracted position except when the slider is urged distally to actuate, or move, the needle distally toward an extended position of the needle. The needle 4216 may reside completely, or at least partially, within the interior of the intermediate portion 4214 proximal to the cutout section 4220.

Figure 43:
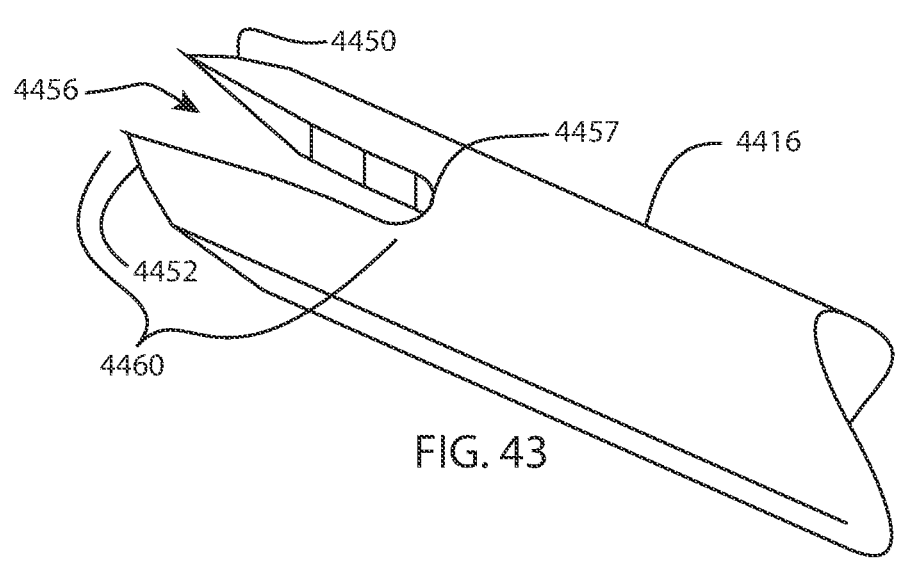
FIG. 43 is a perspective view of yet another needle for a suture passer.

Referring to FIG. 43, yet another example of a needle 4416 is shown for use with the instruments disclosed herein. The needle 4416 may be like the needle 300 of FIGS. 3A-3C, or it may have an arcuate or U-shaped cross-sectional shape like the implant manipulator 550 of FIG. 5B. A needle 4416 with an arcuate cross-sectional shape is illustrated. The needle 4416 includes a suture capture feature 4460 which may share some features with the suture capture feature 360 of needle 300 shown in FIG. 7A or other suture capture features disclosed herein. The suture capture feature 4460 may include a first member 4450, a second member 4452, and a channel 4456 that extends between the first member 4450 and the second member 4452. The illustrated suture capture feature 4460 may lack a distinct capture hole, instead the channel 4456 may terminate in a full radius 4457 or a squared end. The first member 3750 and the second member 3752 may be distally sharpened to easily pierce tissue. The channel 4456 may be narrower than the uncompressed diameter of the suture 710 so that the channel 4456 receives the suture 710 with a frictional fit and releases the suture 710 when tension is applied to the suture 710. This arrangement may be suitable when the needle is to be used to push suture through tissue instead of pulling suture through tissue as with needle 300. The needle 4416 and/or slider 4432 may be spring loaded or spring biased to remain in, and to return to, a retracted position except when the slider is urged distally to actuate the needle distally toward an extended position of the needle. The needle 4416 may reside completely, or at least partially, within the interior of the intermediate portion 4414 proximal to the cutout section 4420.

Figure 44:
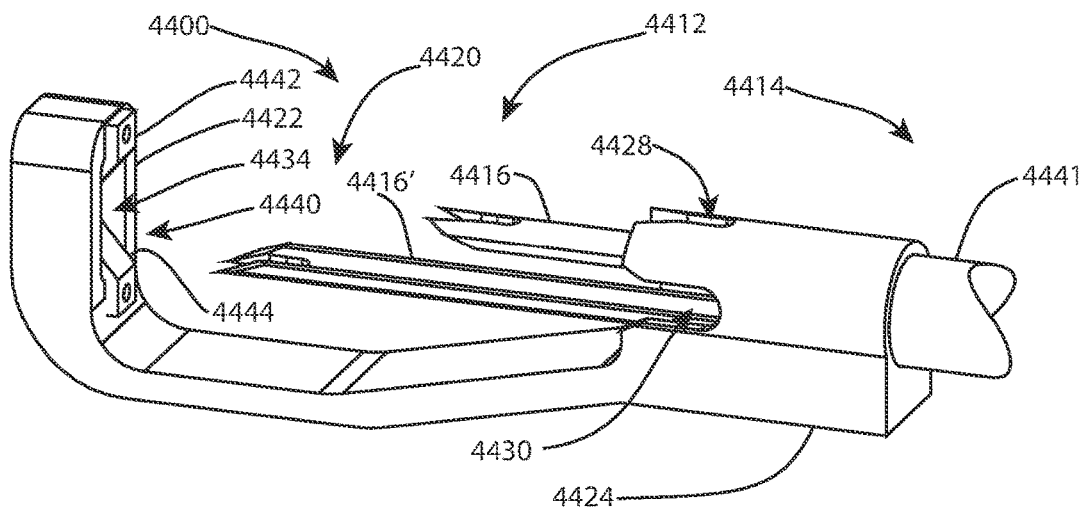
FIG. 44 is a perspective view of a distal tip portion of yet another suture passer, with a first needle of the suture passer in a partially retracted position and a second needle of the suture passer in a partially extended position.

Referring to FIG. 44, a distal portion of yet another instrument 4400 is shown. Instrument 4400 may also be a suture passer, and may be suitable for passing suture through tissue anywhere in the body, such as the meniscus 3626 in the knee 3600. The instrument 4400 may have a proximal end 4410 (not shown), a distal end 4412, and an intermediate portion 4414 between the proximal end 4410 and the distal end 4412. The proximal end 4410 may be identical to any of the proximal ends disclosed herein. The instrument 4400 may use the rigid needle 4416 of FIG. 43 to pass suture through tissue. This example shows that two or more needles may be included in the instrument 4400, or any of the instruments disclosed herein, including those instruments for which only the distal end is discussed.

Referring to FIGS. 44-47, the distal end 4412 may have a cutout section 4420, a distal wall 4422, and a base 4424 opposite the distal wall 4422. The cutout section 4420 may be between the distal wall 4422 and the base 4424. The cutout section 4420 may provide a location for tissue to be inserted between the at least partially retracted needles 4416, 4416' and the distal wall 4422. The distal wall 4422 may be formed as a single piece (i.e., unitarily formed) with the cutout section 4420, and may thus be a stationary feature. This may provide additional rigidity at the distal end 4412, particularly when the tissue is being pinched between the needle tip and the distal wall 4422. Alternatively, the distal wall 4422 may be replaced by a jaw that pivots relative to the cutout section 4420 in a manner similar to that of the jaw 2222 of FIG. 22. A window 4434 may extend at least partially through the distal wall 4422 to accommodate passage of the distal end of the needle 4416. The window 4434 may extend longitudinally as shown, and may extend laterally through the distal wall 4422 in one or two dimensions, i.e., the height and/or width of the distal wall.

Figure 47:
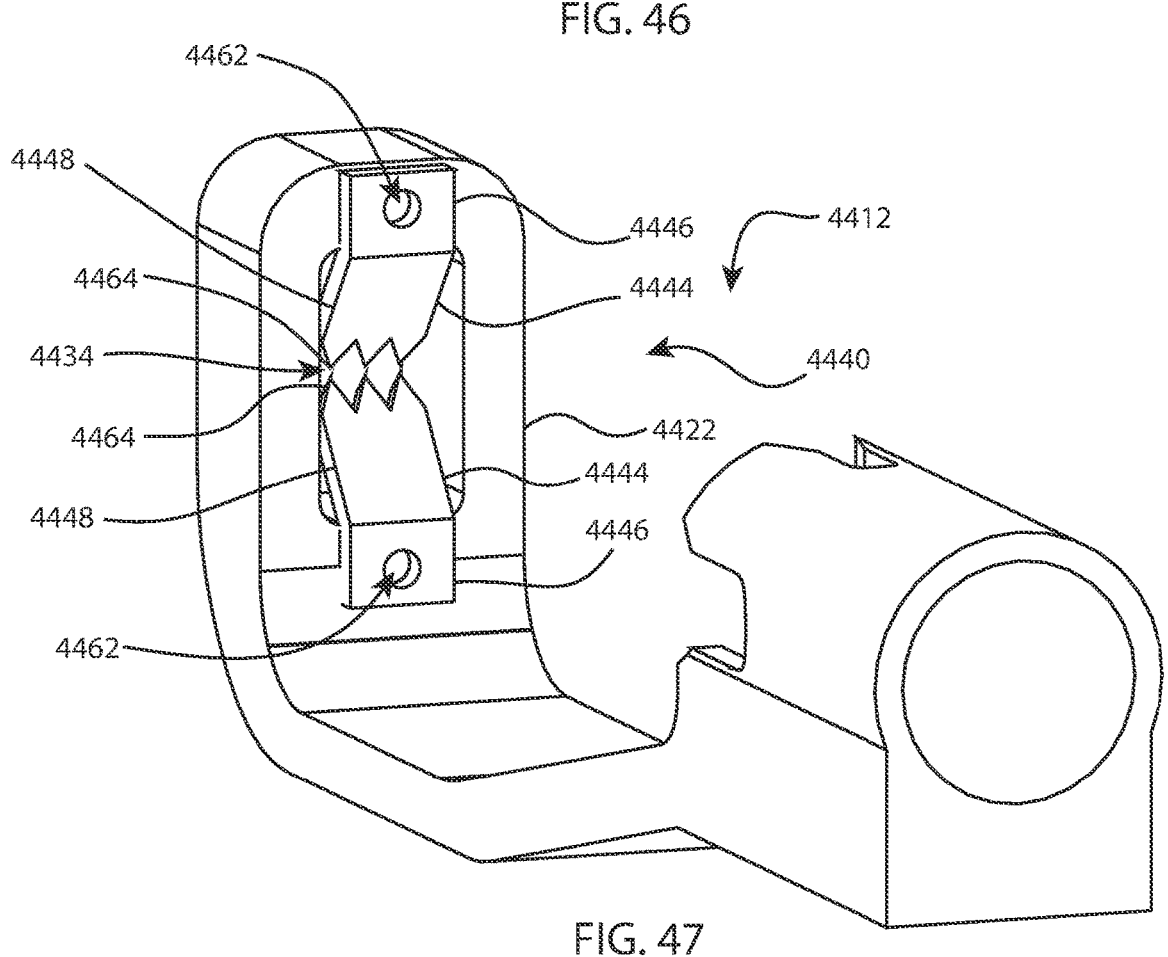
FIG. 47 is a perspective view of a portion of the distal portion of the suture passer of FIG. 44, showing a suture capture mechanism.

The distal end 4412 may include a suture capture feature 4440, as seen best in FIG. 47. The suture capture feature 4440 may be in or near the window 4434; in the illustrated example, some portions of the suture capture feature 4440 extend into the window 4434 and other portions of the suture capture feature 4440 are adjacent to the window 4434. The suture capture feature 4440 receives and retains suture, and may be similar to, or identical to, other suture capture features disclosed herein. In the illustrated example, the suture capture feature 4440 includes at least one suture capture element 4442, and is shown with two suture capture element 4442, 4444 in a facing relationship. Each suture capture element includes a base 4446 and a tab 4448 which extends obliquely from the base 4446. The illustrated base 4446 and tab 4448 are both plate-like elements, and the suture capture elements 4442, 4444 may be stamped or cut from sheet metal. The base 4446 may include a hole 4462. The tab 4448 may include a gripping end 4464 opposite the base 4446. The gripping end 4464 may include roughening, teeth, serrations, ridges, grooves, hooks, adhesive, silicone, or other feature, treatment, coating, or modification to enhance the ability to grip and retain suture. Teeth are shown along the gripping ends 4464 in FIG. 47. Each suture capture element 4442, 4444 is coupled to the distal end 4412 so that the base 4446 is adjacent to the window 4434 and the tab 4448 extends obliquely from the base 4446 into the window 4434. Furthermore, the suture capture elements 4442, 4444 are coupled to the distal end 4412 on opposite sides of the window 4434 so that the gripping ends 4464 are facing each other. The tabs 4448 may be directionally biased, as shown, so that the advancing tip of a needle easily pushes the tabs aside, but the tabs close upon and grasp the suture as the needle is withdrawn. In some examples, the suture capture feature 4440 may stand alone, meaning that there is no distinct window framed by distal wall material. In one such example, the suture capture feature 4440 may include suture capture element 4444 alone. In another such example, the suture capture feature 4440 may include suture capture element 4442, 4444 in a facing relationship, but rotated 90° from the orientation shown in FIG. 47.

The window 4434, suture capture feature 4440, and/or suture capture element 4442, 4444 may together or separately be referred to as a suture holding feature or a target for the needle 4416.

Figure 45:
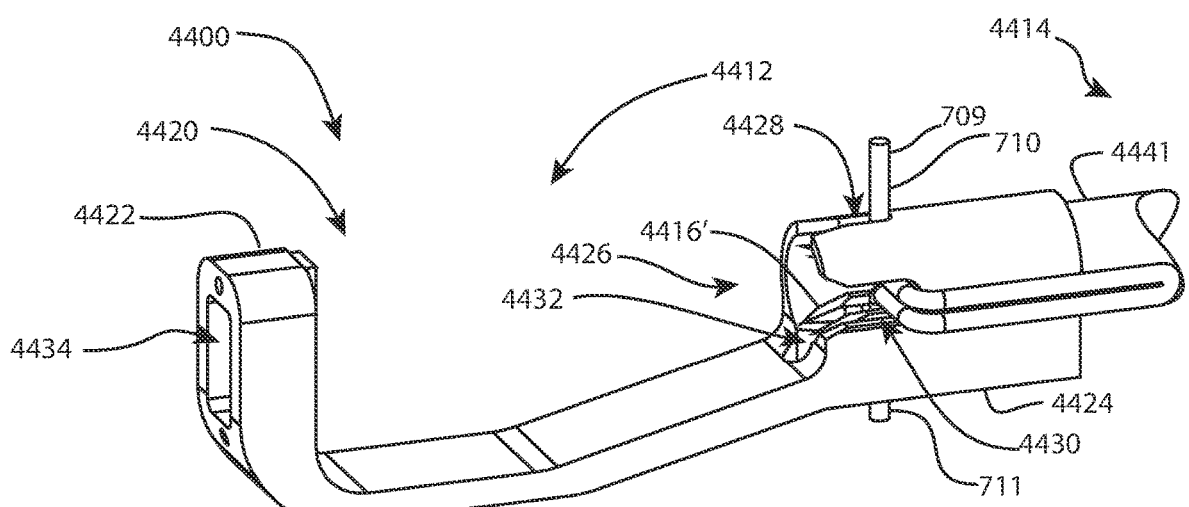
FIG. 45 is a perspective view of the distal portion of the suture passer of FIG. 44 with a suture.
Figure 46:
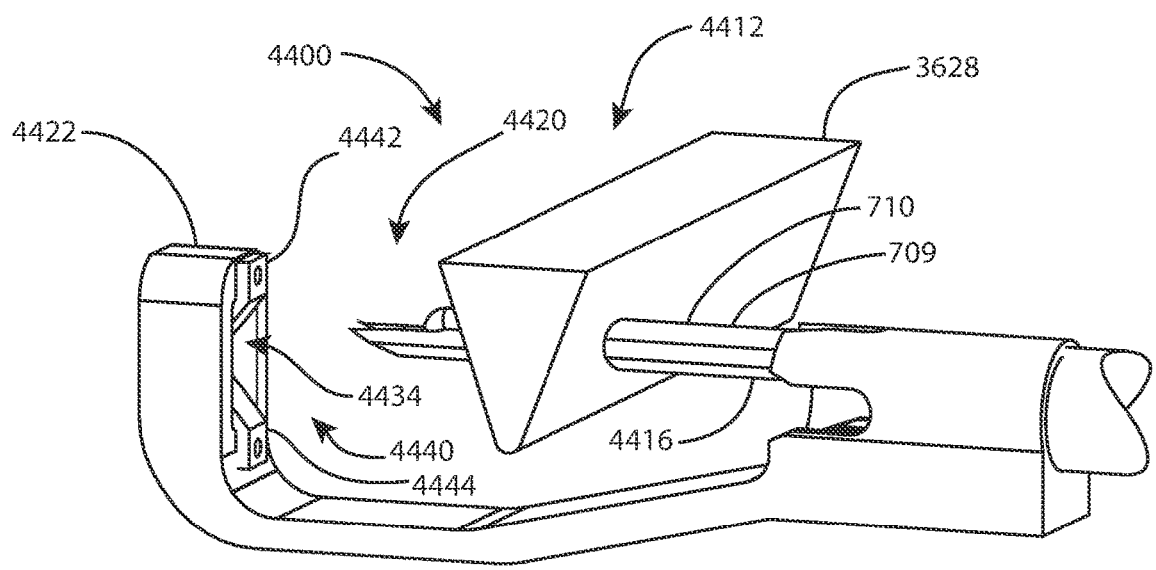
FIG. 46 is a perspective view of the distal portion of the suture passer of FIG. 44 with the first needle in a partially extended position, the suture carried by the first needle.

The distal end 4412 may include a hole 4426 extending longitudinally through the base 4424. The base 4424 may also include at least one slot, hole, or other feature that receives suture. In FIG. 45, three slots 4428, 4430, 4432 are shown arranged around the hole 4426. At least one of the slots 4428, 4430, 4432 may be aligned with, or coaxial with, a needle channel; in the example, slots 4428, 4432 are aligned with, or coaxial with, channels 4456, 4456'. The slots 4428, 4430, 4432 may be wider than, equal to, or narrower than the uncompressed diameter of the suture. The base 4424 is fixedly coupled to the intermediate portion

4414, and thus may be considered part of the intermediate portion 4414. Any of the distal ends disclosed herein may include a base with a hole and/or suture receiving feature(s) like the base 4424, hole 4426, and slots 4428, 4430, 4432.

The intermediate portion 4414 may be similar to the intermediate portions 2214, 1214, or other intermediate portions disclosed herein. The intermediate portion 4414 may have a shaft 4441 that is of adequate length such that the proximal end 4410 may remain outside the body while the distal end 4412 is inserted through a working portal or cannula to reach a joint space, a wound, or another anatomical region that requires suturing.

Referring to FIG. 44, two or more needles 4416 may be included in the instrument 4400. Two needles 4416, 4416' are shown in an over-and-under facing relationship. In some examples, the needles may face away from each other, or may all face the same way. The needles may be in a side-by-side relationship. Each needle may be independently actuated. Alternatively, the needles may be synchronized to actuate simultaneously or according to a desired sequence. The needle 4416 and/or 4416' may be spring loaded or spring biased to remain in, and to return to, a retracted position except when actuated distally toward an extended position of the needle. In the retracted position, the needle 4416 and/or 4416' may reside completely, or at least partially, within the interior of the base 4424 proximal to the cutout section 4420. The needle 4416 or 4416' is in a partially retracted position when the distal tip of the needle is in the proximal half of the cutout section 4420, and is in a partially extended position when the distal tip of the needle is in the distal half of the cutout section. FIG. 44 shows the first needle 4416 in a partially retracted position and the second needle 4416' in a partially extended position. The needles 4416 and 4416' each have an extended position in which the first member 4450 and the second member 4452 are received in the window 4434.

Referring to FIG. 45, the instrument 4400 may be provided with the needles 4416, 4416' in a retracted position, pre-loaded with a suture 710. Alternatively, the suture 710 may be loaded by a user at the time of use. Suture may be loaded with the needles fully retracted within the base 4424 for safety. A first free end 709 of the suture 710 may pass into the base 4424 through slot 4430, then through channel 4456 of needle 4416, then out of the base 4424 through slot 4428; and a second free end 711 of the suture 710 may pass into the base 4424 through slot 4430, then through channel 4456' of needle 4416', then out of the base 4424 through slot 4432. Each suture free end 709, 711 bends at least once going from slot 4430 to channel 4456, 4456'.

Other suture loading configurations, or routings, are contemplated. For example, in a side-by-side arrangement of the needles 4416, 4416', the base may include four slots so that the suture free ends 709, 711 may extend straight through the respective needle channel 4456, 4456' and corresponding slots. Alternatively, two separate sutures may be loaded, one engaging needle 4416 and the other engaging needle 4416'.

A method of using instrument 4400 may include some or all of the following steps: loading the suture 710 in the needles 4416, 4416'; manipulating the instrument 4400 to position a tissue portion (not shown) in the cutout section 4420; targeting a first location on the tissue; actuating the first needle 4416 to penetrate the first location on the tissue portion (FIG. 46) and push the suture 710 into the suture capture feature 4440; retracting the first needle 4416 to a retracted position, leaving the suture 710 in the suture capture feature 4440; manipulating the instrument 4400 to re-position the tissue portion in the cutout section 4420; targeting a second location on the tissue; actuating the second needle 4416' to penetrate the second location on the tissue portion and push the suture 710 into the suture capture feature 4440; retracting the second needle 4416' to a retracted position, leaving the suture 710 in the suture capture feature 4440; and removing the instrument 4400 from the body, pulling the suture 710 with it.

A modified version (not shown) of the instrument 4400 may include needle 3716 instead of needle 4416', in an arrangement like that shown in FIGS. 44-45. In this version, the distal wall may be modified to include a portion with the suture capture feature 4440 for engagement with needle 4416, and a portion with a window and a slot, like window 3734 and slot 3738 for engagement with needle 3716. The suture capture feature 4440 may include only one suture capture element 4442, and the window and slot may take the place of suture capture element 4444. This modified version provides one needle 4416 with suture-pushing capabilities, and one needle 3716 with suture-pulling capabilities. Needle 3716 could instead substitute for needle 4416, in which case the suture capture feature 4440 and window/slot would be reversed as well.

Referring to FIGS. 48-51, a distal portion of yet another instrument 4800 is shown. Instrument 4800 may also be a suture passer, and may be suitable for passing suture through tissue anywhere in the body, such as the meniscus 3626 in the knee 3600. The instrument 4800 may have a proximal end 4810 (not shown), a distal end 4812, and an intermediate portion 4814 between the proximal end 4810 and the distal end 4812. The proximal end 4810 may be identical to any of the proximal ends disclosed herein. The instrument 4800 may use the rigid needle 3716 of FIG. 42A to pass suture through tissue. In this example, needle 3716 is shown with an optional longitudinal slot 3717. Instrument 4800 may be a modification of instrument 3700 that includes a pusher component. Any of the other instruments disclosed herein may be similarly modified to include one or more pusher components. The pusher component provides pushing arms that may be used to release the suture from the suture capture feature 3760 of the needle 3716.

Figure 48:
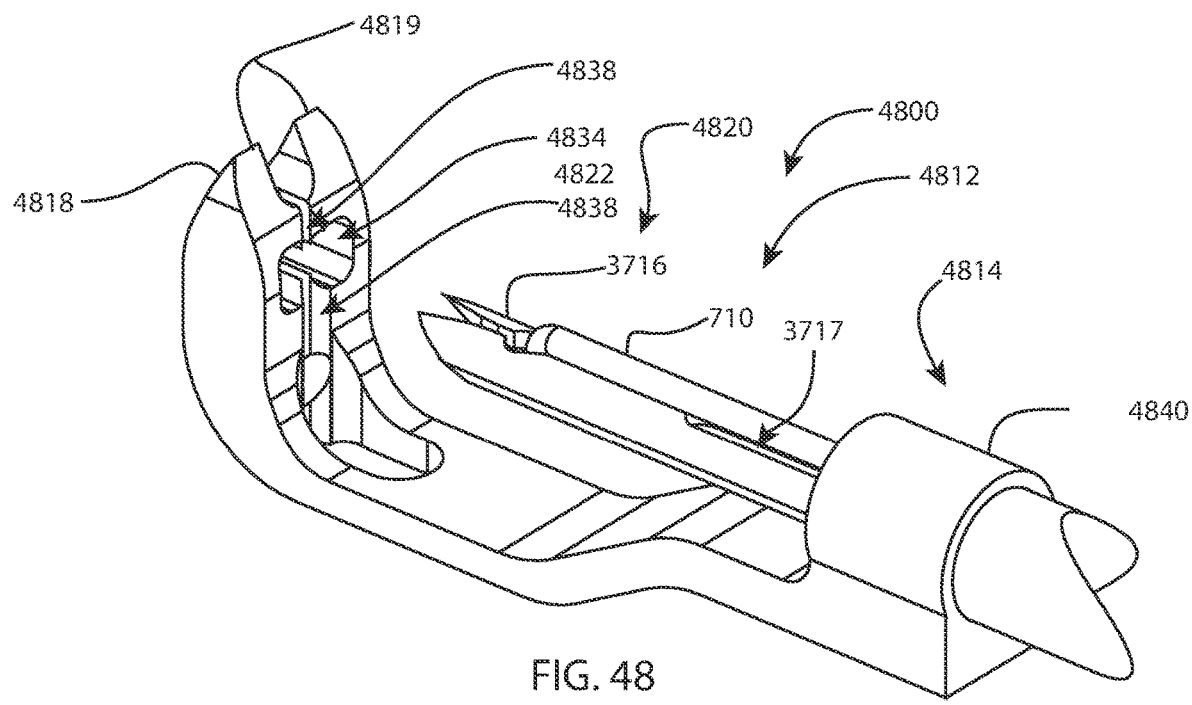
FIG. 48 is a perspective view of a distal tip portion of yet another suture passer, with a needle of the suture passer in a partially extended position, a suture carried by the needle.
Figure 49:
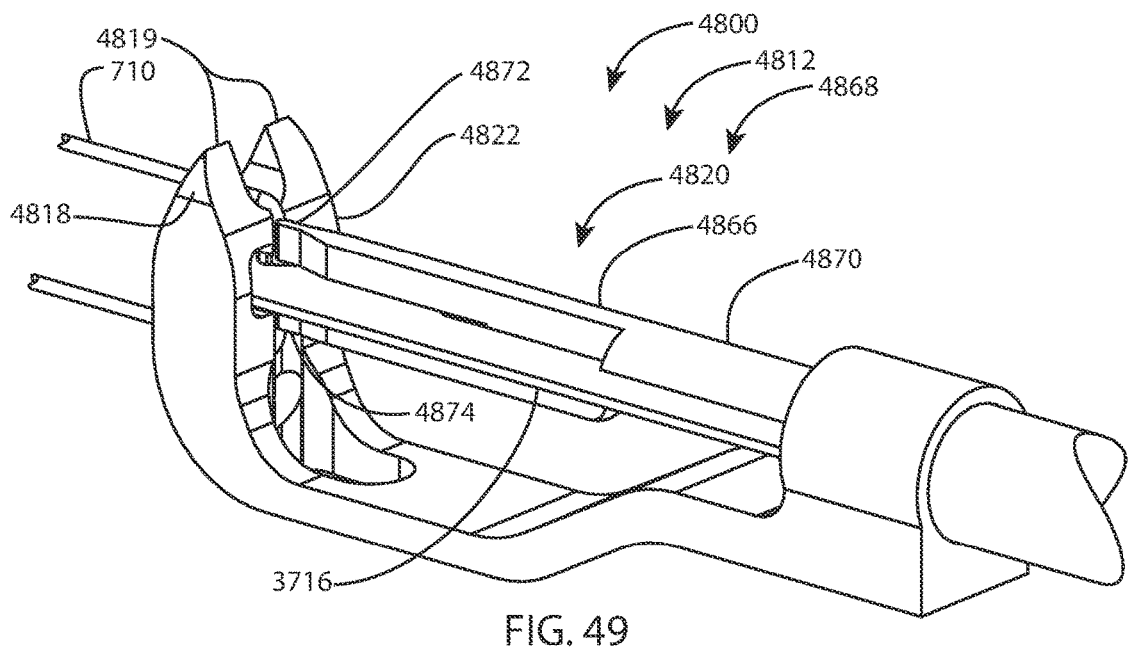
FIG. 49 is a perspective view of the distal tip portion of the suture passer of FIG. 48, with the needle of the suture passer in an extended position, with pushing arms of the suture passer in an extended position.
Figure 50:
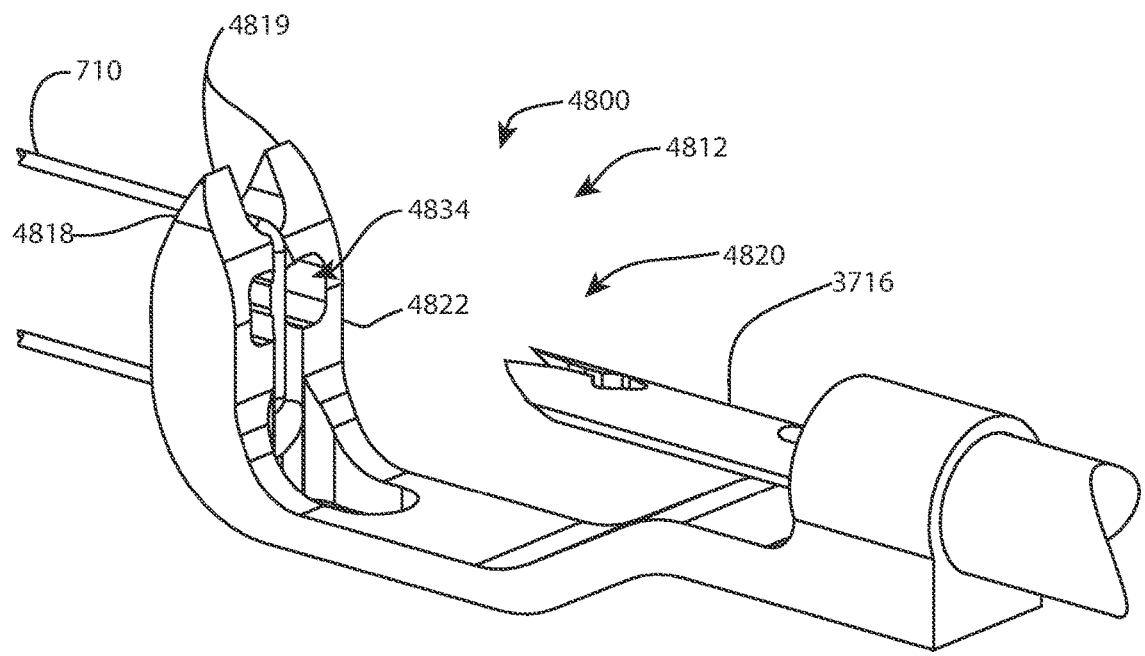
FIG. 50 is a perspective view of the distal tip portion of the suture passer of FIG. 48, with the needle in a partially retracted position, the suture carried by the distal tip portion.
Figure 51:
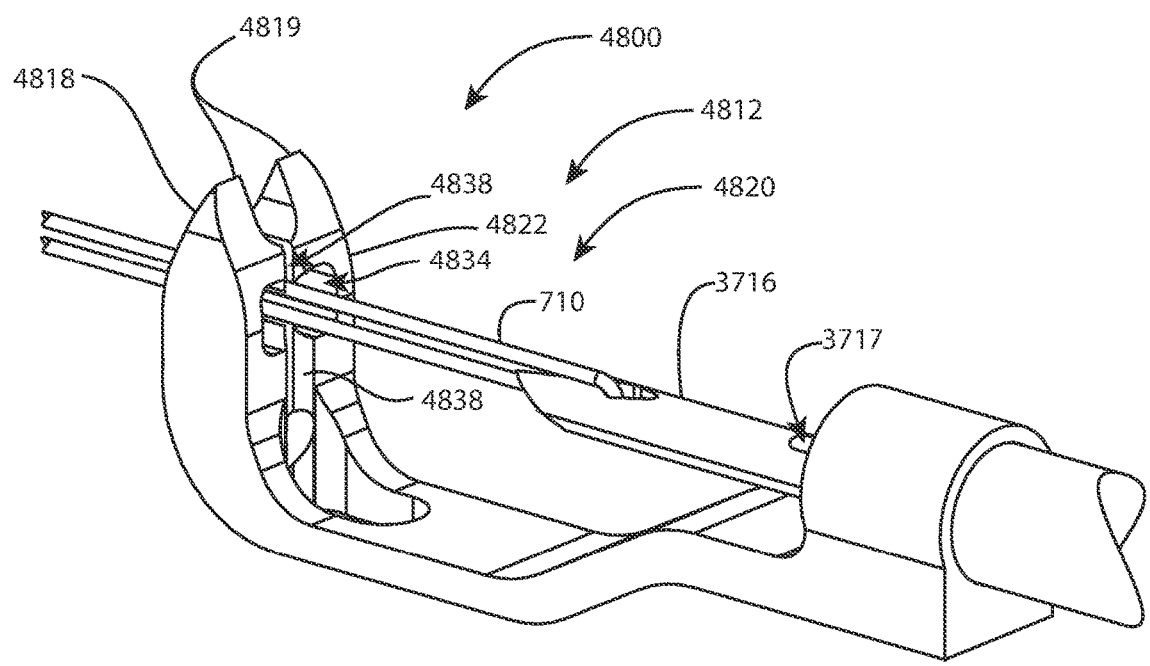
FIG. 51 is a perspective view of the distal tip portion of the suture passer of FIG. 48, with the needle in the partially retracted position, the suture carried by the needle.

Referring to FIG. 48, the distal end 4812 may have a cutout section 4820 and a distal wall 4822. The cutout section 4820 may provide a location for tissue to be inserted between the retracted needle 4816 and the distal wall 4822. The distal wall 4822 may be oriented transversely to, or generally perpendicular to, the intermediate portion 4814, in other words forming an angle of 45° to 135° with respect to the longitudinal axis of the intermediate portion 4814. FIG. 48 shows a distal wall 4822 which is substantially perpendicular to the intermediate portion 4814. The distal wall 4822 may be formed as a single piece (i.e., unitarily formed) with the cutout section 4820, and may thus be a stationary feature. This may provide additional rigidity at the distal end 4812, particularly when the tissue is being pinched between the needle tip and the distal wall 4822. Alternatively, the distal wall 4822 may be replaced by a jaw that pivots relative to the cutout section 4820 in a manner similar to that of the jaw 2222 of FIG. 22. A window 4834 may extend at least partially through the distal wall 4822 to accommodate passage of the distal end of the needle 4816 in line with the intermediate portion 4814. The window 4834 may extend longitudinally as shown, and may extend laterally through the distal wall 4822 in one or two dimensions, i.e., the height and/or width of the distal wall. The distal end of the window 4834 may have a central post 4836 (not shown) that can be used to support the suture 710 and may be used to spread the suture capture feature 4860 on the needle 4816 as previously described. In some examples, the post 4836 may stand alone, meaning that there is no distinct window framed by distal wall material. A slot 4838 may be provided to temporarily capture a section of a suture such as the suture 710. The slot 4838 may extend across a proximal face of the window 4834, and may be narrower than an uncompressed diameter of the suture 710. The narrow width of the slot 4838 may enable the slot 4838 to securely hold the suture 710 to temporarily capture it, while remaining able to release the suture 710 in response to application of a small removal force, such as that applied to the suture 710 such as when it is being retrieved by the needle 4816. The slot 4838 may optionally have a boss or other positive feature (not shown) such as a bump, wedge, or bulge that provides a secondary constraint on the suture. The window 4834, post 4836, and/or slot 4838 may together or separately be referred to as a suture holding feature or a target for the needle 4816. The distal wall 4822 may terminate in a distal tip 4818 which may include a sharp, blade-like extension 4819 that may be used to cut into or through various tissues such as tendons or ligaments. FIG. 48 shows a blade-like extension 4819 which is divided into two portions by the slot 4838, wherein the blade-like extension 4819 is beveled on two sides.

The intermediate portion 4814 may be similar to the intermediate portions 2214, 1214, or other intermediate portions disclosed herein. The intermediate portion 4814 may have a shaft 4840 that is of adequate length such that the handle 4830 and the chassis 4828 may remain outside the body while the distal end 4812 is inserted through a working portal or cannula to reach a joint space, a wound, or another anatomical region that requires suturing.

The pusher component 4866 includes a distal portion 4868 and a shaft 4870. The distal portion 4868 includes at least one pushing arm 4872. The illustrated example also shows a second pushing arm 4874. There may be a gap, slot, or space 4876 between the first and second pushing arms 4872, 4874. The space 4876 may receive the needle 3716 with clearance so that the arms 4872, 4874 are on opposite sides of the needle 3716. The shaft 4870 extends longitudinally beside the needle 3716 in the intermediate portion 4814 of the instrument 4800. The pusher component 4866 may be actuated independently of the needle 3716, and may travel parallel to the needle 3716. The pusher component 4866 may be movable between a retracted position, in which the pusher component resides completely within the intermediate portion 4814, and an extended position, in which the pusher component extends against the slot 4838 of the distal end 4812. The pusher component 4866 may be spring loaded or spring biased to remain in, and to return to, a retracted position except when its user control is urged distally to actuate, or move, the pusher component 4866 distally toward the extended position.

A method of using the instrument 4800 may be similar to the method of using instrument 3700 and/or instrument 4400 set forth above. The method may include the steps of: loading the suture 710 in the suture capture feature 3760 of the needle 3716; manipulating the instrument 4800 to position a tissue portion (not shown) in the cutout section 4820; targeting a first location on the tissue; actuating the needle 3716 to penetrate the first location on the tissue portion (FIG. 48) and push the suture into the slot 4838; actuating the pusher component 4866 distally so that the pusher arms 4872, 4874 push the suture 710 into the slot 4838; maintaining pressure against the suture 710 with the pusher arms 4872, 4874 while retracting the needle 3716; retracting the pushing arms 4872, 4874, leaving the suture 710 in the slot 4838; manipulating the instrument 4800 to re-position the tissue portion in the cutout section 4820; targeting a second location on the tissue; actuating the needle 3716 to penetrate the second location on the tissue portion, enter the window 4834, and capture the suture 710 in the suture capture feature 4860; retracting the needle 3716 with the captive suture 710 to a retracted position; and removing the instrument 4800, pulling the suture 710 with it.

The preceding disclosure of needles and other implant manipulators has focused on the distal portion of the needle, otherwise known as the point of the needle, and the intermediate portion of the needle, otherwise known as the shaft or selectively bendable portion. The proximal portion of the needle, or shank, may be connected to a separate shaft or other component of an instrument.

FIG. 52 is an exploded view of the needle 3716 and a shaft 5202, with typical prior art interconnection features. The needle 3716 is now shown with an optional hole 3715 in the shank opposite the suture capture feature 3760. The shaft 5202 includes a tongue 5204 which is reduced in size compared to the shaft 5202, and shaped for complementary fit against the shank of the needle 3716. The tongue 5204 carries a boss or post 5206 which fits in the hole 3715. In prior art systems, the needle 3716 is fixed to the shaft 5202 by an interference fit between the post 5206 and the hole 3715, by welding using the post as sacrificial filler material, by peening the post to retain the needle 3716, or the like.

FIGS. 53A-D show the needle 3716 modified to include a tubular shank 5302. In other words, this version of the needle 3716 may be fabricated from a piece of tubing, such as metal or plastic tubing, more specifically stainless steel, titanium, nitinol, polyetheretherketone (PEEK) or other similar materials. The tubing may be round or circular in cross section as shown, or triangular, square, rectangular, polygonal, oval, or another shape. The needle 3716 with shank 5302 may have a uniform cross-sectional shape along the entire length of the needle, even though material may have been removed from the cross-sectional shape in some places, for example to form the distal and intermediate portions of the needle, a slot through the needle, or a suture capture feature in the needle. The shank 5302 may include holes or slots or other interconnection features for connection to a shaft or other component of an instrument. The needle 3716 illustrated in FIGS. 53A-D simplifies the corresponding instrument (suture passer) and its assembly procedure by reducing the number of component parts and the number of steps in the assembly procedure. This shank style may be used in any of the instruments disclosed herein.

With brief reference to FIGS. 3A, 4A, 5A, 5C, 5D, and 5E, the tubing of a corresponding tubular shank of needle 300, needle 400, implant manipulator 500, implant manipulator 592, implant manipulator 593, and/or implant manipulator 594 may be triangular, quadrilateral, parallelogram, rhombus, trapezoid, diamond-shaped, square, or rectangular in cross section.

With brief reference to FIGS. 5B, 5G, and 5H, the tubing of a corresponding tubular shank of implant manipulator 550, implant manipulator 596, and/or implant manipulator 597 may be D-shaped, round, circular, oval, elliptical, or ovoid in cross section.

With brief reference to FIG. 5F, the tubing of a corresponding tubular shank of implant manipulator 595 may be quadrilateral, pentagonal, or hexagonal in cross section.

Referring to FIG. 53A, the needle 3716 with tubular shank 5302 may be fabricated by cutting a piece of tubing along a profile that extends at least partially along the length of the needle, such as the profile shown between points 5304 and 5306. The profile may be cut in multiple steps. For example, details of the distal end of the needle may be cut separately from the rest of the profile. Sharpening may also be performed as a separate step. Cutting or material removal may be performed by milling, grinding, electric discharge machining (EDM), sawing, side cutting, end cutting, lapping, honing, water jet cutting, laser cutting, or other material removal processes.

Hybrid needle designs are also contemplated. FIGS. 54A-55B illustrate some examples of hybrid needles. Hybrid needles may be used in any of the instruments disclosed herein.

Figure 54A:
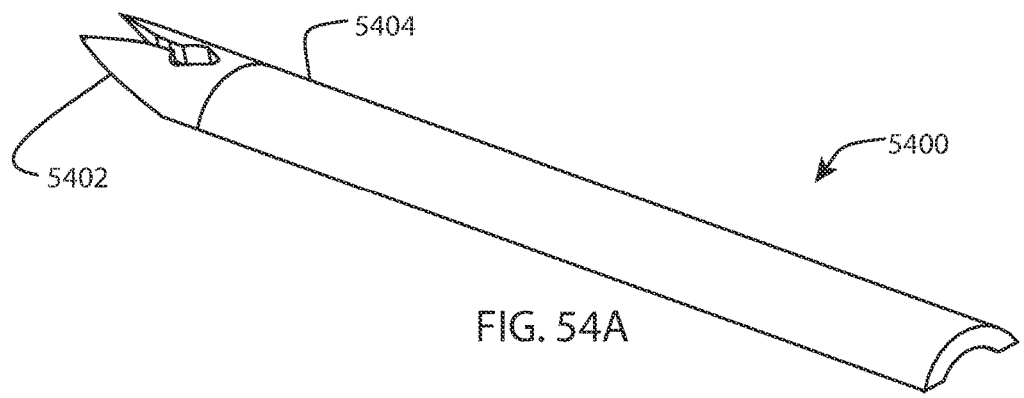
FIG. 54A is a perspective view of another needle assembly for a suture passer, with a needle tip and a needle shaft.
Figure 54B:
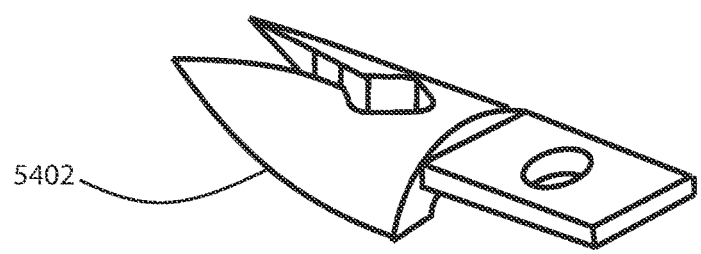
FIG. 54B is a perspective view of a distal tip portion of the needle assembly of FIG. 54A.

Referring to FIGS. 54A-B, a needle 5400 may include a distal tip portion 5402 and a separate proximal portion 5404. FIG. 54A shows that when assembled, the resulting needle 5400 may resemble needle 3716.

The distal tip portion 5402 may include a suture capture feature 5406, which may be one of the previously disclosed suture capture features, such as suture capture feature 3760 or 764 or 360. The distal tip portion 5402 may include a tab, boss, or base 5408 which extends opposite the suture capture feature 5406. The base 5408 may include roughening, teeth, serrations, ridges, grooves, hooks, or other feature, treatment, coating, or modification to enhance fixation with the proximal portion 5404. The distal tip portion 5402 may be made of metal or plastic, such as stainless steel, titanium, nitinol, PEEK, or other engineering resin.

The proximal portion 5404 may be an elongated part that replicates the intermediate portion and the proximal end of the needle 3716. The proximal portion 5404 is shown with an arcuate cross-sectional shape. However, the proximal portion 5404 may have any of the cross sectional shapes disclosed herein, or it may be polygonal, rectangular, round, oval, or trapezoidal. It will be appreciated that the cross sectional geometry of the proximal portion 5404 may be modified to produce desired bending characteristics using the same principles set forth previously in the disclosure relating to selectively bendable needles. The proximal portion 5404 may be made of polyurethanes, nylons or other polymers for flexibility.

The needle 5400 may be made by fabricating a distal tip portion 5402, placing the distal tip portion 5402 in a mold, and overmolding the proximal portion 5404 over at least the base 5408. The finished needle 5400 includes a stiff distal tip portion 5402 and a flexible polymer proximal portion 5404, and functions the same as the selectively bendable embodiments disclosed previously.

Figure 55A:
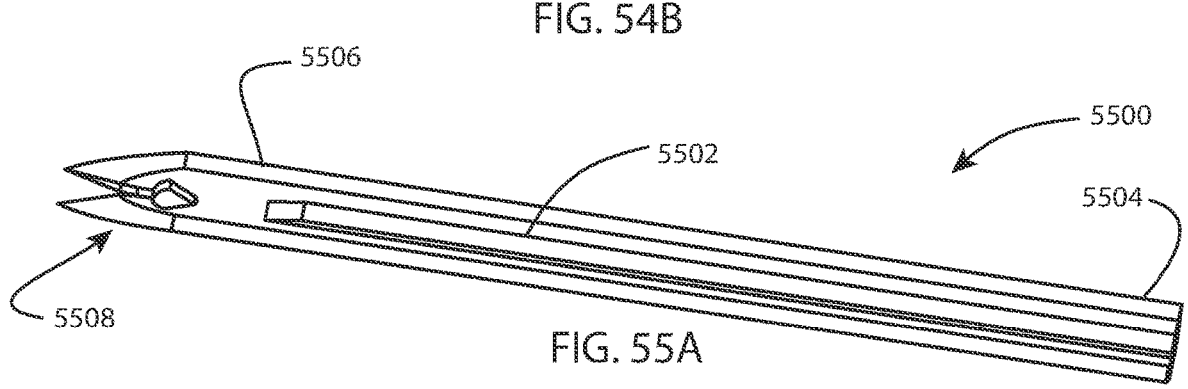
FIG. 55A is a perspective view of yet another needle assembly for a suture passer, with a needle and a spine.
Figure 55B:
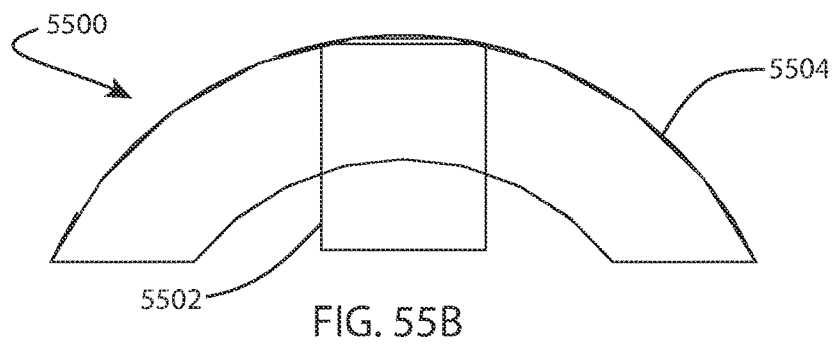
FIG. 55B is an end view of the needle assembly of FIG. 55A.

Referring to FIGS. 55A-B, yet another needle 5500 may include a spine 5502 and a needle body 5504.

The spine 5502 is an elongated part that replicates the function of the previously disclosed spines herein. The illustrated example is a rectangular solid with a beveled distal tip 5506. The spine 5502 may take on other cross sectional shapes, such as polygonal, trapezoidal, round, oval, T-shaped, I-shaped, or other relevant stiff shapes. The spine 5502 may be an extrusion. The spine 5502 may be made of metal or plastic, such as stainless steel, titanium, nitinol, PEEK, or other engineering resin.

The needle body 5504 may be identical to needle 3716, including a suture capture feature 5508. The needle body 5504 may be made of polyurethanes, nylons, PEEK, engineering resins, or other polymers.

The needle 5500 may be made by fabricating a spine 5502, placing the spine 5502 in a mold, and overmolding the needle body 5504 over at least a portion of the spine 5502. The finished needle 5500 functions the same as the rigid embodiments disclosed previously.

Figure 56:
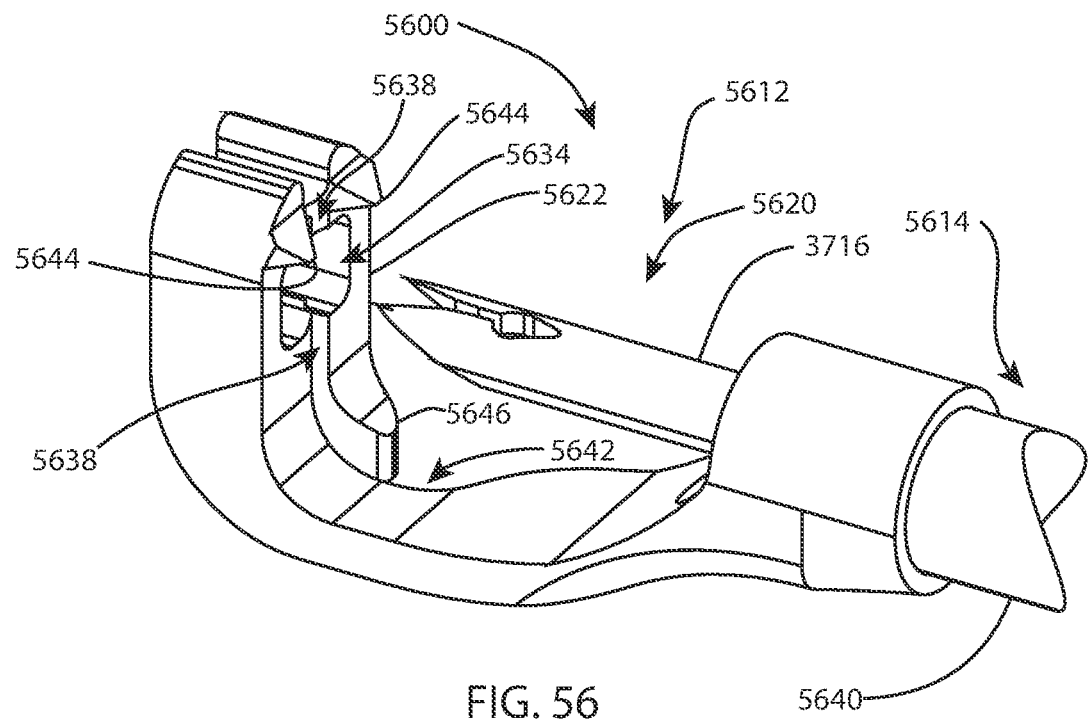
FIG. 56 is a perspective view of the distal tip portion of yet another suture passer, with a needle of the suture passer in a partially extended position.
Figure 57:
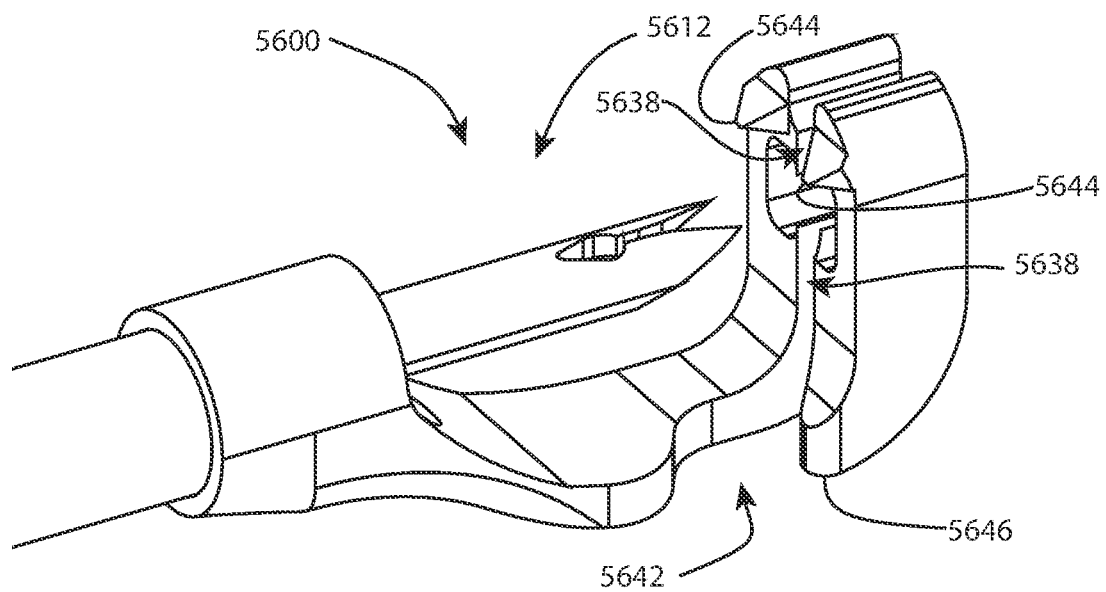
FIG. 57 is another perspective view of the distal tip portion of the suture passer of FIG. 56, from a different viewpoint.

Referring to FIGS. 56-58, a distal portion of yet another instrument 5600 is shown. Instrument 5600 may also be a suture passer, and may be suitable for passing suture through tissue anywhere in the body, such as the meniscus 3626 in the knee 3600 or a labrum in a shoulder or hip joint. The instrument 5600 may have a proximal end 5610 (not shown), a distal end 5612, and an intermediate portion 5614 between the proximal end 5610 and the distal end 5612. The proximal end 5610 may be identical to any of the proximal ends disclosed herein. The instrument 5600 may use a rigid needle 3716 to pass suture through tissue. Instrument 5600 may also be outfitted with the pusher component 4866 described for instrument 4800.

The distal end 5612 may have a cutout section 5620 and a distal wall 5622. The cutout section 5620 may provide a location for tissue to be inserted between the at least partially retracted needle 3716 and the distal wall 5622. The distal wall 5622 may be oriented transversely to, or generally perpendicular to, the intermediate portion 5614, in other words forming an angle of 45° to 135° with respect to the longitudinal axis of the intermediate portion 5614. FIG. 56 shows a distal wall 5622 which is substantially perpendicular to the intermediate portion 5614. The distal wall 5622 may be formed as a single piece (i.e., unitarily formed) with the cutout section 5620, and may thus be a stationary feature. This may provide additional rigidity at the distal end 5612, particularly when the tissue is being pinched between the needle tip and the distal wall 5622. Alternatively, the distal wall 5622 may be replaced by a jaw that pivots relative to the cutout section 5620 in a manner similar to that of the jaw 2222 of FIG. 22. A window 5634 may extend at least partially through the distal wall 5622 to accommodate passage of the distal end of the needle 3716 in line with the intermediate portion 5614. The window 5634 may extend longitudinally as shown, and may extend laterally through the distal wall 5622 in one or two dimensions, i.e., the height and/or width of the distal wall. The distal end of the window 5634 may have a central post 5636 (FIG. 58) that can be used to support the suture 710 and may be used to spread the suture capture feature 5660 on the needle 3716 as previously described. In some examples, the post 5636 may stand alone, meaning that there is no distinct window framed by distal wall material. A slot 5638 may be provided to temporarily capture a section of a suture such as the suture 710. The slot 5638 may extend across a proximal face of the window 5634, and may be narrower than an uncompressed diameter of the suture 710. The narrow width of the slot 5638 may enable the slot 5638 to securely hold the suture 710 to temporarily capture it, while remaining able to release the suture 710 in response to application of a small removal force, such as that applied to the suture 710 such as when it is being retrieved by the needle 3716. The slot 5638 may optionally have a boss or other positive feature (not shown) such as a bump, wedge, or bulge that provides a secondary constraint on the suture. The window 5634, post 5636, and/or slot 5638 may together or separately be referred to as a suture holding feature or a target for the needle 3716. In this example, the proximal portion of the slot 5638 extends laterally through one side of the distal end 5612 in the cutout section 5620, forming an enlarged lateral alcove 5642 along the cutout section 5620. The slot 5638 is thus open and accessible from a lateral direction for engaging with, disengaging from, or manipulating a suture. This arrangement may be referred to as side loading. The distal wall 5622 adjacent to the alcove 5642 extends proximally, terminating in a proximally-projecting free end 5646. The distal wall 5622 and the free end 5646 may also be described as a forming a hook. A side loading configuration similar to, or identical to, slot 5636, alcove 5642, and free end 5646 may be present in any of the distal ends disclosed herein. The distal wall 5622 may support one or more proximally-facing protrusions 5644, which may be spikes, teeth, serrations, ridges, grooves, or other proximally-projecting features. The protrusion(s) 5644 may be beveled, pyramidal, conical, sharpened, or rough. Two four-sided pyramidal protrusions 5644 are shown on either side of the slot 5638 near the window 5634. The protrusion(s) 5644 may stabilize the distal end 5612 against tissue as the needle 3716 is passed through the tissue, and may be present in any of the distal ends disclosed herein.

The intermediate portion 5614 may be similar to the intermediate portions 2214, 1214, or other intermediate portions disclosed herein. The intermediate portion 5614 may have a shaft 5640 that is of adequate length such that the proximal end 5610 may remain outside the body while the distal end 5612 is inserted through a working portal or cannula to reach a joint space, a wound, or another anatomical region that requires suturing.

The needle 3716 may be spring loaded or spring biased to remain in, and to return to, a retracted position except when actuated, or moved, distally toward an extended position of the needle. The needle 3716 may reside completely, or at least partially, within the interior of the intermediate portion 5614 proximal to the cutout section 5620. The needle 3716 is in a partially retracted position when the distal tip of the needle is in the proximal half of the cutout section 5620, and is in a partially extended position when the distal tip of the needle is in the distal half of the cutout section.

Instrument 5600 may be used according to the method set forth above for instrument 3700.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention. Embodiments of the invention in which an exclusive property or privilege is claimed are defined as follows.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The invention claimed is:

1. A suture passer system for a suture comprising a first free end, a second free end opposite the first free end, and a middle portion between the first free end and the second free end, the suture passer system comprising:
   a suture passer comprising a proximal end, a distal end opposite the proximal end, an intermediate portion coupled to and extending between the proximal end and the distal end, and a first needle residing at least partially within the intermediate portion;
   wherein the distal end of the suture passer comprises a suture holding feature;
   wherein a distal end of the first needle comprises a distally-sharpened first member with a first distally-oriented tip, a distally-sharpened second member with a second distally-oriented tip, and a channel extending between the first member and the second member;
   wherein the first needle is movable between a retracted position and an extended position, wherein the first needle resides at least partially within the intermediate portion of the suture passer when the first needle is in the retracted position, wherein the first needle extends to the suture holding feature in the distal end of the suture passer when the first needle is in the extended position;
   wherein the suture is transferred between the distal end of the suture passer and the first needle when the first needle moves between the retracted position and the extended position;
   wherein the first needle comprises an intermediate portion having a cross-sectional shape that is non-rectangular.

2. The suture passer system of claim 1, wherein the suture holding feature comprises a slot extending across the distal end of the suture passer, wherein the suture is transferred between the slot and the channel when the first needle moves between the retracted position and the extended position.

3. The suture passer system of claim 2, wherein the first needle comprises a capture hole, wherein the channel provides access to the capture hole; wherein the suture is transferred between the slot and the capture hole when the first needle moves between the retracted position and the extended position.

4. The suture passer system of claim 3, comprising:
   a pusher component comprising a shaft and a distal portion extending from the shaft, the distal portion comprising at least one pushing arm;
   wherein the pusher component is movable between a retracted position and an extended position, wherein the pusher component resides at least partially within the intermediate portion of the suture passer when the pusher component is in the retracted position, wherein the pusher component extends against the slot of the distal end of the suture passer when the pusher component in the extended position;

wherein the suture is transferred from the capture hole to the slot when the first needle is in the extended position and the pusher component moves between the retracted position and the extended position.

5. The suture passer system of claim 4, wherein the pusher component is biased to remain in, or to automatically move to, the retracted position except when the pusher component is actuated to move the pusher component distally toward the extended position.

6. The suture passer system of claim 1, wherein the distal end of the suture passer comprises a sharp, blade-like extension.

7. The suture passer system of claim 1, wherein the suture holding feature comprises a first tab coupled to the distal end of the suture passer, wherein the suture is transferred from the channel to the first tab when the first needle moves between the retracted position and the extended position.

8. The suture passer system of claim 1, wherein the distal end of the suture passer comprises a distal wall and a base opposite the distal wall, wherein the base is coupled to the intermediate portion of the suture passer, wherein the base includes at least one slot that receives the suture, wherein the at least one slot of the base is aligned with the channel of the first needle when the first needle is in the retracted position.

9. The suture passer system of claim 8, wherein the distal wall comprises at least one proximally-facing protrusion.

10. The suture passer system of claim 1, wherein the first needle is biased to remain in, or to automatically move to, the retracted position except when the first needle is actuated to move the first needle distally toward the extended position.

11. The suture passer system of claim 1, comprising:
a second needle residing at least partially within the intermediate portion of the suture passer;
wherein a distal end of the second needle comprises a distally-sharpened first member, a distally-sharpened second member, and a channel extending between the first member of the second needle and the second member of the second needle;
wherein the second needle is movable between a retracted position and an extended position, wherein the second needle resides at least partially within the intermediate portion of the suture passer when the second needle is in the retracted position, wherein the second needle extends to the suture holding feature in the distal end of the suture passer when the second needle is in the extended position;
wherein the suture is transferred between the distal end of the suture passer and the second needle when the second needle moves between the retracted position and the extended position.

12. The suture passer system of claim 11, wherein the suture holding feature comprises a second tab coupled to the distal end of the suture passer, wherein the suture is transferred from the channel of the second needle to the second tab when the second needle moves between the retracted position and the extended position.

13. The suture passer system of claim 11, wherein the suture holding feature comprises a slot extending across the distal end of the suture passer, wherein the suture is transferred between the slot and the channel of the second needle when the second needle moves between the retracted position and the extended position.

14. The suture passer system of claim 13, wherein the second needle comprises a capture hole, wherein the channel of the second needle provides access to the capture hole of the second needle; wherein the suture is transferred between the slot and the capture hole of the second needle when the second needle moves between the retracted position and the extended position.

15. A suture passer system for a suture comprising a first free end, a second free end opposite the first free end, and a middle portion between the first free end and the second free end, the suture passer system comprising:
a suture passer comprising a proximal end, a distal end opposite the proximal end, an intermediate portion coupled to and extending between the proximal end and the distal end, and a first needle residing at least partially within the intermediate portion;
wherein the distal end of the suture passer comprises a distal wall oriented transversely to the intermediate portion, wherein the distal wall comprises a suture holding feature;
wherein the first needle is movable between a retracted position and an extended position, wherein the first needle resides at least partially within the intermediate portion of the suture passer when the first needle is in the retracted position, wherein the first needle extends to the suture holding feature when the first needle is in the extended position;
wherein the suture is transferred between the distal end of the suture passer and a distally-facing capture feature of the first needle when the first needle moves between the retracted position and the extended position;
wherein the first needle comprises an intermediate portion having a cross-sectional shape that is non-rectangular and non-circular.

16. The suture passer system of claim 15, wherein the distal wall terminates in a sharp, blade-like extension that is divided into at least two portions by at least one slot.

17. The suture passer system of claim 15, wherein the distal wall terminates in a sharp, blade-like extension with at least two sides that are beveled.

18. A suture passer system for a suture comprising a first free end, a second free end opposite the first free end, and a middle portion between the first free end and the second free end, the suture passer system comprising:
a suture passer comprising a proximal end, a distal end opposite the proximal end, an intermediate portion coupled to and extending between the proximal end and the distal end, a first needle residing at least partially within the intermediate portion, and a first pusher component residing at least partially within the intermediate portion;
wherein the distal end of the suture passer comprises a suture holding feature;
wherein the first pusher component comprises at least one pushing arm extending beside the first needle;
wherein the first needle comprises a distal end comprising a capture hole configured to receive the middle portion;
wherein the first needle is movable between a retracted position and an extended position, wherein the first needle resides at least partially within the intermediate portion of the suture passer when the first needle is in the retracted position, wherein the first needle extends to the suture holding feature when the first needle is in the extended position;
wherein the first pusher component is movable, along a direction parallel to the distal end of the first needle in the extended position of the first needle, between a retracted position and an extended position, wherein the first pusher component resides at least partially within the intermediate portion of the suture passer when the first pusher component is in the retracted position, wherein the first pusher component extends to the suture holding feature when the first pusher component is in the extended position;

wherein the middle portion of the suture is transferred from the capture hole of the first needle to the distal end of the suture passer when the first needle is in the extended position and the first pusher component moves between the retracted position and the extended position.

19. The suture passer system of claim 18, wherein the first pusher component is independently movable relative to the first needle.

20. The suture passer system of claim 18, wherein the first pusher component comprises a shaft and a distal portion extending from the shaft, wherein the distal portion comprises the at least one pushing arm; wherein the shaft of the first pusher component extends beside the needle in the intermediate portion of the suture passer.

* * * * *